US006025543A

United States Patent [19]
Yanofsky

[11] Patent Number: 6,025,543
[45] Date of Patent: *Feb. 15, 2000

[54] SEED PLANTS EXHIBITING EARLY REPRODUCTIVE DEVELOPMENT AND METHODS OF MAKING SAME

[75] Inventor: Martin F. Yanofsky, San Diego, Calif.

[73] Assignee: The Regents of the University of California, Oakland, Calif.

[*] Notice: This patent is subject to a terminal disclaimer.

[21] Appl. No.: 08/655,241

[22] Filed: Jun. 5, 1996

[51] Int. Cl.$^7$ .............................. A01H 5/00; C12N 15/29; C12N 15/82

[52] U.S. Cl. .......................... 800/290; 800/278; 800/298; 800/306; 800/312; 800/315; 800/316; 800/320; 800/322; 800/323; 435/468; 536/23.6

[58] Field of Search ............................ 800/205, DIG. 17, 800/23, 30, 38, 11, 49, 55, 62, 64, 65, 69, 278, 290, 298, 320, 312, 306, 322, 315, 316, 323; 536/23.6; 435/172.3, 468

[56] References Cited

U.S. PATENT DOCUMENTS 5,637,785  6/1997  Weigel ..................................... 800/205
5,844,119  12/1998 Weigel ..................................... 800/205

FOREIGN PATENT DOCUMENTS

WO 96/19105  6/1996  WIPO.

OTHER PUBLICATIONS

Liljegren et al. 1996. Curr. Opinion Cell Biol. 8:865–869.
Ma, H. 1998. TIG 14(1):26–32.
Bowman et al., "Control of Flower Development in *Arabidopsis Thaliana* by APETALA1 and Interacting Genes," *Development* 119:721–743 (1993).
Schultz and Haughn, "Genetic Analysis of the Floral Initiation Process (FLIP) in Arabidopsis," *Development* 199:745–765 (1993).
Shannon and Meeks–Wagner, "A Mutation in the Arabidopsis TFL1 Gene Affects Inflorescence Meristem Development," *The Plant Cell* 3:877–892 (1991).
Shannon and Meeks–Wagner, "Genetic Interactions that Regulate Inflorescence Development in Arabidopsis," *The Plant Cell* 5:639–655 (1993).
Weigel and Nilsson, "A Development Switch Sufficient for Flower Initiation in Diverse Plants," *Nature* 377:495–500 (1995).
Alvarez et al., "Terminal flower: A Gene Affecting Inflorescence Development in *Arabidopsis thaliana*," *Plant J.* 2:103–116 (1992) No. 1.
Anthony et al., "Cloning and Sequence Analysis of a flo–lfy Homologue Isolated From Cauliflower (*Brassica oleracea* L. var. *botrytis*)," *Plant Molecular Biology* 22:1163–1166 (1993).
Anthony et al., "The cDNA Sequence of a Cauliflower apetala–1/squamosa Homolog," *Plant Physiol.* 108:441–442 (1995).
"Blooming on Command," *Salk Institute Signals* Winter:4–6 (1996).

Chung et al., "Early Flowering and Reduced Apical Dominance Result From Ectopic Expression of a Rice MADS Box Gene," *Plant Mol. Biol.* 26:657–665 (1994).
Coen et al., "FLORICAULA: A Homeotic Gene Required for Flower Development in *Antirrhinum majus*," *Cell* 63:1311–1322 (1990) No. 4.
Huijser et al., "Bracteomania, an Inflorescence Anomaly, is Caused by the Loss of Function of the MADS–box Gene Squamous in *Antirrhimun majus*," *EMBO J.* 11:1239–1249 (1992).
Kelly et al., "NFL, the Tobacco Homolog of FLORICAULA and LEAFY, is Transcriptionally Expressed in Both Vegetative and Floral Meristems," *Plant Cell* 7:225–234 (1995).
Kempin et al., "Molecular Basis of the cauliflower Phenotype in Arabidopsis," *Science* 267:522–525 (1995).
Mandel et al., "Function and Regulation of the Arabidopsis APETALA1 Gene", poster presented at The Sixth International Meeting on Arabidopsis Research, Jun. 7–11, 1995.
Mandel et al., "Molecular Characterization of the Arabidopsis Floral Homeotic Gene Apetala1," *Nature* 360:273–277 (1992).
Mandel and Yanofsky, "A Gene Triggering Flower Formation in Arabidopsis," *Nature* 377:522–524 (1995).
Mena et al., "A Characterization of the MADS–Box Gene Family in Maize," *The Plant Journal* 8(6), 845–854 (1995).
Purugganan et al., "Molecular Evolution of Flower Development: Diversification of the Plant MADS–Box Regulatory Gene Family," *Genetics* 140:345–356 (1995).
Putterill et al., "The CONSTANS Gene of Arabidopsis Promotes Flowering and Encodes a Protein Showing Similarities to Zinc Finger Transcription Factors," *Cell* 80:847–857 (1995).
Rottman et al., "Structure and Expression of a LEAFY Homolog From Populus," *Cell Biochem. Suppl.* 17B:23 (1993).
Savidge et al., "Molecular Basis of the Cauliflower Phenotype", talk presented by Beth Savidge at The Sixth International Meeting on Arabidopsis Research, Jun. 7–11, 1995.
Sommer et al., "Deficiens, a Homeotic Gene Involved in the Control of Flower Morphogenesis in *Antirrhinum Majus*: the Protein Shows Homology to Transcription Factors," *The EMBO Journal* 9:606–613 (1990) No. 3.
Strauss et al., "Genetic Engineering of Reproductive Sterility in Forest Trees," *Molec. Breed.* 1:5–26 (1995).

(List continued on next page.)

*Primary Examiner*—David T. Fox
*Attorney, Agent, or Firm*—Campbell & Flores LLP

[57] ABSTRACT

The present invention provides a non-naturally occurring seed plant such as a transgenic angiosperm or gymnosperm that contains an ectopically expressible nucleic acid molecule encoding a floral meristem identity gene product. The invention further provides a method of converting shoot meristem to floral meristem in an angiosperm by ectopically expressing a floral meristem identity gene product in the angiosperm. In addition, the invention provides a method of promoting early reproductive development in a seed plant by ectopically expressing a floral meristem identity gene product in the seed plant.

21 Claims, 1 Drawing Sheet

OTHER PUBLICATIONS

Weigel, "The Genetics of Flower Development: From Floral Induction to Ovule Morphogenesis," *Ann. Rev. Genetics* 29:19–39 (1995).

Weigel and Nilsson, "Leafy Encodes a Developmental Switch", talk presented by Detlef Weigel at The Sixth International Meeting on Arabidopsis Research, Jun. 7–11, 1995.

Weigel et al., "LEAFY Controls Floral Meristem Identity in Arabidopsis," *Cell* 69:843–859 (1992).

Yanofsky, "Floral Meristems to Floral Organs: Genes Controlling Early Events in Arabidopsis Flower Development," *Annu. Rev. Plant Physiol. Plant Mol. Biol.* 46:167–188 (1995).

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1057 base pairs

```
              (B) TYPE: nucleic acid
              (C) STRANDEDNESS: double
              (D) TOPOLOGY: linear (ix) FEATURE:
              (A) NAME/KEY: CDS
              (B) LOCATION: 124..893

(ix) FEATURE:
              (A) NAME/KEY: misc_feature
              (B) LOCATION: 1..1057
              (D) OTHER INFORMATION: /note= "product = Arabidopsis
                   thaliana AP1."

(xi) SEQUENCE DESCRIPTION: SEQ ID NO:1:

CTTTCCAATT GGTTCATACC AAAGTCTGAG CTCTTCTTTA TATCTCTCTT GTAGTTTCTT      60

ATTGGGGGTC TTTGTTTTGT TTGGTTCTTT TAGAGTAAGA AGTTTCTTAA AAAAGGATCA     120

AAA ATG GGA AGG GGT AGG GTT CAA TTG AAG AGG ATA GAG AAC AAG ATC      168
    Met Gly Arg Gly Arg Val Gln Leu Lys Arg Ile Glu Asn Lys Ile
    1               5                  10                  15

AAT AGA CAA GTG ACA TTC TCG AAA AGA AGA GCT GGT CTT TTG AAG AAA      216
Asn Arg Gln Val Thr Phe Ser Lys Arg Arg Ala Gly Leu Leu Lys Lys
                20                  25                  30

GCT CAT GAG ATC TCT GTT CTC TGT GAT GCT GAA GTT GCT CTT GTT GTC      264
Ala His Glu Ile Ser Val Leu Cys Asp Ala Glu Val Ala Leu Val Val
            35                  40                  45

TTC TCC CAT AAG GGG AAA CTC TTC GAA TAC TCC ACT GAT TCT TGT ATG      312
Phe Ser His Lys Gly Lys Leu Phe Glu Tyr Ser Thr Asp Ser Cys Met
        50                  55                  60

GAG AAG ATA CTT GAA CGC TAT GAG AGG TAC TCT TAC GCC GAA AGA CAG      360
Glu Lys Ile Leu Glu Arg Tyr Glu Arg Tyr Ser Tyr Ala Glu Arg Gln
    65                  70                  75

CTT ATT GCA CCT GAG TCC GAC GTC AAT ACA AAC TGG TCG ATG GAG TAT      408
Leu Ile Ala Pro Glu Ser Asp Val Asn Thr Asn Trp Ser Met Glu Tyr
80                  85                  90                  95

AAC AGG CTT AAG GCT AAG ATT GAG CTT TTG GAG AGA AAC CAG AGG CAT      456
Asn Arg Leu Lys Ala Lys Ile Glu Leu Leu Glu Arg Asn Gln Arg His
                100                 105                 110

TAT CTT GGG GAA GAC TTG CAA GCA ATG AGC CCT AAA GAG CTT CAG AAT      504
Tyr Leu Gly Glu Asp Leu Gln Ala Met Ser Pro Lys Glu Leu Gln Asn
            115                 120                 125

CTG GAG CAG CAG CTT GAC ACT GCT CTT AAG CAC ATC CGC ACT AGA AAA      552
Leu Glu Gln Gln Leu Asp Thr Ala Leu Lys His Ile Arg Thr Arg Lys
        130                 135                 140

AAC CAA CTT ATG TAC GAG TCC ATC AAT GAG CTC CAA AAA AAG GAG AAG      600
Asn Gln Leu Met Tyr Glu Ser Ile Asn Glu Leu Gln Lys Lys Glu Lys
    145                 150                 155

GCC ATA CAG GAG CAA AAC AGC ATG CTT TCT AAA CAG ATC AAG GAG AGG      648
Ala Ile Gln Glu Gln Asn Ser Met Leu Ser Lys Gln Ile Lys Glu Arg
160                 165                 170                 175

GAA AAA ATT CTT AGG GCT CAA CAG GAG CAG TGG GAT CAG CAG AAC CAA      696
Glu Lys Ile Leu Arg Ala Gln Gln Glu Gln Trp Asp Gln Gln Asn Gln
                180                 185                 190

GGC CAC AAT ATG CCT CCC CCT CTG CCA CCG CAG CAG CAC CAA ATC CAG      744
Gly His Asn Met Pro Pro Pro Leu Pro Pro Gln Gln His Gln Ile Gln
            195                 200                 205

CAT CCT TAC ATG CTC TCT CAT CAG CCA TCT CCT TTT CTC AAC ATG GGT      792
His Pro Tyr Met Leu Ser His Gln Pro Ser Pro Phe Leu Asn Met Gly
        210                 215                 220

GGT CTG TAT CAA GAA GAT GAT CCA ATG GCA ATG AGG AGG AAT GAT CTC      840
Gly Leu Tyr Gln Glu Asp Asp Pro Met Ala Met Arg Arg Asn Asp Leu
    225                 230                 235
```

```
GAA CTG ACT CTT GAA CCC GTT TAC AAC TGC AAC CTT GGC TGC TTC GCC         888
Glu Leu Thr Leu Glu Pro Val Tyr Asn Cys Asn Leu Gly Cys Phe Ala
240                 245                 250                 255

GCA TG AAGCATTTCC ATATATATAT TTGTAATCGT CAACAATAAA AACAGTTTGC           943
Ala

CACATACATA TAAATAGTGG CTAGGCTCTT TTCATCCAAT TAATATATTT TGGCAAATGT       1003

TCGATGTTCT TATATCATCA TATATAAATT AGCAGGCTCC TTTCTTTTTT TGTA            1057

(2) INFORMATION FOR SEQ ID NO:2:

(i) SEQUENCE CHARACTERISTICS:
        (A) LENGTH: 256 amino acids
        (B) TYPE: amino acid
        (D) TOPOLOGY: linear (ii) MOLECULE TYPE: protein (xi) SEQUENCE DESCRIPTION: SEQ ID NO:2:

Met Gly Arg Gly Arg Val Gln Leu Lys Arg Ile Glu Asn Lys Ile Asn
1               5                   10                  15

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Gln Asn Gln Gly
            180                 185                 190

His Asn Met Pro Pro Leu Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255

(2) INFORMATION FOR SEQ ID NO:3:

(i) SEQUENCE CHARACTERISTICS:
        (A) LENGTH: 794 base pairs
        (B) TYPE: nucleic acid
        (C) STRANDEDNESS: double
```

(D) TOPOLOGY: linear (ii) MOLECULE TYPE: cDNA (ix) FEATURE:
    (A) NAME/KEY: CDS
    (B) LOCATION: 36..794

(ix) FEATURE:
    (A) NAME/KEY: misc_feature
    (B) LOCATION: 1..794
    (D) OTHER INFORMATION: /note= "product = Brassica oleracea AP1."

(xi) SEQUENCE DESCRIPTION: SEQ ID NO:3:

```
TCTTAGAGGA AATAGTTCCT TTAAAAGGGA TAAAA ATG GGA AGG GGT AGG GTT         53
                                      Met Gly Arg Gly Arg Val
                                       1               5

CAG TTG AAG AGG ATA GAA AAC AAG ATC AAT AGA CAA GTG ACA TTC TCG       101
Gln Leu Lys Arg Ile Glu Asn Lys Ile Asn Arg Gln Val Thr Phe Ser
            10                  15                  20

AAA AGA AGA GCT GGT CTT ATG AAG AAA GCT CAT GAG ATC TCT GTT CTG       149
Lys Arg Arg Ala Gly Leu Met Lys Lys Ala His Glu Ile Ser Val Leu
        25                  30                  35

TGT GAT GCT GAA GTT GCG CTT GTT GTC TTC TCC CAT AAG GGG AAA CTC       197
Cys Asp Ala Glu Val Ala Leu Val Val Phe Ser His Lys Gly Lys Leu
    40                  45                  50

TTT GAA TAC TCC ACT GAT TCT TGT ATG GAG AAG ATA CTT GAA CGC TAT       245
Phe Glu Tyr Ser Thr Asp Ser Cys Met Glu Lys Ile Leu Glu Arg Tyr
55                  60                  65                  70

GAG AGA TAC TCT TAC GCC GAG AGA CAG CTT ATA GCA CCT GAG TCC GAC       293
Glu Arg Tyr Ser Tyr Ala Glu Arg Gln Leu Ile Ala Pro Glu Ser Asp
                75                  80                  85

TCC AAT ACG AAC TGG TCG ATG GAG TAT AAT AGG CTT AAG GCT AAG ATT       341
Ser Asn Thr Asn Trp Ser Met Glu Tyr Asn Arg Leu Lys Ala Lys Ile
            90                  95                 100

GAG CTT TTG GAG AGA AAC CAG AGG CAC TAT CTT GGG GAA GAC TTG CAA       389
Glu Leu Leu Glu Arg Asn Gln Arg His Tyr Leu Gly Glu Asp Leu Gln
        105                 110                 115

GCA ATG AGC CCT AAG GAA CTC CAG AAT CTA GAG CAA CAG CTT GAT ACT       437
Ala Met Ser Pro Lys Glu Leu Gln Asn Leu Glu Gln Gln Leu Asp Thr
    120                 125                 130

GCT CTT AAG CAC ATC CGC TCT AGA AAA AAC CAA CTT ATG TAC GAC TCC       485
Ala Leu Lys His Ile Arg Ser Arg Lys Asn Gln Leu Met Tyr Asp Ser
135                 140                 145                 150

ATC AAT GAG CTC CAA AGA AAG GAG AAA GCC ATA CAG GAA CAA AAC AGC       533
Ile Asn Glu Leu Gln Arg Lys Glu Lys Ala Ile Gln Glu Gln Asn Ser
                155                 160                 165

ATG CTT TCC AAG CAG ATT AAG GAG AGG GAA AAC GTT CTT AGG GCG CAA       581
Met Leu Ser Lys Gln Ile Lys Glu Arg Glu Asn Val Leu Arg Ala Gln
            170                 175                 180

CAA GAG CAA TGG GAC GAG CAG AAC CAT GGC CAT AAT ATG CCT CCG CCT       629
Gln Glu Gln Trp Asp Glu Gln Asn His Gly His Asn Met Pro Pro Pro
        185                 190                 195

CCA CCC CCG CAG CAG CAT CAA ATC CAG CAT CCT TAC ATG CTC TCT CAT       677
Pro Pro Pro Gln Gln His Gln Ile Gln His Pro Tyr Met Leu Ser His
    200                 205                 210

CAG CCA TCT CCT TTT CTC AAC ATG GGG GGG CTG TAT CAA GAA GAA GAT       725
Gln Pro Ser Pro Phe Leu Asn Met Gly Gly Leu Tyr Gln Glu Glu Asp
215                 220                 225                 230

CAA ATG GCA ATG AGG AGG AAC GAT CTC GAT CTG TCT CTT GAA CCC GGT       773
Gln Met Ala Met Arg Arg Asn Asp Leu Asp Leu Ser Leu Glu Pro Gly
                235                 240                 245
```

```
TAT AAC TGC AAT CTC GGC TGC                                                        794
Tyr Asn Cys Asn Leu Gly Cys
            250
```

(2) INFORMATION FOR SEQ ID NO:4:

(i) SEQUENCE CHARACTERISTICS:
        (A) LENGTH: 253 amino acids
        (B) TYPE: amino acid
        (D) TOPOLOGY: linear (ii) MOLECULE TYPE: protein (xi) SEQUENCE DESCRIPTION: SEQ ID NO:4:

```
Met Gly Arg Gly Arg Val Gln Leu Lys Arg Ile Glu Asn Lys Ile Asn
 1               5                  10                  15

Arg Gln Val Thr Phe Ser Lys Arg Arg Ala Gly Leu Met Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Ser Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Ser Arg Lys Asn
    130                 135                 140

Gln Leu Met Tyr Asp Ser Ile Asn Glu Leu Gln Arg Lys Glu Lys Ala
145                 150                 155                 160

Ile Gln Glu Gln Asn Ser Met Leu Ser Lys Gln Ile Lys Glu Arg Glu
                165                 170                 175

Asn Val Leu Arg Ala Gln Gln Glu Gln Trp Asp Glu Gln Asn His Gly
            180                 185                 190

His Asn Met Pro Pro Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Glu Asp Gln Met Ala Met Arg Arg Asn Asp Leu Asp
225                 230                 235                 240

Leu Ser Leu Glu Pro Gly Tyr Asn Cys Asn Leu Gly Cys
                245                 250
```

(2) INFORMATION FOR SEQ ID NO:5:

(i) SEQUENCE CHARACTERISTICS:
        (A) LENGTH: 768 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..766

(ix) FEATURE:
    (A) NAME/KEY: misc_feature
    (B) LOCATION: 1..768
    (D) OTHER INFORMATION: /note= "product = Brassica oleracea
        var. botrytis AP1."

(xi) SEQUENCE DESCRIPTION: SEQ ID NO:5:

```
ATG GGA AGG GGT AGG GTT CAG TTG AAG AGG ATA GAA AAC AAG ATC AAT        48
Met Gly Arg Gly Arg Val Gln Leu Lys Arg Ile Glu Asn Lys Ile Asn
 1               5                  10                  15

AGA CAA GTG ACA TTC TCG AAA AGA AGA GCT GGT CTT ATG AAG AAA GCT        96
Arg Gln Val Thr Phe Ser Lys Arg Arg Ala Gly Leu Met Lys Lys Ala
             20                  25                  30

CAT GAG ATC TCT GTT CTG TGT GAT GCT GAA GTT GCG CTT GTT GTC TTC       144
His Glu Ile Ser Val Leu Cys Asp Ala Glu Val Ala Leu Val Val Phe
         35                  40                  45

TCC CAT AAG GGG AAA CTC TTT GAA TAC CCC ACT GAT TCT TGT ATG GAG       192
Ser His Lys Gly Lys Leu Phe Glu Tyr Pro Thr Asp Ser Cys Met Glu
     50                  55                  60

GAG ATA CTT GAA CGC TAT GAG AGA TAC TCT TAC GCC GAG AGA CAG CTT       240
Glu Ile Leu Glu Arg Tyr Glu Arg Tyr Ser Tyr Ala Glu Arg Gln Leu
 65                  70                  75                  80

ATA GCA CCT GAG TCC GAC TCC AAT ACG AAC TGG TCG ATG GAG TAT AAT       288
Ile Ala Pro Glu Ser Asp Ser Asn Thr Asn Trp Ser Met Glu Tyr Asn
                 85                  90                  95

AGG CTT AAG GCT AAG ATT GAG CTT TTG GAG AGA AAC CAG AGG CAC TAT       336
Arg Leu Lys Ala Lys Ile Glu Leu Leu Glu Arg Asn Gln Arg His Tyr
            100                 105                 110

CTT GGG GAA GAC TTG CAA GCA ATG AGC CCT AAG GAA CTC CAG AAT CTA       384
Leu Gly Glu Asp Leu Gln Ala Met Ser Pro Lys Glu Leu Gln Asn Leu
        115                 120                 125

GAG CAA CAG CTT GAT ACT GCT CTT AAG CAC ATC CGC TCT AGA AAA AAC       432
Glu Gln Gln Leu Asp Thr Ala Leu Lys His Ile Arg Ser Arg Lys Asn
    130                 135                 140

CAA CTT ATG TAC GAC TCC ATC AAT GAG CTC CAA AGA AAG GAG AAA GCC       480
Gln Leu Met Tyr Asp Ser Ile Asn Glu Leu Gln Arg Lys Glu Lys Ala
145                 150                 155                 160

ATA CAG GAA CAA AAC AGC ATG CTT TCC AAG CAG ATT AAG GAG AGG GAA       528
Ile Gln Glu Gln Asn Ser Met Leu Ser Lys Gln Ile Lys Glu Arg Glu
                165                 170                 175

AAC GTT CTT AGG GCG CAA CAA GAG CAA TGG GAC GAG CAG AAC CAT GGC       576
Asn Val Leu Arg Ala Gln Gln Glu Gln Trp Asp Glu Gln Asn His Gly
            180                 185                 190

CAT AAT ATG CCT CCG CCT CCA CCC CCG CAG CAG CAT CAA ATC CAG CAT       624
His Asn Met Pro Pro Pro Pro Pro Pro Gln Gln His Gln Ile Gln His
        195                 200                 205

CCT TAC ATG CTC TCT CAT CAG CCA TCT CCT TTT CTC AAC ATG GGA GGG       672
Pro Tyr Met Leu Ser His Gln Pro Ser Pro Phe Leu Asn Met Gly Gly
    210                 215                 220

CTG TAT CAA GAA GAA GAT CAA ATG GCA ATG AGG AGG AAC GAT CTC GAT       720
Leu Tyr Gln Glu Glu Asp Gln Met Ala Met Arg Arg Asn Asp Leu Asp
225                 230                 235                 240

CTG TCT CTT GAA CCC GTT TAC AAC TGC AAC CTT GGC CGT CGC TGC T         766
Leu Ser Leu Glu Pro Val Tyr Asn Cys Asn Leu Gly Arg Arg Cys
                245                 250                 255

GA                                                                    768
```

(2) INFORMATION FOR SEQ ID NO:6:

(i) SEQUENCE CHARACTERISTICS:

(A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO:6:

Met Gly Arg Gly Arg Val Gln Leu Lys Arg Ile Glu Asn Lys Ile Asn
1               5                   10                  15

Arg Gln Val Thr Phe Ser Lys Arg Arg Ala Gly Leu Met Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Pro Thr Asp Ser Cys Met Glu
    50                  55                  60

Glu Ile Leu Glu Arg Tyr Glu Arg Tyr Ser Tyr Ala Glu Arg Gln Leu
65                  70                  75                  80

Ile Ala Pro Glu Ser Asp Ser Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Ser Arg Lys Asn
130                 135                 140

Gln Leu Met Tyr Asp Ser Ile Asn Glu Leu Gln Arg Lys Glu Lys Ala
145                 150                 155                 160

Ile Gln Glu Gln Asn Ser Met Leu Ser Lys Gln Ile Lys Glu Arg Glu
                165                 170                 175

Asn Val Leu Arg Ala Gln Gln Glu Gln Trp Asp Glu Gln Asn His Gly
            180                 185                 190

His Asn Met Pro Pro Pro Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Glu Asp Gln Met Ala Met Arg Arg Asn Asp Leu Asp
225                 230                 235                 240

Leu Ser Leu Glu Pro Val Tyr Asn Cys Asn Leu Gly Arg Arg Cys
                245                 250                 255

(2) INFORMATION FOR SEQ ID NO:7:

(i) SEQUENCE CHARACTERISTICS:
        (A) LENGTH: 1345 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 149..968

(ix) FEATURE:
        (A) NAME/KEY: misc_feature
        (B) LOCATION: 1..1345
        (D) OTHER INFORMATION: /note= "product = Zea mays AP1."

(xi) SEQUENCE DESCRIPTION: SEQ ID NO:7:

GCACGAGTCC TCCTCCTCCT CGCATCCCAC CCCACCCCAC CTTCTCCTTA AAGCTACCTG      60

-continued

```
CCTACCCGGC GGTTGCGCGC CGCAATCGAT CGACCGGAAG AGAAAGAGCA GCTAGCTAGC         120

TAGCAGATCG AGCACGGCA ACAAGGCG ATG GGG CGC GGC AAG GTA CAG CTG            172
                              Met Gly Arg Gly Lys Val Gln Leu
                               1               5

AAG CGG ATA GAG AAC AAG ATA AAC CGG CAG GTG ACC TTC TCC AAG CGC          220
Lys Arg Ile Glu Asn Lys Ile Asn Arg Gln Val Thr Phe Ser Lys Arg
         10              15                  20

CGG AAC GGC CTG CTC AAG AAG GCG CAC GAG ATC TCC GTC CTC TGC GAT          268
Arg Asn Gly Leu Leu Lys Lys Ala His Glu Ile Ser Val Leu Cys Asp
 25              30                  35                  40

GCC GAG GTC GCC GTC ATC GTC TTC TCC CCC AAG GGC AAG CTC TAC GAG          316
Ala Glu Val Ala Val Ile Val Phe Ser Pro Lys Gly Lys Leu Tyr Glu
                 45                  50                  55

TAC GCC ACC GAC TCC CGC ATG GAC AAA ATT CTT GAA CGC TAT GAG CGA          364
Tyr Ala Thr Asp Ser Arg Met Asp Lys Ile Leu Glu Arg Tyr Glu Arg
             60                  65                  70

TAT TCC TAT GCT GAA AAG GCT CTT ATT TCA GCT GAA TCT GAA AGT GAG          412
Tyr Ser Tyr Ala Glu Lys Ala Leu Ile Ser Ala Glu Ser Glu Ser Glu
         75                  80                  85

GGA AAT TGG TGC CAC GAA TAC AGG AAA CTG AAG GCC AAA ATT GAG ACC          460
Gly Asn Trp Cys His Glu Tyr Arg Lys Leu Lys Ala Lys Ile Glu Thr
 90              95                 100

ATA CAA AAA TGC CAC AAG CAC CTG ATG GGA GAG GAT CTA GAG TCT TTG          508
Ile Gln Lys Cys His Lys His Leu Met Gly Glu Asp Leu Glu Ser Leu
105             110                 115                 120

AAT CCC AAA GAG CTC CAG CAA CTA GAG CAG CAG CTG GAT AGC TCA CTG          556
Asn Pro Lys Glu Leu Gln Gln Leu Glu Gln Gln Leu Asp Ser Ser Leu
            125                 130                 135

AAG CAC ATC AGA TCA AGG AAG AGC CAC CTT ATG GCC GAG TCT ATT TCT          604
Lys His Ile Arg Ser Arg Lys Ser His Leu Met Ala Glu Ser Ile Ser
            140                 145                 150

GAG CTA CAG AAG AAG GAG AGG TCA CTG CAG GAG GAG AAC AAG GCT CTG          652
Glu Leu Gln Lys Lys Glu Arg Ser Leu Gln Glu Glu Asn Lys Ala Leu
            155                 160                 165

CAG AAG GAA CTT GCG GAG AGG CAG AAG GCC GTC GCG AGC CGG CAG CAG          700
Gln Lys Glu Leu Ala Glu Arg Gln Lys Ala Val Ala Ser Arg Gln Gln
            170                 175                 180

CAG CAA CAG CAG CAG GTG CAG TGG GAC CAG CAG ACA CAT GCC CAG GCC          748
Gln Gln Gln Gln Gln Val Gln Trp Asp Gln Gln Thr His Ala Gln Ala
185             190                 195                 200

CAG ACA AGC TCA TCA TCG TCC TCC TTC ATG ATG AGG CAG GAT CAG CAG          796
Gln Thr Ser Ser Ser Ser Ser Phe Met Met Arg Gln Asp Gln Gln
            205                 210                 215

GGA CTG CCG CCT CCA CAC AAC ATC TGC TTC CCG CCG TTG ACA ATG GGA          844
Gly Leu Pro Pro Pro His Asn Ile Cys Phe Pro Pro Leu Thr Met Gly
            220                 225                 230

GAT AGA GGT GAA GAG CTG GCT GCG GCG GCG GCG GCG CAG CAG CAG CAG          892
Asp Arg Gly Glu Glu Leu Ala Ala Ala Ala Ala Ala Gln Gln Gln Gln
            235                 240                 245

CCA CTG CCG GGG CAG GCG CAA CCG CAG CTC CGC ATC GCA GGT CTG CCA          940
Pro Leu Pro Gly Gln Ala Gln Pro Gln Leu Arg Ile Ala Gly Leu Pro
            250                 255                 260

CCA TGG ATG CTG AGC CAC CTC AAT GCA T AAGGAGAGGG TCGATGAACA              988
Pro Trp Met Leu Ser His Leu Asn Ala
265                 270

CATCGACCTC CTCTCTCTCT CTCTCTCGTC ATGGATCATG ACGTACGCGT ACCATATGGT       1048

TGCTGTGCCT GCCCCCATCG ATCGCGAGCA ATGGCACGCT CATGCAAGTG ATCATTGCTC       1108
```

```
CCCGTTGGTT AAACCCTAGC CTATGTTCAT GGCGTCAGCA ACTAAGCTAA ACTATTGTTA    1168

TGTTTGCAAG AAAGGGTAAA CCCGCTAGCT GTGTAATCTT GTCCAGCTAT CAGTATGCTT    1228

GTTACTGCCC AGTTACCCTT GAATCTAGCG GCGCTTTTGG TGAGAGGGTG CAGTTTACTT    1288

TAAACATGGT TCGTGACTTG CTGTAAATAG TAGTATTAAT CGATTTGGGC ATCTAAA      1345
```

(2) INFORMATION FOR SEQ ID NO:8:

(i) SEQUENCE CHARACTERISTICS:
        (A) LENGTH: 273 amino acids
        (B) TYPE: amino acid
        (D) TOPOLOGY: linear (ii) MOLECULE TYPE: protein (xi) SEQUENCE DESCRIPTION: SEQ ID NO:8:

```
Met Gly Arg Gly Lys Val Gln Leu Lys Arg Ile Glu Asn Lys Ile Asn
 1               5                  10                  15

Arg Gln Val Thr Phe Ser Lys Arg Arg Asn Gly Leu Leu Lys Lys Ala
                20                  25                  30

His Glu Ile Ser Val Leu Cys Asp Ala Glu Val Ala Val Ile Val Phe
            35                  40                  45

Ser Pro Lys Gly Lys Leu Tyr Glu Tyr Ala Thr Asp Ser Arg Met Asp
        50                  55                  60

Lys Ile Leu Glu Arg Tyr Glu Arg Tyr Ser Tyr Ala Glu Lys Ala Leu
65                  70                  75                  80

Ile Ser Ala Glu Ser Glu Ser Glu Gly Asn Trp Cys His Glu Tyr Arg
                85                  90                  95

Lys Leu Lys Ala Lys Ile Glu Thr Ile Gln Lys Cys His Lys His Leu
            100                 105                 110

Met Gly Glu Asp Leu Glu Ser Leu Asn Pro Lys Glu Leu Gln Gln Leu
        115                 120                 125

Glu Gln Gln Leu Asp Ser Ser Leu Lys His Ile Arg Ser Arg Lys Ser
    130                 135                 140

His Leu Met Ala Glu Ser Ile Ser Glu Leu Gln Lys Lys Glu Arg Ser
145                 150                 155                 160

Leu Gln Glu Glu Asn Lys Ala Leu Gln Lys Glu Leu Ala Glu Arg Gln
                165                 170                 175

Lys Ala Val Ala Ser Arg Gln Gln Gln Gln Gln Gln Val Gln Trp
            180                 185                 190

Asp Gln Gln Thr His Ala Gln Ala Gln Thr Ser Ser Ser Ser Ser
    195                 200                 205

Phe Met Met Arg Gln Asp Gln Gln Gly Leu Pro Pro His Asn Ile
210                 215                 220

Cys Phe Pro Pro Leu Thr Met Gly Asp Arg Gly Glu Glu Leu Ala Ala
225                 230                 235                 240

Ala Ala Ala Ala Gln Gln Gln Pro Leu Pro Gly Gln Ala Gln Pro
                245                 250                 255

Gln Leu Arg Ile Ala Gly Leu Pro Pro Trp Met Leu Ser His Leu Asn
            260                 265                 270

Ala
```

(2) INFORMATION FOR SEQ ID NO:9:

(i) SEQUENCE CHARACTERISTICS:
        (A) LENGTH: 779 base pairs
        (B) TYPE: nucleic acid (C) STRANDEDNESS: double
        (D) TOPOLOGY: linear (ii) MOLECULE TYPE: cDNA (ix) FEATURE:
        (A) NAME/KEY: CDS
        (B) LOCATION: 10..775

(ix) FEATURE:
        (A) NAME/KEY: unsure
        (B) LOCATION: 778..779
        (D) OTHER INFORMATION: /note= "N = one or more
            nucleotides."

(ix) FEATURE:
        (A) NAME/KEY: misc_feature
        (B) LOCATION: 1..779
        (D) OTHER INFORMATION: /note= "product = Arabidopsis
            thaliana CAL."

(xi) SEQUENCE DESCRIPTION: SEQ ID NO:9:

```
TTAAGAGAA ATG GGA AGG GGT AGG GTT GAA TTG AAG AGG ATA GAG AAC            48
          Met Gly Arg Gly Arg Val Glu Leu Lys Arg Ile Glu Asn
            1               5                  10

AAG ATC AAT AGA CAA GTG ACA TTC TCG AAA AGA AGA ACT GGT CTT TTG          96
Lys Ile Asn Arg Gln Val Thr Phe Ser Lys Arg Arg Thr Gly Leu Leu
 15              20                  25

AAG AAA GCT CAG GAG ATC TCT GTT CTT TGT GAT GCC GAG GTT TCC CTT         144
Lys Lys Ala Gln Glu Ile Ser Val Leu Cys Asp Ala Glu Val Ser Leu
 30              35                  40                  45

ATT GTC TTC TCC CAT AAG GGC AAA TTG TTC GAG TAC TCC TCT GAA TCT         192
Ile Val Phe Ser His Lys Gly Lys Leu Phe Glu Tyr Ser Ser Glu Ser
                 50                  55                  60

TGC ATG GAG AAG GTA CTA GAA CGC TAC GAG AGG TAT TCT TAC GCC GAG         240
Cys Met Glu Lys Val Leu Glu Arg Tyr Glu Arg Tyr Ser Tyr Ala Glu
                 65                  70                  75

AGA CAG CTG ATT GCA CCT GAC TCT CAC GTT AAT GCA CAG ACG AAC TGG         288
Arg Gln Leu Ile Ala Pro Asp Ser His Val Asn Ala Gln Thr Asn Trp
             80                  85                  90

TCA ATG GAG TAT AGC AGG CTT AAG GCC AAG ATT GAG CTT TTG GAG AGA         336
Ser Met Glu Tyr Ser Arg Leu Lys Ala Lys Ile Glu Leu Leu Glu Arg
     95                 100                 105

AAC CAA AGG CAT TAT CTG GGA GAA GAG TTG GAA CCA ATG AGC CTC AAG         384
Asn Gln Arg His Tyr Leu Gly Glu Glu Leu Glu Pro Met Ser Leu Lys
110                 115                 120                 125

GAT CTC CAA AAT CTG GAG CAG CAG CTT GAG ACT GCT CTT AAG CAC ATT         432
Asp Leu Gln Asn Leu Glu Gln Gln Leu Glu Thr Ala Leu Lys His Ile
                130                 135                 140

CGC TCC AGA AAA AAT CAA CTC ATG AAT GAG TCC CTC AAC CAC CTC CAA         480
Arg Ser Arg Lys Asn Gln Leu Met Asn Glu Ser Leu Asn His Leu Gln
                145                 150                 155

AGA AAG GAG AAG GAG ATA CAG GAG GAA AAC AGC ATG CTT ACC AAA CAG         528
Arg Lys Glu Lys Glu Ile Gln Glu Glu Asn Ser Met Leu Thr Lys Gln
            160                 165                 170

ATA AAG GAG AGG GAA AAC ATC CTA AAG ACA AAA CAA ACC CAA TGT GAG         576
Ile Lys Glu Arg Glu Asn Ile Leu Lys Thr Lys Gln Thr Gln Cys Glu
        175                 180                 185

CAG CTG AAC CGC AGC GTC GAC GAT GTA CCA CAG CCA CAA CCA TTT CAA         624
Gln Leu Asn Arg Ser Val Asp Asp Val Pro Gln Pro Gln Pro Phe Gln
190                 195                 200                 205

CAC CCC CAT CTT TAC ATG ATC GCT CAT CAG ACT TCT CCT TTC CTA AAT         672
His Pro His Leu Tyr Met Ile Ala His Gln Thr Ser Pro Phe Leu Asn
                210                 215                 220
```

```
ATG GGT GGT TTG TAC CAA GGA GAA GAC CAA ACG GCG ATG AGG AGG AAC        720
Met Gly Gly Leu Tyr Gln Gly Glu Asp Gln Thr Ala Met Arg Arg Asn
            225                 230                 235

AAT CTG GAT CTG ACT CTT GAA CCC ATT TAC AAT TAC CTT GGC TGT TAC        768
Asn Leu Asp Leu Thr Leu Glu Pro Ile Tyr Asn Tyr Leu Gly Cys Tyr
        240                 245                 250

GCC GCT T GANN                                                         779
Ala Ala
    255
```

(2) INFORMATION FOR SEQ ID NO:10:

(i) SEQUENCE CHARACTERISTICS:
        (A) LENGTH: 255 amino acids
        (B) TYPE: amino acid
        (D) TOPOLOGY: linear (ii) MOLECULE TYPE: protein (xi) SEQUENCE DESCRIPTION: SEQ ID NO:10:

```
Met Gly Arg Gly Arg Val Glu Leu Lys Arg Ile Glu Asn Lys Ile Asn
  1               5                  10                  15

Arg Gln Val Thr Phe Ser Lys Arg Arg Thr Gly Leu Leu Lys Lys Ala
             20                  25                  30

Gln Glu Ile Ser Val Leu Cys Asp Ala Glu Val Ser Leu Ile Val Phe
         35                  40                  45

Ser His Lys Gly Lys Leu Phe Glu Tyr Ser Ser Glu Ser Cys Met Glu
     50                  55                  60

Lys Val Leu Glu Arg Tyr Glu Arg Tyr Ser Tyr Ala Glu Arg Gln Leu
 65                  70                  75                  80

Ile Ala Pro Asp Ser His Val Asn Ala Gln Thr Asn Trp Ser Met Glu
                 85                  90                  95

Tyr Ser Arg Leu Lys Ala Lys Ile Glu Leu Leu Glu Arg Asn Gln Arg
            100                 105                 110

His Tyr Leu Gly Glu Glu Leu Glu Pro Met Ser Leu Lys Asp Leu Gln
        115                 120                 125

Asn Leu Glu Gln Gln Leu Glu Thr Ala Leu Lys His Ile Arg Ser Arg
    130                 135                 140

Lys Asn Gln Leu Met Asn Glu Ser Leu Asn His Leu Gln Arg Lys Glu
145                 150                 155                 160

Lys Glu Ile Gln Glu Glu Asn Ser Met Leu Thr Lys Gln Ile Lys Glu
                165                 170                 175

Arg Glu Asn Ile Leu Lys Thr Lys Gln Thr Gln Cys Glu Gln Leu Asn
            180                 185                 190

Arg Ser Val Asp Asp Val Pro Gln Pro Gln Pro Phe Gln His Pro His
        195                 200                 205

Leu Tyr Met Ile Ala His Gln Thr Ser Pro Phe Leu Asn Met Gly Gly
    210                 215                 220

Leu Tyr Gln Gly Glu Asp Gln Thr Ala Met Arg Arg Asn Asn Leu Asp
225                 230                 235                 240

Leu Thr Leu Glu Pro Ile Tyr Asn Tyr Leu Gly Cys Tyr Ala Ala
                245                 250                 255
```

(2) INFORMATION FOR SEQ ID NO:11:

(i) SEQUENCE CHARACTERISTICS:
        (A) LENGTH: 756 base pairs
        (B) TYPE: nucleic acid
        (C) STRANDEDNESS: double (D) TOPOLOGY: linear (ii) MOLECULE TYPE: cDNA (ix) FEATURE:
    (A) NAME/KEY: CDS
    (B) LOCATION: 1..754

(ix) FEATURE:
    (A) NAME/KEY: misc_feature
    (B) LOCATION: 1..756
    (D) OTHER INFORMATION: /note= "product = Brassica oleracea CAL."

(xi) SEQUENCE DESCRIPTION: SEQ ID NO:11:

```
ATG GGA AGG GGT AGG GTT GAA ATG AAG AGG ATA GAG AAC AAG ATC AAC        48
Met Gly Arg Gly Arg Val Glu Met Lys Arg Ile Glu Asn Lys Ile Asn
 1               5                  10                  15

CGA CAA GTG ACG TTT TCG AAA AGA AGA GCT GGT CTT TTG AAG AAA GCC        96
Arg Gln Val Thr Phe Ser Lys Arg Arg Ala Gly Leu Leu Lys Lys Ala
                20                  25                  30

CAT GAG ATC TCG ATC CTT TGT GAT GCT GAG GTT TCC CTT ATT GTC TTC       144
His Glu Ile Ser Ile Leu Cys Asp Ala Glu Val Ser Leu Ile Val Phe
            35                  40                  45

TCC CAT AAG GGG AAA CTG TTC GAG TAC TCG TCT GAA TCT TGC ATG GAG       192
Ser His Lys Gly Lys Leu Phe Glu Tyr Ser Ser Glu Ser Cys Met Glu
         50                  55                  60

AAG GTA CTA GAA CAC TAC GAG AGG TAC TCT TAC GCC GAG AAA CAG CTA       240
Lys Val Leu Glu His Tyr Glu Arg Tyr Ser Tyr Ala Glu Lys Gln Leu
65                  70                  75                  80

AAA GTT CCA GAC TCT CAC GTC AAT GCA CAA ACG AAC TGG TCA GTG GAA       288
Lys Val Pro Asp Ser His Val Asn Ala Gln Thr Asn Trp Ser Val Glu
                85                  90                  95

TAT AGC AGG CTT AAG GCT AAG ATT GAG CTT TTG GAG AGA AAC CAA AGG       336
Tyr Ser Arg Leu Lys Ala Lys Ile Glu Leu Leu Glu Arg Asn Gln Arg
                100                 105                 110

CAT TAT CTG GGC GAA GAT TTA GAA TCA ATC AGC ATA AAG GAG CTA CAG       384
His Tyr Leu Gly Glu Asp Leu Glu Ser Ile Ser Ile Lys Glu Leu Gln
            115                 120                 125

AAT CTG GAG CAG CAG CTT GAC ACT TCT CTT AAA CAT ATT CGC TCG AGA       432
Asn Leu Glu Gln Gln Leu Asp Thr Ser Leu Lys His Ile Arg Ser Arg
        130                 135                 140

AAA AAT CAA CTA ATG CAC GAG TCC CTC AAC CAC CTC CAA AGA AAG GAG       480
Lys Asn Gln Leu Met His Glu Ser Leu Asn His Leu Gln Arg Lys Glu
145                 150                 155                 160

AAA GAA ATA CTG GAG GAA AAC AGC ATG CTT GCC AAA CAG ATA AGG GAG       528
Lys Glu Ile Leu Glu Glu Asn Ser Met Leu Ala Lys Gln Ile Arg Glu
                165                 170                 175

AGG GAG AGT ATC CTA AGG ACA CAT CAA AAC CAA TCA GAG CAG CAA AAC       576
Arg Glu Ser Ile Leu Arg Thr His Gln Asn Gln Ser Glu Gln Gln Asn
                180                 185                 190

CGC AGC CAC CAT GTA GCT CCT CAG CCG CAA CCG CAG TTA AAT CCT TAC       624
Arg Ser His His Val Ala Pro Gln Pro Gln Pro Gln Leu Asn Pro Tyr
                195                 200                 205

ATG GCA TCA TCT CCT TTC CTA AAT ATG GGT GGC ATG TAC CAA GGA GAA       672
Met Ala Ser Ser Pro Phe Leu Asn Met Gly Gly Met Tyr Gln Gly Glu
210                 215                 220

TAT CCA ACG GCG GTG AGG AGG AAC CGT CTC GAT CTG ACT CTT GAA CCC       720
Tyr Pro Thr Ala Val Arg Arg Asn Arg Leu Asp Leu Thr Leu Glu Pro
225                 230                 235                 240

ATT TAC AAC TGC AAC CTT GGT TAC TTT GCC GCA T GA                      756
Ile Tyr Asn Cys Asn Leu Gly Tyr Phe Ala Ala
                245                 250
```

(2) INFORMATION FOR SEQ ID NO:12:

(i) SEQUENCE CHARACTERISTICS:
        (A) LENGTH: 251 amino acids
        (B) TYPE: amino acid
        (D) TOPOLOGY: linear (ii) MOLECULE TYPE: protein (xi) SEQUENCE DESCRIPTION: SEQ ID NO:12:

```
Met Gly Arg Gly Arg Val Glu Met Lys Arg Ile Glu Asn Lys Ile Asn
 1               5                  10                  15
Arg Gln Val Thr Phe Ser Lys Arg Arg Ala Gly Leu Leu Lys Lys Ala
            20                  25                  30
His Glu Ile Ser Ile Leu Cys Asp Ala Glu Val Ser Leu Ile Val Phe
        35                  40                  45
Ser His Lys Gly Lys Leu Phe Glu Tyr Ser Ser Glu Ser Cys Met Glu
    50                  55                  60
Lys Val Leu Glu His Tyr Glu Arg Tyr Ser Tyr Ala Glu Lys Gln Leu
65                  70                  75                  80
Lys Val Pro Asp Ser His Val Asn Ala Gln Thr Asn Trp Ser Val Glu
                85                  90                  95
Tyr Ser Arg Leu Lys Ala Lys Ile Glu Leu Leu Glu Arg Asn Gln Arg
            100                 105                 110
His Tyr Leu Gly Glu Asp Leu Gly Ser Ile Ser Ile Lys Glu Leu Gln
        115                 120                 125
Asn Leu Glu Gln Gln Leu Asp Thr Ser Leu Lys His Ile Arg Ser Arg
    130                 135                 140
Lys Asn Gln Leu Met His Glu Ser Leu Asn His Leu Gln Arg Lys Glu
145                 150                 155                 160
Lys Glu Ile Leu Glu Glu Asn Ser Met Leu Ala Lys Gln Ile Arg Glu
                165                 170                 175
Arg Glu Ser Ile Leu Arg Thr His Gln Asn Gln Ser Glu Gln Gln Asn
            180                 185                 190
Arg Ser His His Val Ala Pro Gln Pro Gln Pro Gln Leu Asn Pro Tyr
        195                 200                 205
Met Ala Ser Ser Pro Phe Leu Asn Met Gly Gly Met Tyr Gln Gly Glu
    210                 215                 220
Tyr Pro Thr Ala Val Arg Arg Asn Arg Leu Asp Leu Thr Leu Glu Pro
225                 230                 235                 240
Ile Tyr Asn Cys Asn Leu Gly Tyr Phe Ala Ala
                245                 250
```

(2) INFORMATION FOR SEQ ID NO:13:

(i) SEQUENCE CHARACTERISTICS:
        (A) LENGTH: 756 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 1..451

(ix) FEATURE:
        (A) NAME/KEY: misc_feature
        (B) LOCATION: 1..756

(D) OTHER INFORMATION: /note= "product = Brassica oleracea var. botrytis CAL."

(xi) SEQUENCE DESCRIPTION: SEQ ID NO:13:

| | | |
|---|---|---|
| ATG GGA AGG GGT AGG GTT GAA ATG AAG AGG ATA GAG AAC AAG ATC AAC<br>Met Gly Arg Gly Arg Val Glu Met Lys Arg Ile Glu Asn Lys Ile Asn<br>1                       5                       10                    15 | 48 |
| AGA CAA GTG ACG TTT TCG AAA AGA AGA GCT GGT CTT TTG AAG AAA GCC<br>Arg Gln Val Thr Phe Ser Lys Arg Arg Ala Gly Leu Leu Lys Lys Ala<br>                    20                       25                     30 | 96 |
| CAT GAG ATC TCG ATT CTT TGT GAT GCT GAG GTT TCC CTT ATT GTC TTC<br>His Glu Ile Ser Ile Leu Cys Asp Ala Glu Val Ser Leu Ile Val Phe<br>         35                     40                     45 | 144 |
| TCC CAT AAG GGG AAA CTG TTC GAG TAC TCG TCT GAA TCT TGC ATG GAG<br>Ser His Lys Gly Lys Leu Phe Glu Tyr Ser Ser Glu Ser Cys Met Glu<br>50                       55                       60 | 192 |
| AAG GTA CTA GAA CGC TAC GAG AGG TAC TCT TAC GCC GAG AAA CAG CTA<br>Lys Val Leu Glu Arg Tyr Glu Arg Tyr Ser Tyr Ala Glu Lys Gln Leu<br>65                       70                     75                   80 | 240 |
| AAA GCT CCA GAC TCT CAC GTC AAT GCA CAA ACG AAC TGG TCA ATG GAA<br>Lys Ala Pro Asp Ser His Val Asn Ala Gln Thr Asn Trp Ser Met Glu<br>                    85                       90                     95 | 288 |
| TAT AGC AGG CTT AAG GCT AAG ATT GAG CTT TGG GAG AGG AAC CAA AGG<br>Tyr Ser Arg Leu Lys Ala Lys Ile Glu Leu Trp Glu Arg Asn Gln Arg<br>                   100                    105                   110 | 336 |
| CAT TAT CTG GGA GAA GAT TTA GAA TCA ATC AGC ATA AAG GAG CTA CAG<br>His Tyr Leu Gly Glu Asp Leu Glu Ser Ile Ser Ile Lys Glu Leu Gln<br>               115                    120                   125 | 384 |
| AAT CTG GAG CAG CAG CTT GAC ACT TCT CTT AAA CAT ATT CGC TCC AGA<br>Asn Leu Glu Gln Gln Leu Asp Thr Ser Leu Lys His Ile Arg Ser Arg<br>130                       135                   140 | 432 |
| AAA AAT CAA CTA ATG CAC T AGTCCCTCAA CCACCTCCAA AGAAAGGAGA<br>Lys Asn Gln Leu Met His<br>145                     150 | 481 |
| AAGAAATACT GGAGGAAAAC AGCATGCTTG CCAAACAGAT AAAGGAGAGG GAGAGTATCC | 541 |
| TAAGGACACA TCAAAACCAA TCAGAGCAGC AAAACCGCAG CCACCATGTA GCTCCTCAGC | 601 |
| CGCAACCGCA GTTAAATCCT TACATGGCAT CATCTCCTTT CCTAAATATG GGTGGCATGT | 661 |
| ACCAAGGAGA ATATCCAACG GCGGTGAGGA GGAACCGTCT CGATCTGACT CTTGAACCCA | 721 |
| TTTACAACTG CAACCTTGGT TACTTTGCCG CATGA | 756 |

(2) INFORMATION FOR SEQ ID NO:14:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:14:

Met Gly Arg Gly Arg Val Glu Met Lys Arg Ile Glu Asn Lys Ile Asn
1                       5                       10                    15

Arg Gln Val Thr Phe Ser Lys Arg Arg Ala Gly Leu Leu Lys Lys Ala
                    20                       25                     30

His Glu Ile Ser Ile Leu Cys Asp Ala Glu Val Ser Leu Ile Val Phe
         35                     40                     45

Ser His Lys Gly Lys Leu Phe Glu Tyr Ser Ser Glu Ser Cys Met Glu
50                       55                       60

-continued

```
Lys Val Leu Glu Arg Tyr Glu Arg Tyr Ser Tyr Ala Glu Lys Gln Leu
 65                  70                  75                  80

Lys Ala Pro Asp Ser His Val Asn Ala Gln Thr Asn Trp Ser Met Glu
                 85                  90                  95

Tyr Ser Arg Leu Lys Ala Lys Ile Glu Leu Trp Arg Asn Gln Arg
                100                 105                 110

His Tyr Leu Gly Glu Asp Leu Gly Ser Ile Ser Ile Lys Glu Leu Gln
            115                 120                 125

Asn Leu Glu Gln Gln Leu Asp Thr Ser Leu Lys His Ile Arg Ser Arg
130                 135                 140

Lys Asn Gln Leu Met His
145             150

(2) INFORMATION FOR SEQ ID NO:15:

(i) SEQUENCE CHARACTERISTICS:
        (A) LENGTH: 1500 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: CDS
        (B) LOCATION: 72..1343

(ix) FEATURE:
        (A) NAME/KEY: misc_feature
        (B) LOCATION: 1..1500
        (D) OTHER INFORMATION: /note= "product = Arabidopsis
            thaliana LEAFY (LFY)."

(xi) SEQUENCE DESCRIPTION: SEQ ID NO:15:

AAAGCAATCT GCTCAAAAGA GTAAAGAAAG AGAGAAAAAG AGAGTGATAG AGAGAGAGAG      60

AAAAATAGAT T ATG GAT CCT GAA GGT TTC ACG AGT GGC TTA TTC CGG TGG     110
             Met Asp Pro Glu Gly Phe Thr Ser Gly Leu Phe Arg Trp
               1               5                  10

AAC CCA ACG AGA GCA TTG GTT CAA GCA CCA CCT CCG GTT CCA CCT CCG      158
Asn Pro Thr Arg Ala Leu Val Gln Ala Pro Pro Pro Val Pro Pro Pro
         15                  20                  25

CTG CAG CAA CAG CCG GTG ACA CCG CAG ACG GCT GCT TTT GGG ATG CGA      206
Leu Gln Gln Gln Pro Val Thr Pro Gln Thr Ala Ala Phe Gly Met Arg
 30                  35                  40                  45

CTT GGT GGT TTA GAG GGA CTA TTC GGT CCA TAC GGT ATA CGT TTC TAC      254
Leu Gly Gly Leu Glu Gly Leu Phe Gly Pro Tyr Gly Ile Arg Phe Tyr
                 50                  55                  60

ACG GCG GCG AAG ATA GCG GAG TTA GGT TTT ACG GCG AGC ACG CTT GTG      302
Thr Ala Ala Lys Ile Ala Glu Leu Gly Phe Thr Ala Ser Thr Leu Val
             65                  70                  75

GGT ATG AAG GAC GAG GAG CTT GAA GAG ATG ATG AAT AGT CTC TCT CAT      350
Gly Met Lys Asp Glu Glu Leu Glu Glu Met Met Asn Ser Leu Ser His
         80                  85                  90

ATC TTT CGT TGG GAG CTT CTT GTT GGT GAA CGG TAC GGT ATC AAA GCT      398
Ile Phe Arg Trp Glu Leu Leu Val Gly Glu Arg Tyr Gly Ile Lys Ala
     95                 100                 105

GCC GTT AGA GCT GAA CGG AGA CGA TTG CAA GAA GAG GAG GAA GAG GAA      446
Ala Val Arg Ala Glu Arg Arg Arg Leu Gln Glu Glu Glu Glu Glu Glu
110                 115                 120                 125

TCT TCT AGA CGC CGT CAT TTG CTA CTC TCC GCC GCT GGT GAT TCC GGT      494
Ser Ser Arg Arg Arg His Leu Leu Leu Ser Ala Ala Gly Asp Ser Gly
                130                 135                 140
```

```
ACT CAT CAC GCT CTT GAT GCT CTC TCC CAA GAA GAT GAT TGG ACA GGG      542
Thr His His Ala Leu Asp Ala Leu Ser Gln Glu Asp Asp Trp Thr Gly
        145                 150                 155

TTA TCT GAG GAA CCG GTG CAG CAA CAA GAC CAG ACT GAT GCG GCG GGG      590
Leu Ser Glu Glu Pro Val Gln Gln Gln Asp Gln Thr Asp Ala Ala Gly
160                 165                 170

AAT AAC GGC GGA GGA GGA AGT GGT TAC TGG GAC GCA GGT CAA GGA AAG      638
Asn Asn Gly Gly Gly Gly Ser Gly Tyr Trp Asp Ala Gly Gln Gly Lys
        175                 180                 185

ATG AAG AAG CAA CAG CAG CAG AGA CGG AGA AAG AAA CCA ATG CTG ACG      686
Met Lys Lys Gln Gln Gln Gln Arg Arg Arg Lys Lys Pro Met Leu Thr
190                 195                 200                 205

TCA GTG GAA ACC GAC GAA GAC GTC AAC GAA GGT GAG GAT GAC GAC GGG      734
Ser Val Glu Thr Asp Glu Asp Val Asn Glu Gly Glu Asp Asp Asp Gly
            210                 215                 220

ATG GAT AAC GGC AAC GGA GGT AGT GGT TTG GGG ACA GAG AGA CAG AGG      782
Met Asp Asn Gly Asn Gly Gly Ser Gly Leu Gly Thr Glu Arg Gln Arg
                225                 230                 235

GAG CAT CCG TTT ATC GTA ACG GAG CCT GGG GAA GTG GCA CGT GGC AAA      830
Glu His Pro Phe Ile Val Thr Glu Pro Gly Glu Val Ala Arg Gly Lys
                    240                 245                 250

AAG AAC GGC TTA GAT TAT CTG TTC CAC TTG TAC GAA CAA TGC CGT GAG      878
Lys Asn Gly Leu Asp Tyr Leu Phe His Leu Tyr Glu Gln Cys Arg Glu
        255                 260                 265

TTC CTT CTT CAG GTC CAG ACA ATT GCT AAA GAC CGT GGC GAA AAA TGC      926
Phe Leu Leu Gln Val Gln Thr Ile Ala Lys Asp Arg Gly Glu Lys Cys
270                 275                 280                 285

CCC ACC AAG GTG ACG AAC CAA GTA TTC AGG TAC GCG AAG AAA TCA GGA      974
Pro Thr Lys Val Thr Asn Gln Val Phe Arg Tyr Ala Lys Lys Ser Gly
                290                 295                 300

GCG AGT TAC ATA AAC AAG CCT AAA ATG CGA CAC TAC GTT CAC TGT TAC     1022
Ala Ser Tyr Ile Asn Lys Pro Lys Met Arg His Tyr Val His Cys Tyr
                    305                 310                 315

GCT CTC CAC TGC CTA GAC GAA GAA GCT TCA AAT GCT CTC AGA AGA GCG     1070
Ala Leu His Cys Leu Asp Glu Glu Ala Ser Asn Ala Leu Arg Arg Ala
        320                 325                 330

TTT AAA GAA CGC GGT GAG AAC GTT GGC TCA TGG CGT CAG GCT TGT TAC     1118
Phe Lys Glu Arg Gly Glu Asn Val Gly Ser Trp Arg Gln Ala Cys Tyr
335                 340                 345

AAG CCA CTT GTG AAC ATC GCT TGT CGT CAT GGC TGG GAT ATA GAC GCC     1166
Lys Pro Leu Val Asn Ile Ala Cys Arg His Gly Trp Asp Ile Asp Ala
350                 355                 360                 365

GTC TTT AAC GCT CAT CCT CGT CTC TCT ATT TGG TAT GTT CCA ACA AAG     1214
Val Phe Asn Ala His Pro Arg Leu Ser Ile Trp Tyr Val Pro Thr Lys
                370                 375                 380

CTG CGT CAG CTT TGC CAT TTG GAG CGG AAC AAT GCG GTT GCT GCG GCT     1262
Leu Arg Gln Leu Cys His Leu Glu Arg Asn Asn Ala Val Ala Ala Ala
            385                 390                 395

GCG GCT TTA GTT GGC GGT ATT AGC TGT ACC GGA TCG TCG ACG TCT GGA     1310
Ala Ala Leu Val Gly Gly Ile Ser Cys Thr Gly Ser Ser Thr Ser Gly
                400                 405                 410

CGT GGT GGA TGC GGC GGC GAC GAC TTG CGT TTC TAGTTTGGTT TGGGTAGTTG   1363
Arg Gly Gly Cys Gly Gly Asp Asp Leu Arg Phe
        415                 420

TGGTTTGTTT AGTCGTTATC CTAATTAACT ATTAGTCTTT AATTTAGTCT TCTTGGCTAA   1423

TTTATTTTTC TTTTTTTGTC AAAACCTTTA ATTTGTTATG CTAATTTGT TATACACGCA    1483

GTTTTCTTAA TGCGTTA                                                  1500
```

(2) INFORMATION FOR SEQ ID NO:16:

(i) SEQUENCE CHARACTERISTICS:
        (A) LENGTH: 424 amino acids
        (B) TYPE: amino acid
        (D) TOPOLOGY: linear (ii) MOLECULE TYPE: protein (xi) SEQUENCE DESCRIPTION: SEQ ID NO:16:

```
Met Asp Pro Glu Gly Phe Thr Ser Gly Leu Phe Arg Trp Asn Pro Thr
  1               5                  10                  15

Arg Ala Leu Val Gln Ala Pro Pro Val Pro Pro Leu Gln Gln
             20                  25                  30

Gln Pro Val Thr Pro Gln Thr Ala Ala Phe Gly Met Arg Leu Gly Gly
             35                  40                  45

Leu Glu Gly Leu Phe Gly Pro Tyr Gly Ile Arg Phe Tyr Thr Ala Ala
             50                  55                  60

Lys Ile Ala Glu Leu Gly Phe Thr Ala Ser Thr Leu Val Gly Met Lys
 65                  70                  75                  80

Asp Glu Glu Leu Glu Met Met Asn Ser Leu Ser His Ile Phe Arg
                 85                  90                  95

Trp Glu Leu Leu Val Gly Glu Arg Tyr Gly Ile Lys Ala Ala Val Arg
                100                 105                 110

Ala Glu Arg Arg Arg Leu Gln Glu Glu Glu Glu Ser Ser Arg
            115                 120                 125

Arg Arg His Leu Leu Leu Ser Ala Ala Gly Asp Ser Gly Thr His His
    130                 135                 140

Ala Leu Asp Ala Leu Ser Gln Glu Asp Asp Trp Thr Gly Leu Ser Glu
145                 150                 155                 160

Glu Pro Val Gln Gln Gln Asp Gln Thr Asp Ala Ala Gly Asn Asn Gly
                165                 170                 175

Gly Gly Gly Ser Gly Tyr Trp Asp Ala Gly Gln Gly Lys Met Lys Lys
                180                 185                 190

Gln Gln Gln Gln Arg Arg Arg Lys Lys Pro Met Leu Thr Ser Val Glu
            195                 200                 205

Thr Asp Glu Asp Val Asn Glu Gly Glu Asp Asp Gly Met Asp Asn
210                 215                 220

Gly Asn Gly Gly Ser Gly Leu Gly Thr Glu Arg Gln Arg Glu His Pro
225                 230                 235                 240

Phe Ile Val Thr Glu Pro Gly Glu Val Ala Arg Gly Lys Lys Asn Gly
                245                 250                 255

Leu Asp Tyr Leu Phe His Leu Tyr Glu Gln Cys Arg Glu Phe Leu Leu
            260                 265                 270

Gln Val Gln Thr Ile Ala Lys Asp Arg Gly Glu Lys Cys Pro Thr Lys
    275                 280                 285

Val Thr Asn Gln Val Phe Arg Tyr Ala Lys Lys Ser Gly Ala Ser Tyr
290                 295                 300

Ile Asn Lys Pro Lys Met Arg His Tyr Val His Cys Tyr Ala Leu His
305                 310                 315                 320

Cys Leu Asp Glu Glu Ala Ser Asn Ala Leu Arg Arg Ala Phe Lys Glu
                325                 330                 335

Arg Gly Glu Asn Val Gly Ser Trp Arg Gln Ala Cys Tyr Lys Pro Leu
            340                 345                 350

Val Asn Ile Ala Cys Arg His Gly Trp Asp Ile Asp Ala Val Phe Asn
355                 360                 365
```

```
Ala His Pro Arg Leu Ser Ile Trp Tyr Val Pro Thr Lys Leu Arg Gln
    370                 375                 380

Leu Cys His Leu Glu Arg Asn Asn Ala Val Ala Ala Ala Ala Ala Leu
385                 390                 395                 400

Val Gly Gly Ile Ser Cys Thr Gly Ser Ser Thr Ser Gly Arg Gly Gly
                405                 410                 415

Cys Gly Gly Asp Asp Leu Arg Phe
            420
```

(2) INFORMATION FOR SEQ ID NO:17:

(i) SEQUENCE CHARACTERISTICS:
        (A) LENGTH: 1656 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..1651

(ix) FEATURE:
        (A) NAME/KEY: misc_feature
        (B) LOCATION: 1..1656
        (D) OTHER INFORMATION: /note= "domain = ecdysone receptor
            ligand binding domain."

(xi) SEQUENCE DESCRIPTION: SEQ ID NO:17:

```
ATG CGG CCG GAA TGC GTC GTC CCG GAG AAC CAA TGT GCG ATG AAG CGG      48
Met Arg Pro Glu Cys Val Val Pro Glu Asn Gln Cys Ala Met Lys Arg
  1               5                  10                  15

CGC GAA AAG AAG GCC CAG AAG GAG AAG GAC AAA ATG ACC ACT TCG CCG      96
Arg Glu Lys Lys Ala Gln Lys Glu Lys Asp Lys Met Thr Thr Ser Pro
                 20                  25                  30

AGC TCT CAG CAT GGC GGC AAT GGC AGC TTG GCC TCT GGT GGC GGC CAA     144
Ser Ser Gln His Gly Gly Asn Gly Ser Leu Ala Ser Gly Gly Gly Gln
             35                  40                  45

GAC TTT GTT AAG AAG GAG ATT CTT GAC CTT ATG ACA TGC GAG CCG CCC     192
Asp Phe Val Lys Lys Glu Ile Leu Asp Leu Met Thr Cys Glu Pro Pro
 50                  55                  60

CAG CAT GCC ACT ATT CCG CTA CTA CCT GAT GAA ATA TTG GCC AAG TGT     240
Gln His Ala Thr Ile Pro Leu Leu Pro Asp Glu Ile Leu Ala Lys Cys
 65                  70                  75                  80

CAA GCG CGC AAT ATA CCT TCC TTA ACG TAC AAT CAG TTG GCC GTT ATA     288
Gln Ala Arg Asn Ile Pro Ser Leu Thr Tyr Asn Gln Leu Ala Val Ile
                 85                  90                  95

TAC AAG TTA ATT TGG TAC CAG GAT GGC TAT GAG CAG CCA TCT GAA GAG     336
Tyr Lys Leu Ile Trp Tyr Gln Asp Gly Tyr Glu Gln Pro Ser Glu Glu
            100                 105                 110

GAT CTC AGG CGT ATA ATG AGT CAA CCC GAT GAG AAC GAG AGC CAA ACG     384
Asp Leu Arg Arg Ile Met Ser Gln Pro Asp Glu Asn Glu Ser Gln Thr
        115                 120                 125

GAC GTC AGC TTT CGG CAT ATA ACC GAG ATA ACC ATA CTC ACG GTC CAG     432
Asp Val Ser Phe Arg His Ile Thr Glu Ile Thr Ile Leu Thr Val Gln
    130                 135                 140

TTG ATT GTT GAG TTT GCT AAA GGT CTA CCA GCG TTT ACA AAG ATA CCC     480
Leu Ile Val Glu Phe Ala Lys Gly Leu Pro Ala Phe Thr Lys Ile Pro
145                 150                 155                 160

CAG GAG GAC CAG ATC ACG TTA CTA AAG GCC TGC TCG TCG GAG GTG ATG     528
Gln Glu Asp Gln Ile Thr Leu Leu Lys Ala Cys Ser Ser Glu Val Met
                165                 170                 175

ATG CTG CGT ATG GCA CGA CGC TAT GAC CAC AGC TCG GAC TCA ATA TTC     576
```

```
          Met Leu Arg Met Ala Arg Arg Tyr Asp His Ser Ser Asp Ser Ile Phe
                      180                 185                 190

TTC GCG AAT AAT AGA TCA TAT ACG CGG GAT TCT TAC AAA ATG GCC GGA           624
Phe Ala Asn Asn Arg Ser Tyr Thr Arg Asp Ser Tyr Lys Met Ala Gly
        195                 200                 205

ATG GCT GAT AAC ATT GAA GAC CTG CTG CAT TTC TGC CGC CAA ATG TTC           672
Met Ala Asp Asn Ile Glu Asp Leu Leu His Phe Cys Arg Gln Met Phe
        210                 215                 220

TCG ATG AAG GTG GAC AAC GTC GAA TAC GCG CTT CTC ACT GCC ATT GTG           720
Ser Met Lys Val Asp Asn Val Glu Tyr Ala Leu Leu Thr Ala Ile Val
225                 230                 235                 240

ATC TTC TCG GAC CGG CCG GGC CTG GAG AAG GCC CAA CTA GTC GAA GCG           768
Ile Phe Ser Asp Arg Pro Gly Leu Glu Lys Ala Gln Leu Val Glu Ala
                245                 250                 255

ATC CAG AGC TAC TAC ATC GAC ACG CTA CGC ATT TAT ATA CTC AAC CGC           816
Ile Gln Ser Tyr Tyr Ile Asp Thr Leu Arg Ile Tyr Ile Leu Asn Arg
            260                 265                 270

CAC TGC GGC GAC TCA ATG AGC CTC GTC TTC TAC GCA AAG CTG CTC TCG           864
His Cys Gly Asp Ser Met Ser Leu Val Phe Tyr Ala Lys Leu Leu Ser
                275                 280                 285

ATC CTC ACC GAG CTG CGT ACG CTG GGC AAC CAG AAC GCC GAG ATG TGT           912
Ile Leu Thr Glu Leu Arg Thr Leu Gly Asn Gln Asn Ala Glu Met Cys
        290                 295                 300

TTC TCA CTA AAG CTC AAA AAC CGC AAA CTG CCC AAG TTC CTC GAG GAG           960
Phe Ser Leu Lys Leu Lys Asn Arg Lys Leu Pro Lys Phe Leu Glu Glu
305                 310                 315                 320

ATC TGG GAC GTT CAT GCC ATC CCG CCA TCG GTC CAG TCG CAC CTT CAG          1008
Ile Trp Asp Val His Ala Ile Pro Pro Ser Val Gln Ser His Leu Gln
                325                 330                 335

ATT ACC CAG GAG GAG AAC GAG CGT CTC GAG CGG GCT GAG CGT ATG CGG          1056
Ile Thr Gln Glu Glu Asn Glu Arg Leu Glu Arg Ala Glu Arg Met Arg
            340                 345                 350

GCA TCG GTT GGG GGC GCC ATT ACC GCC GGC ATT GAT TGC GAC TCT GCC          1104
Ala Ser Val Gly Gly Ala Ile Thr Ala Gly Ile Asp Cys Asp Ser Ala
                355                 360                 365

TCC ACT TCG GCG GCG GCA GCC GCG GCC CAG CAT CAG CCT CAG CCT CAG          1152
Ser Thr Ser Ala Ala Ala Ala Ala Gln His Gln Pro Gln Pro Gln
        370                 375                 380

CCC CAG CCC CAA CCC TCC TCC CTG ACC CAG AAC GAT TCC CAG CAC CAG          1200
Pro Gln Pro Gln Pro Ser Ser Leu Thr Gln Asn Asp Ser Gln His Gln
385                 390                 395                 400

ACA CAG CCG CAG CTA CAA CCT CAG CTA CCA CCT CAG CTG CAA GGT CAA          1248
Thr Gln Pro Gln Leu Gln Pro Gln Leu Pro Pro Gln Leu Gln Gly Gln
                405                 410                 415

CTG CAA CCC CAG CTC CAA CCA CAG CTT CAG ACG CAA CTC CAG CCA CAG          1296
Leu Gln Pro Gln Leu Gln Pro Gln Leu Gln Thr Gln Leu Gln Pro Gln
                420                 425                 430

ATT CAA CCA CAG CCA CAG CTC CTT CCC GTC TCC GCT CCC GTG CCC GCC          1344
Ile Gln Pro Gln Pro Gln Leu Leu Pro Val Ser Ala Pro Val Pro Ala
                435                 440                 445

TCC GTA ACC GCA CCT GGT TCC TTG TCC GCG GTC AGT ACG AGC AGC GAA          1392
Ser Val Thr Ala Pro Gly Ser Leu Ser Ala Val Ser Thr Ser Ser Glu
        450                 455                 460

TAC ATG GGC GGA AGT GCG GCC ATA GGA CCC ATC ACG CCG GCA ACC ACC          1440
Tyr Met Gly Gly Ser Ala Ala Ile Gly Pro Ile Thr Pro Ala Thr Thr
465                 470                 475                 480

AGC AGT ATC ACG GCT GCC GTT ACC GCT AGC TCC ACC ACA TCA GCG GTA          1488
Ser Ser Ile Thr Ala Ala Val Thr Ala Ser Ser Thr Thr Ser Ala Val
                485                 490                 495
```

```
CCG ATG GGC AAC GGA GTT GGA GTC GGT GTT GGG GTG GGC GGC AAC GTC        1536
Pro Met Gly Asn Gly Val Gly Val Gly Val Gly Val Gly Gly Asn Val
        500                 505                 510

AGC ATG TAT GCG AAC GCC CAG ACG GCG ATG GCC TTG ATG GGT GTA GCC        1584
Ser Met Tyr Ala Asn Ala Gln Thr Ala Met Ala Leu Met Gly Val Ala
        515                 520                 525

CTG CAT TCG CAC CAA GAG CAG CTT ATC GGG GGA GTG GCG GTT AAG TCG        1632
Leu His Ser His Gln Glu Gln Leu Ile Gly Gly Val Ala Val Lys Ser
530                 535                 540

GAG CAC TCG ACG ACT GCA T AGCAG                                        1656
Glu His Ser Thr Thr Ala
545                 550
```

(2) INFORMATION FOR SEQ ID NO:18:

(i) SEQUENCE CHARACTERISTICS:
        (A) LENGTH: 550 amino acids
        (B) TYPE: amino acid
        (D) TOPOLOGY: linear (ii) MOLECULE TYPE: protein (xi) SEQUENCE DESCRIPTION: SEQ ID NO:18:

```
Met Arg Pro Glu Cys Val Val Pro Glu Asn Gln Cys Ala Met Lys Arg
1               5                   10                  15

Arg Glu Lys Lys Ala Gln Lys Glu Lys Asp Lys Met Thr Thr Ser Pro
            20                  25                  30

Ser Ser Gln His Gly Gly Asn Gly Ser Leu Ala Ser Gly Gly Gly Gln
        35                  40                  45

Asp Phe Val Lys Lys Glu Ile Leu Asp Leu Met Thr Cys Glu Pro Pro
    50                  55                  60

Gln His Ala Thr Ile Pro Leu Leu Pro Asp Glu Ile Leu Ala Lys Cys
65                  70                  75                  80

Gln Ala Arg Asn Ile Pro Ser Leu Thr Tyr Asn Gln Leu Ala Val Ile
                85                  90                  95

Tyr Lys Leu Ile Trp Tyr Gln Asp Gly Tyr Glu Gln Pro Ser Glu Glu
            100                 105                 110

Asp Leu Arg Arg Ile Met Ser Gln Pro Asp Glu Asn Glu Ser Gln Thr
        115                 120                 125

Asp Val Ser Phe Arg His Ile Thr Glu Ile Thr Ile Leu Thr Val Gln
    130                 135                 140

Leu Ile Val Glu Phe Ala Lys Gly Leu Pro Ala Phe Thr Lys Ile Pro
145                 150                 155                 160

Gln Glu Asp Gln Ile Thr Leu Leu Lys Ala Cys Ser Ser Glu Val Met
                165                 170                 175

Met Leu Arg Met Ala Arg Arg Tyr Asp His Ser Ser Asp Ser Ile Phe
            180                 185                 190

Phe Ala Asn Asn Arg Ser Tyr Thr Arg Asp Ser Tyr Lys Met Ala Gly
        195                 200                 205

Met Ala Asp Asn Ile Glu Asp Leu Leu His Phe Cys Arg Gln Met Phe
    210                 215                 220

Ser Met Lys Val Asp Asn Val Glu Tyr Ala Leu Leu Thr Ala Ile Val
225                 230                 235                 240

Ile Phe Ser Asp Arg Pro Gly Leu Glu Lys Ala Gln Leu Val Glu Ala
                245                 250                 255

Ile Gln Ser Tyr Tyr Ile Asp Thr Leu Arg Ile Tyr Ile Leu Asn Arg
            260                 265                 270
```

```
His Cys Gly Asp Ser Met Ser Leu Val Phe Tyr Ala Lys Leu Leu Ser
        275                 280                 285

Ile Leu Thr Glu Leu Arg Thr Leu Gly Asn Gln Asn Ala Glu Met Cys
        290                 295                 300

Phe Ser Leu Lys Leu Lys Asn Arg Lys Leu Pro Lys Phe Leu Glu Glu
305                 310                 315                 320

Ile Trp Asp Val His Ala Ile Pro Pro Ser Val Gln Ser His Leu Gln
                325                 330                 335

Ile Thr Gln Glu Glu Asn Glu Arg Leu Glu Arg Ala Glu Arg Met Arg
            340                 345                 350

Ala Ser Val Gly Gly Ala Ile Thr Ala Gly Ile Asp Cys Asp Ser Ala
        355                 360                 365

Ser Thr Ser Ala Ala Ala Ala Ala Gln His Gln Pro Gln Pro Gln
        370                 375                 380

Pro Gln Pro Gln Pro Ser Ser Leu Thr Gln Asn Asp Ser Gln His Gln
385                 390                 395                 400

Thr Gln Pro Gln Leu Gln Pro Gln Leu Pro Pro Gln Leu Gln Gly Gln
                405                 410                 415

Leu Gln Pro Gln Leu Gln Pro Gln Leu Gln Thr Gln Leu Gln Pro Gln
            420                 425                 430

Ile Gln Pro Gln Pro Gln Leu Leu Pro Val Ser Ala Pro Val Pro Ala
        435                 440                 445

Ser Val Thr Ala Pro Gly Ser Leu Ser Ala Val Ser Thr Ser Ser Glu
450                 455                 460

Tyr Met Gly Gly Ser Ala Ala Ile Gly Pro Ile Thr Pro Ala Thr Thr
465                 470                 475                 480

Ser Ser Ile Thr Ala Ala Val Thr Ala Ser Ser Thr Thr Ser Ala Val
                485                 490                 495

Pro Met Gly Asn Gly Val Gly Val Gly Val Gly Val Gly Gly Asn Val
            500                 505                 510

Ser Met Tyr Ala Asn Ala Gln Thr Ala Met Ala Leu Met Gly Val Ala
        515                 520                 525

Leu His Ser His Gln Glu Gln Leu Ile Gly Gly Val Ala Val Lys Ser
        530                 535                 540

Glu His Ser Thr Thr Ala
545                 550

(2) INFORMATION FOR SEQ ID NO:19:

(i) SEQUENCE CHARACTERISTICS:
        (A) LENGTH: 855 base pairs
        (B) TYPE: nucleic acid
        (C) STRANDEDNESS: double
        (D) TOPOLOGY: linear (ix) FEATURE:
        (A) NAME/KEY: CDS
        (B) LOCATION: 1..853

(ix) FEATURE:
        (A) NAME/KEY: misc_feature
        (B) LOCATION: 1..855
        (D) OTHER INFORMATION: /note= "domain = glucocorticoid
            receptor ligand binding domain."

(xi) SEQUENCE DESCRIPTION: SEQ ID NO:19:

ACA AAG AAA AAA ATC AAA GGG ATT CAG CAA GCC ACT GCA GGA GTC TCA      48
Thr Lys Lys Lys Ile Lys Gly Ile Gln Gln Ala Thr Ala Gly Val Ser
 1               5                  10                  15
```

```
CAA GAC ACT TCG GAA AAT CCT AAC AAA ACA ATA GTT CCT GCA GCA TTA        96
Gln Asp Thr Ser Glu Asn Pro Asn Lys Thr Ile Val Pro Ala Ala Leu
             20                  25                  30

CCA CAG CTC ACC CCT ACC TTG GTG TCA CTG CTG GAG GTG ATT GAA CCC       144
Pro Gln Leu Thr Pro Thr Leu Val Ser Leu Leu Glu Val Ile Glu Pro
         35                  40                  45

GAG GTG TTG TAT GCA GGA TAT GAT AGC TCT GTT CCA GAT TCA GCA TGG       192
Glu Val Leu Tyr Ala Gly Tyr Asp Ser Ser Val Pro Asp Ser Ala Trp
     50                  55                  60

AGA ATT ATG ACC ACA CTC AAC ATG TTA GGT GGG CGT CAA GTG ATT GCA       240
Arg Ile Met Thr Thr Leu Asn Met Leu Gly Gly Arg Gln Val Ile Ala
 65                  70                  75                  80

GCA GTG AAA TGG GCA AAG GCG ATA CTA GGC TTG AGA AAC TTA CAC CTC       288
Ala Val Lys Trp Ala Lys Ala Ile Leu Gly Leu Arg Asn Leu His Leu
                 85                  90                  95

GAT GAC CAA ATG ACC CTG CTA CAG TAC TCA TGG ATG TTT CTC ATG GCA       336
Asp Asp Gln Met Thr Leu Leu Gln Tyr Ser Trp Met Phe Leu Met Ala
                100                 105                 110

TTT GCC TTG GGT TGG AGA TCA TAC AGA CAA TCA AGC GGA AAC CTG CTC       384
Phe Ala Leu Gly Trp Arg Ser Tyr Arg Gln Ser Ser Gly Asn Leu Leu
            115                 120                 125

TGC TTT GCT CCT GAT CTG ATT ATT AAT GAG CAG AGA ATG TCT CTA CCC       432
Cys Phe Ala Pro Asp Leu Ile Ile Asn Glu Gln Arg Met Ser Leu Pro
        130                 135                 140

TGC ATG TAT GAC CAA TGT AAA CAC ATG CTG TTT GTC TCC TCT GAA TTA       480
Cys Met Tyr Asp Gln Cys Lys His Met Leu Phe Val Ser Ser Glu Leu
145                 150                 155                 160

CAA AGA TTG CAG GTA TCC TAT GAA GAG TAT CTC TGT ATG AAA ACC TTA       528
Gln Arg Leu Gln Val Ser Tyr Glu Glu Tyr Leu Cys Met Lys Thr Leu
                165                 170                 175

CTG CTT CTC TCC TCA GTT GCT AAG GAA GGT CTG AAG AGC CAA GAG TTA       576
Leu Leu Leu Ser Ser Val Ala Lys Glu Gly Leu Lys Ser Gln Glu Leu
            180                 185                 190

TTT GAT GAG ATT CGA ATG ACT TAT ATC AAA GAG CTA GGA AAA GCC ATC       624
Phe Asp Glu Ile Arg Met Thr Tyr Ile Lys Glu Leu Gly Lys Ala Ile
        195                 200                 205

GTC AAA AGG GAA GGG AAC TCC AGT CAG AAC TGG CAA CGG TTT TAC CAA       672
Val Lys Arg Glu Gly Asn Ser Ser Gln Asn Trp Gln Arg Phe Tyr Gln
    210                 215                 220

CTG ACA AAG CTT CTG GAC TCC ATG CAT GAG GTG GTT GAG AAT CTC CTT       720
Leu Thr Lys Leu Leu Asp Ser Met His Glu Val Val Glu Asn Leu Leu
225                 230                 235                 240

ACC TAC TGC TTC CAG ACA TTT TTG GAT AAG ACC ATG AGT ATT GAA TTC       768
Thr Tyr Cys Phe Gln Thr Phe Leu Asp Lys Thr Met Ser Ile Glu Phe
                245                 250                 255

CCA GAG ATG TTA GCT GAA ATC ATC ACT AAT CAG ATA CCA AAA TAT TCA       816
Pro Glu Met Leu Ala Glu Ile Ile Thr Asn Gln Ile Pro Lys Tyr Ser
            260                 265                 270

AAT GGA AAT ATC AAA AAG CTT CTG TTT CAT CAA AAA T GA                  855
Asn Gly Asn Ile Lys Lys Leu Leu Phe His Gln Lys
        275                 280
```

(2) INFORMATION FOR SEQ ID NO:20:

(i) SEQUENCE CHARACTERISTICS:
        (A) LENGTH: 284 amino acids
        (B) TYPE: amino acid
        (D) TOPOLOGY: linear (ii) MOLECULE TYPE: protein (xi) SEQUENCE DESCRIPTION: SEQ ID NO:20:

```
Thr Lys Lys Lys Ile Lys Gly Ile Gln Gln Ala Thr Ala Gly Val Ser
 1               5                  10                  15

Gln Asp Thr Ser Glu Asn Pro Asn Lys Thr Ile Val Pro Ala Ala Leu
                20                  25                  30

Pro Gln Leu Thr Pro Thr Leu Val Ser Leu Leu Glu Val Ile Glu Pro
            35                  40                  45

Glu Val Leu Tyr Ala Gly Tyr Asp Ser Ser Val Pro Asp Ser Ala Trp
 50                  55                  60

Arg Ile Met Thr Thr Leu Asn Met Leu Gly Arg Gln Val Ile Ala
 65                  70                  75                  80

Ala Val Lys Trp Ala Lys Ala Ile Leu Gly Leu Arg Asn Leu His Leu
                85                  90                  95

Asp Asp Gln Met Thr Leu Leu Gln Tyr Ser Trp Met Phe Leu Met Ala
                100                 105                 110

Phe Ala Leu Gly Trp Arg Ser Tyr Arg Gln Ser Ser Gly Asn Leu Leu
            115                 120                 125

Cys Phe Ala Pro Asp Leu Ile Ile Asn Glu Gln Arg Met Ser Leu Pro
    130                 135                 140

Cys Met Tyr Asp Gln Cys Lys His Met Leu Phe Val Ser Ser Glu Leu
145                 150                 155                 160

Gln Arg Leu Gln Val Ser Tyr Glu Glu Tyr Leu Cys Met Lys Thr Leu
                165                 170                 175

Leu Leu Leu Ser Ser Val Ala Lys Glu Gly Leu Lys Ser Gln Glu Leu
            180                 185                 190

Phe Asp Glu Ile Arg Met Thr Tyr Ile Lys Glu Leu Gly Lys Ala Ile
        195                 200                 205

Val Lys Arg Glu Gly Asn Ser Ser Gln Asn Trp Gln Arg Phe Tyr Gln
210                 215                 220

Leu Thr Lys Leu Leu Asp Ser Met His Glu Val Val Glu Asn Leu Leu
225                 230                 235                 240

Thr Tyr Cys Phe Gln Thr Phe Leu Asp Lys Thr Met Ser Ile Glu Phe
                245                 250                 255

Pro Glu Met Leu Ala Glu Ile Ile Thr Asn Gln Ile Pro Lys Tyr Ser
            260                 265                 270

Asn Gly Asn Ile Lys Lys Leu Leu Phe His Gln Lys
            275                 280
```

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ix) FEATURE:
        (A) NAME/KEY: misc_feature
        (B) LOCATION: 1..50
        (D) OTHER INFORMATION: /note= "element = copper inducible
            regulatory element (ACE1 binding site)."

(xi) SEQUENCE DESCRIPTION: SEQ ID NO:21:

AGCTTAGCGA TGCGTCTTTT CCGCTGAACC GTTCCAGCAA AAAAGACTAG      50

(2) INFORMATION FOR SEQ ID NO:22:

(i) SEQUENCE CHARACTERISTICS:
        (A) LENGTH: 19 base pairs (B) TYPE: nucleic acid
        (C) STRANDEDNESS: double
        (D) TOPOLOGY: linear (ix) FEATURE:
        (A) NAME/KEY: misc_feature
        (B) LOCATION: 1..19
        (D) OTHER INFORMATION: /note= "element = tet operator."

(xi) SEQUENCE DESCRIPTION: SEQ ID NO:22:

ACTCTATCAG TGATAGAGT                                                    19

(2) INFORMATION FOR SEQ ID NO:23:

(i) SEQUENCE CHARACTERISTICS:
        (A) LENGTH: 29 base pairs
        (B) TYPE: nucleic acid
        (C) STRANDEDNESS: double
        (D) TOPOLOGY: linear (ix) FEATURE:
        (A) NAME/KEY: misc_feature
        (B) LOCATION: 1..29
        (D) OTHER INFORMATION: /note= "element = ecdysone response
             element."

(xi) SEQUENCE DESCRIPTION: SEQ ID NO:23:

GATCCGACAA GGGTTCAATG CACTTGTCA                                         29

(2) INFORMATION FOR SEQ ID NO:24:

(i) SEQUENCE CHARACTERISTICS:
        (A) LENGTH: 371 base pairs
        (B) TYPE: nucleic acid
        (C) STRANDEDNESS: double
        (D) TOPOLOGY: linear (ix) FEATURE:
        (A) NAME/KEY: misc_feature
        (B) LOCATION: 1..371
        (D) OTHER INFORMATION: /note= "element = heat shock
             inducible regulatory element (HSP81-1 promoter)."

(xi) SEQUENCE DESCRIPTION: SEQ ID NO:24:

GTGGAGTCTC GAAACGAAAA GAACTTTCTG GAATTCGTTT GCTCACAAAG CTAAAAACGG        60

TTGATTTCAT CGAAATACGG CGTCGTTTTC AAAGAACAAT CCAGAAATCA CTGGTTTTCC       120

TTTATTTCAA AAGAAGAGAC TAGAACTTTA TTTCTCCTCT ATAAAATCAC TTTGTTTTTC       180

CCTCTCTTCT TCATAAATCA ACAAAACAAT CACAAATCTC TCGAAACGCT CTCGAAGTTC       240

CAAATTTTCT CTTAGCATTC TCTTTCGTTT CTCGTTTGCG TTGAATCAAA GTTCGTTGCG       300

ATGGCGGATG TTCAGATGGC TGATGCAGAG ACTTTTGCTT TCCAAGCTGA GATTAACCAG       360

CTTCTTAGCT T                                                           371

(2) INFORMATION FOR SEQ ID NO:25:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (xi) SEQUENCE DESCRIPTION: SEQ ID NO:25:

GGATCCGGAT CAAAAATGGG AAGGGGTAG                                         29

(2) INFORMATION FOR SEQ ID NO:26:

-continued

```
    (i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:26:

GGATCCGCTG CGGCGAAGCA GCCAAGGTTG                                          30
```

SEED PLANTS EXHIBITING EARLY REPRODUCTIVE DEVELOPMENT AND METHODS OF MAKING SAME

This work was supported by grant DCB-9018749 awarded by the National Science Foundation and by grant USDA 93-37304 awarded by the United States Department of Agriculture. The United States Government has certain rights in this invention.

BACKGROUND OF THE INVENTION

1. Field of the Invention

This invention relates generally to the field of plant genetic engineering and more specifically to genes involved in the regulation of plant reproductive development.

2. Background Information

A flower is the reproductive structure of a flowering plant. Following fertilization, the ovary of the flower becomes a fruit and bears seeds. As a practical consequence, production of fruit and seed-derived crops such as grapes, beans, corn, wheat, rice and hops is dependent upon flowering.

Early in the life cycle of a flowering plant, vegetative growth occurs, and roots, stems and leaves are formed. During the later period of reproductive growth, flowers as well as new shoots or branches develop. However, the factors responsible for the transition from vegetative to reproductive growth, and the onset of flowering, are poorly understood.

A variety of external signals, such as length of daylight and temperature, affect the time of flowering. The time of flowering also is subject to genetic controls that prevent young plants from flowering prematurely. Thus, the pattern of genes expressed in a plant is an important determinant of the time of flowering.

Given these external signals and genetic controls, a relatively fixed period of vegetative growth precedes flowering in a particular plant species. The length of time required for a crop to mature to flowering limits the geographic location in which it can be grown and can be an important determinant of yield. In addition, since the time of flowering determines when a plant is reproductively mature, the pace of a plant breeding program also depends upon the length of time required for a plant to flower.

Traditionally, plant breeding involves generating hybrids of existing plants, which are examined for improved yield or quality. The improvement of existing plant crops through plant breeding is central to increasing the amount of food grown in the world since the amount of land suitable for agriculture is limited. For example, the development of new strains of wheat, corn and rice through plant breeding has increased the yield of these crops grown in underdeveloped countries such as Mexico, India and Pakistan. Unfortunately, plant breeding is inherently a slow process since plants must be reproductively mature before selective breeding can proceed.

For some plant species, the length of time needed to mature to flowering is so long that selective breeding, which requires several rounds of backcrossing progeny plants with their parents, is impractical. For example, perennial trees such as walnut, hickory, oak, maple and cherry do not flower for several years after planting. As a result, breeding of such plant species for insect or disease-resistance or to produce improved wood or fruit, for example, would require decades, even if only a few rounds of selection were performed.

Methods of promoting early reproductive development can make breeding of long generation seed plants such as trees practical for the first time. Methods of promoting early reproductive development also would be useful for shortening growth periods, thereby broadening the geographic range in which a crop such as rice, corn or coffee can be grown. Unfortunately, methods for promoting early reproductive development in a seed plant have not yet been described. Thus, there is a need for methods that promote early reproductive development. The present invention satisfies this need and provides related advantages as well.

SUMMARY OF THE INVENTION

The present invention provides a non-naturally occurring seed plant containing a first ectopically expressible nucleic acid molecule encoding a first floral meristem identity gene product, provided that the nucleic acid molecule is not ectopically expressed due to a mutation in an endogenous TERMINAL FLOWER gene. For example, the invention provides a transgenic seed plant containing a first ectopically expressible nucleic acid molecule encoding a floral meristem identity gene product such as APETALA1 (AP1), CAULIFLOWER (CAL) or LEAFY (LFY). A transgenic seed plant of the invention can be, for example, an angiosperm such as a cereal plant, leguminous plant, oilseed plant, hardwood tree, fruit-bearing plant or ornamental flower or a gymnosperm such as a coniferous tree.

The invention further provides a method of converting shoot meristem to floral meristem in an angiosperm by ectopically expressing a first nucleic acid molecule encoding a first floral meristem identity gene product. For example, the invention provides a method of converting shoot meristem to floral meristem by introducing a first nucleic acid molecule encoding a first floral meristem identity gene product into an angiosperm such that the floral meristem identity gene product is ectopically expressed in the angiosperm. Thus, a nucleic acid molecule encoding a floral meristem identity gene product such as AP1, CAL or LFY can be introduced into an angiosperm, such that expression of the nucleic acid molecule in shoot meristem results in conversion of shoot meristem to floral meristem.

The invention further provides a method of promoting early reproductive development in a seed plant by ectopically expressing a first nucleic acid molecule encoding a first floral meristem identity gene product in the plant. For example, the invention provides a method of promoting early reproductive development in a seed plant by introducing a first nucleic acid molecule encoding a first floral meristem identity gene product into the seed plant such that the floral meristem identity gene product is ectopically expressed in the seed plant. A nucleic acid molecule encoding a floral meristem identity gene product such as AP1, CAL or LFY, for example, can be ectopically expressed in a seed plant prior to the time an endogenous floral meristem identity gene product is expressed to promote early reproductive development in the seed plant.

DETAILED DESCRIPTION OF THE INVENTION

Figure 1:
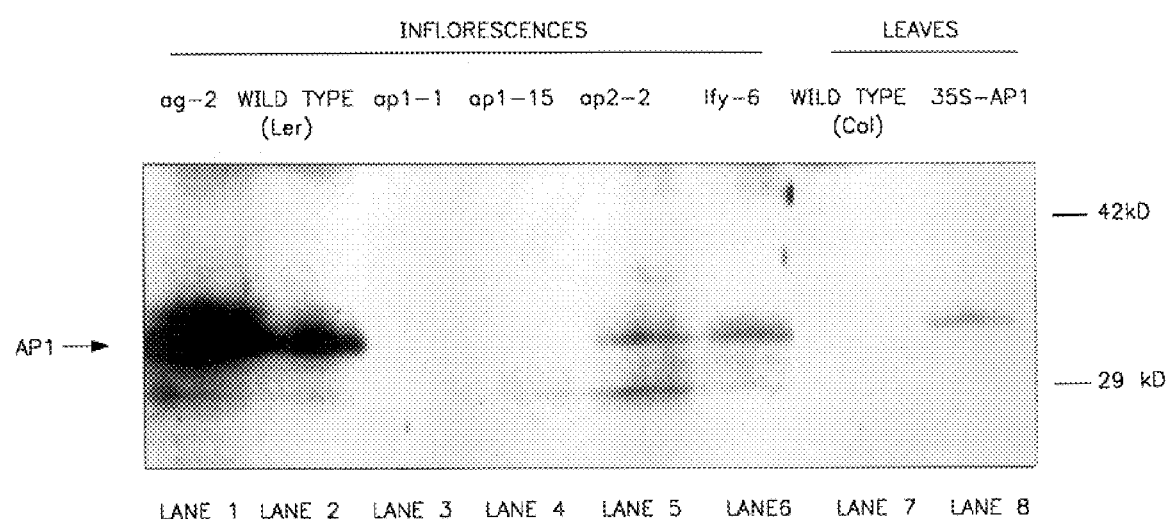
FIG. 1 illustrates a western-blot analysis of tissues from wild type and mutant Arabiedopsis plants with anti-AP1 antisera.

The present invention provides a non-naturally occurring seed plant containing a first ectopically expressible nucleic acid molecule encoding a first floral meristem identity gene product, provided that the nucleic acid molecule is not ectopically expressed due to a mutation in an endogenous TERMINAL FLOWER gene. For example, the invention provides a transgenic seed plant containing a first ectopically expressible floral meristem identity gene product such as APETALA1 (AP1), CAULIFLOWER (CAL) or LEAFY (LFY). A transgenic seed plant can be, for example, an angiosperm such as a cereal plant, leguminous plant, oilseed plant, hardwood tree, fruit-bearing plant or ornamental flower or a gymnosperm such as a coniferous tree.

A flower, like a leaf or shoot, is derived from the shoot apical meristem, which is a collection of undifferentiated cells set aside during embryogenesis. The production of vegetative structures, such as leaves or shoots, and of reproductive structures, such as flowers, is temporally segregated, such that a leaf or shoot arises early in a plant life cycle, while a flower develops later. The transition from vegetative to reproductive development is the consequence of a process termed floral induction (Yanofsky, *Ann. Rev. Plant Physiol. Plant Mol. Biol.* 46:167–188 (1995), which is incorporated herein by reference).

Once induced, shoot apical meristem either persists and produces floral meristem, which gives rise to flowers, and lateral meristem, which gives rise to branches, or is itself converted to floral meristem. Floral meristem differentiates into a single flower having a fixed number of floral organs in a whorled arrangement. Dicots, for example, contain four whorls (concentric rings), in which sepals (first whorl) and petals (second whorl) surround stamens (third whorl) and carpels (fourth whorl).

Although shoot meristem and floral meristem both consist of meristemic tissue, shoot meristem is distinguishable from the more specialized floral meristem. Shoot meristem generally is indeterminate and gives rise to an unspecified number of floral and lateral meristems. In contrast, floral meristem is determinate and gives rise to the fixed number of floral organs that comprise a flower.

By convention herein, a wild-type gene sequence is represented in upper case italic letters (for example, APETALA1), and a wild-type gene product is represented in upper case non-italic letters (APETALA1). Further, a mutant gene allele is represented in lower case italic letters (ap1), and a mutant gene product is represented in lower case non-italic letters (ap1).

Genetic studies have identified a number of genes involved in regulating flower development. These genes can be classified into different groups depending on their function. Flowering time genes, for example, are involved in floral induction and regulate the transition from vegetative to reproductive growth. In comparison, the floral meristem identity genes, which are the subject matter of the present invention as disclosed herein, encode proteins that promote the conversion of shoot meristem to floral meristem in an angiosperm. In addition, floral organ identity genes encode proteins that determine whether sepals, petals, stamens or carpels are formed during floral development (Yanofsky, supra, 1995; Weigel, *Ann. Rev. Genetics* 29:19–39 (1995), which is incorporated herein by reference). Some of the floral meristem identity gene products also have a role in specifying floral organ identity.

Floral meristem identity genes have been identified by characterizing genetic mutations that prevent or alter floral meristem formation. Among floral meristem identity gene mutations in *Arabidopsis thaliana*, those in the gene LEAFY (LFY) generally have the strongest effect on floral meristem identity. Mutations in LFY completely transform the basal-most flowers into secondary shoots and have variable effects on later-arising (apical) flowers. In comparison, mutations in the floral meristem identity gene APETALA1 (AP1) result in replacement of a few basal flowers by inflorescence shoots that are not subtended by leaves. An apical flower produced in an ap1 mutant has an indeterminate structure, in which a flower arises within a flower. These mutant phenotypes indicate that both AP1 and LFY contribute to establishing the identity of the floral meristem although neither gene is absolutely required. The phenotype of lfy ap1 double mutants, in which structures with flower-like characteristics are very rare, indicates that LFY and AP1 encode partially redundant activities.

In addition to the LFY and AP1 genes, a third locus that greatly enhances the ap1 mutant phenotype has been identified in Arabidopsis. This locus, designated CAULIFLOWER (CAL), derives its name from the resulting "cauliflower" phenotype, which is strikingly similar to the common garden variety of cauliflower (Kempin et al., *Science* 267:522–525 (1995), which is incorporated herein by reference). In an ap1 cal double mutant, floral meristem behaves as shoot meristem in that there is a massive proliferation of meristems in the position that normally would be occupied by a single flower. However, an Arabidopsis mutant lacking only CAL, such as cal-1, has a normal phenotype, indicating that AP1 can substitute for the loss of CAL in these plants. In addition, because floral meristem that forms in an ap1 mutant behaves as shoot meristem in an ap1 cal double mutant, CAL can largely substitute for AP1 in specifying floral meristem. These genetic data indicate that CAL and AP1 encode activities that are partially redundant in converting shoot meristem to floral meristem.

Other genetic loci play at least minor roles in specifying floral meristem identity. For example, although a mutation in APETALA2 (AP2) alone does not result in altered inflorescence characteristics, ap2 ap1 double mutants have indeterminate flowers (flowers with shoot-like characteristics; Bowman et al., *Development* 119:721–743 (1993), which is incorporated herein by reference). Also, mutations in the CLAVATA1 (CLV1) gene result in an enlarged meristem and lead to a variety of phenotypes (Clark et al., *Development* 119:397–418 (1993)). In a clv1 ap1 double mutant, formation of flowers is initiated, but the center of each flower often develops as an indeterminate inflorescence. Thus, mutations in CLAVATA1 result in the loss of floral meristem identity in the center of wild-type flowers. Genetic evidence also indicates that the gene product of UNUSUAL FLORAL ORGANS (UFO) plays a role in determining the identity of floral meristem. Additional floral meristem identity genes associated with altered floral meristem formation remain to be isolated.

Mutations in another locus, designated TERMINAL FLOWER (TFL), produce phenotypes that generally are reversed as compared to mutations in the floral meristem identity genes. For example, tfl mutants flower early, and the indeterminate apical and lateral meristems develop as determinate floral meristems (Alvarez et al., *Plant J.* 2:103–116 (1992)). These characteristics indicate that the TFL promotes maintenance of shoot meristem. TFL also acts directly or indirectly to negatively regulate AP1 and LFY expression in shoot meristem since these AP1 and LFY are ectopically expressed in the shoot meristem of tfl mutants (Gustafson-Brown et al., *Cell* 76:131–143 (1994); Weigel et al., *Cell* 69:843–859 (1992)). It is recognized that a plant having a mutation in TFL can have a phenotype similar to a non-naturally occurring seed plant of the invention. Such tfl mutants, however, which have a mutation in an endogenous TERMINAL FLOWER gene, are explicitly excluded from the scope of the present invention.

The results of such genetic studies indicate that several floral meristem identity gene products, including AP1, CAL and LFY, act redundantly to convert shoot meristem to floral meristem in an angiosperm. As disclosed herein, ectopic expression of a single floral meristem identity gene product such as AP1, CAL or LFY is sufficient to convert shoot meristem to floral meristem in an angiosperm. Thus, the present invention provides a non-naturally occurring seed plant such as an angiosperm or gymnosperm that contains a first ectopically expressible nucleic acid molecule encoding a first floral meristem identity gene product, provided that such ectopic expression is not due to a mutation in an endogenous TERMINAL FLOWER gene.

As disclosed herein, an ectopically expressible nucleic acid molecule encoding a floral meristem identity gene product can be, for example, a transgene encoding a floral meristem identity gene product under control of a heterologous gene regulatory element. In addition, such an ectopically expressible nucleic acid molecule can be an endogenous floral meristem identity gene coding sequence that is placed under control of a heterologous gene regulatory element. The ectopically expressible nucleic acid molecule also can be, for example, an endogenous floral meristem identity gene having a modified gene regulatory element such that the endogenous floral meristem identity gene is no longer subject to negative regulation by TFL.

The term "ectopically expressible" is used herein to refer to a nucleic acid molecule encoding a floral meristem identity gene product that can be expressed in a tissue other than a tissue in which it normally is expressed or at a time other than the time at which it normally is expressed, provided that the floral meristem identity gene product is not expressed from its native, naturally occurring promoter. Ectopic expression of a floral meristem identity gene product is a result of the expression of the gene coding region from a heterologous promoter or from a modified variant of its own promoter, such that expression of the floral meristem identity gene product is no longer in the tissue in which it normally is expressed or at the time at which it normally is expressed. An exogenous nucleic acid molecule encoding an AP1 gene product under control of its native, wild type promoter, for example, does not constitute an ectopically expressible nucleic acid molecule encoding a floral meristem identity gene product. However, a nucleic acid molecule encoding an AP1 gene product under control of a constitutive promoter, which results in expression of AP1 in a tissue such as shoot meristem where it is not normally expressed, is an ectopically expressible nucleic acid molecule as defined herein.

Actual ectopic expression of a floral meristem identity gene is dependent on various factors and can be constitutive or inducible expression. For example, AP1, which normally is expressed in floral meristem, is ectopically expressible in the shoot meristem of an angiosperm. As disclosed herein, when a floral meristem identity gene product such as AP1, CAL or LFY is ectopically expressed in shoot meristem in an angiosperm, the shoot meristem is converted to floral meristem and early reproductive development can occur (see Examples I, III and IV).

An ectopically expressible nucleic acid molecule encoding a floral meristem identity gene product can be expressed prior to the time in development at which the corresponding endogenous gene normally is expressed. For example, an Arabidopsis plant grown under continuous light conditions expresses AP1 just prior to day 18, when normal reproductive development (flowering) begins. However, as disclosed herein, AP1 can be ectopically expressed in shoot meristem prior to day 18, resulting in early conversion of shoot meristem to floral meristem and early reproductive development. As disclosed in Example ID, a transgenic Arabidopsis plant that ectopically expresses AP1 in shoot meristem under control of a constitutive promoter can flower at day 10, which is earlier than the time of reproductive development for a non-transgenic plant grown under the same conditions (day 18). It is recognized that in some transgenic seed plants containing, for example, an exogenous nucleic acid molecule encoding AP1 under control of a constitutive promoter, neither the exogenous nor endogenous AP1 will be expressed. Such transgenic plants in which AP1 gene expression is cosuppressed, although not characterized by early reproductive development, also can be valuable as disclosed below.

As used herein, the term "floral meristem identity gene product" means a gene product that promotes conversion of shoot meristem to floral meristem in an angiosperm. As disclosed herein in Examples I, II and III, expression of a floral meristem identity gene product such as AP1, CAL or LFY in shoot meristem can convert shoot meristem to floral meristem in an angiosperm. Furthermore, ectopic expression of a floral meristem identity gene product also can promote early reproductive development (see Example ID).

A floral meristem identity gene product is distinguishable from a late flowering gene product or an early flowering gene product. The use of a late flowering gene product or an early flowering gene product is not encompassed within the scope of the present invention. In addition, reference is made herein to an "inactive" floral meristem identity gene product, as exemplified by the product of the *Brassica oleracea* var. *botrytis* CAL gene (BobCAL) (see below). Expression of an inactive floral meristem identity gene product in an angiosperm does not result in the conversion of shoot meristem to floral meristem in the angiosperm. An inactive floral meristem identity gene product such as BobCAL is excluded from the meaning of the term "floral meristem identity gene product" as defined herein.

A floral meristem identity gene product can be, for example, an AP1 gene product having the amino acid sequence of SEQ ID NO: 2, which is a 256 amino acid gene product encoded by the *Arabidopsis thaliana* AP1 cDNA. The Arabidopsis AP1 cDNA encodes a highly conserved MADS domain, which can function as a DNA-binding domain, and a K domain, which has structural similarity to the coiled-coil domain of keratins and can be involved in protein-protein interactions.

As used herein, the term "APETALA1," "AP1" or "AP1 gene product" means a floral meristem identity gene product that is characterized, in part, by having an amino acid sequence that has at least about 70 percent amino acid identity with the amino acid sequence of SEQ ID NO: 2 in the region from amino acid 1 to amino acid 163 or with the amino acid sequence of SEQ ID NO: 8 in the region from amino acid 1 to amino acid 163. Like other floral meristem identity gene products, AP1 promotes conversion of shoot meristem to floral meristem in an angiosperm. An AP1 gene product useful in the invention can be, for example, Arabidopsis AP1 having the amino acid sequence of SEQ ID NO: 2; *Brassica oleracea* AP1 having the amino acid sequence of SEQ ID NO: 4; *Brassica oleracea* var. *botrytis* AP1 having the amino acid sequence of SEQ ID NO: 6 or *Zea mays* AP1 having the amino acid sequence of SEQ ID NO: 8.

In wild-type Arabidopsis, AP1 RNA is expressed in flowers but is not detectable in roots, stems or leaves (Mandel et al., *Nature* 360:273–277 (1992), which is incorporated herein by reference). The earliest detectable expression of AP1 RNA is in young floral meristem at the time it initially forms on the flanks of shoot meristem. Expression of AP1 increases as the floral meristem increases in size; no AP1 expression is detectable in shoot meristem. In later stages of development, AP1 expression ceases in cells that will give rise to reproductive organs of a flower (stamens and carpels), but is maintained in cells that will give rise to non-reproductive organs (sepals and petals; Mandel, supra, 1992). Thus, in nature, AP1 expression is restricted to floral meristem and to certain regions of the flowers that develop from this meristemic tissue.

CAULIFLOWER (CAL) is another example of a floral meristem identity gene product. As used herein, the term "CAULIFLOWER," "CAL" or "CAL gene product" means a floral meristem identity gene product that is characterized, in part, by having an amino acid sequence that has at least about 70 percent amino acid identity with the amino acid sequence of SEQ ID NO: 10 in the region from amino acid 1 to amino acid 160 or with the amino acid sequence of SEQ ID NO: 12 in the region from amino acid 1 to amino acid 160.

A CAL gene product is exemplified by the Arabidopsis CAL gene product, which has the amino acid sequence of SEQ ID NO: 10, or the *Brassica oleracea* CAL gene product, which has the amino acid sequence of SEQ ID NO: 12. As disclosed herein, CAL, like AP1, contains a MADS domain and a K domain. The MADS domains of CAL and AP1 differ in only five of 56 amino acid residues, where four of the five differences represent conservative amino acid replacements. Over the entire sequence, the Arabidopsis CAL and Arabidopsis AP1 sequences (SEQ ID NOS: 10 and 2) are 76% identical and are 88% similar if conservative amino acid substitutions are allowed.

Similar to the expression pattern of AP1, CAL RNA is expressed in young floral meristem in Arabidopsis. However, in contrast to AP1 expression, which is high throughout sepal and petal development, CAL expression is low in these organs. Thus, in nature, CAL is expressed in floral meristem and, to a lesser extent, in the organs of developed flowers.

The skilled artisan will recognize that, due to the high sequence conservation between AP1 and CAL, a novel ortholog can be categorized as both a CAL and an AP1, as defined herein. However, if desired, an AP1 ortholog can be distinguished from a CAL ortholog by demonstrating a greater similarity to Arabidopsis AP1 than to any other MADS box gene, such as CAL, as set forth in Purugganan et al. (*Genetics* 140:345–356 (1995), which is incorporated herein by reference). Furthermore, AP1 can be distinguished from CAL by its ability to complement, or restore a wild-type phenotype, when introduced into a strong ap1 mutant. For example, introduction of Arabidopsis AP1 (AGL7) complements the phenotype of the strong ap1-1 mutant; however, introduction of CAL (AGL10) into a cal-1 ap1-1 mutant plant yields the ap1-1 single mutant phenotype, demonstrating that CAL cannot complement the ap1-1 mutation (see, for example, Mandel et al., supra, 1992; Kempin et al., supra, 1995). Thus, AP1 can be distinguished from CAL, if desired, by the ability of a nucleic acid molecule encoding AP1 to complement a strong ap1 mutant such as ap1-1 or ap1-15.

LEAFY (LFY) is yet another example of a floral meristem identity gene product. As used herein, the term "LEAFY" or "LFY" or "LFY gene product" means a floral meristem identity gene product that is characterized, in part, by having an amino acid sequence that has at least about 70 percent amino acid identity with the amino acid sequence of SEQ ID NO: 16. In nature, LFY is expressed in floral meristem as well as during vegetative development. As disclosed herein, ectopic expression in shoot meristem of a floral meristem identity gene product, which normally is expressed in floral meristem, can convert shoot meristem to floral meristem in an angiosperm. Under appropriate conditions, ectopic expression in shoot meristem of a floral meristem identity gene product such as AP1, CAL, LFY, or a combination thereof, can promote early reproductive development.

Flower development in Arabidopsis is recognized in the art as a model for flower development in angiosperms in general. Gene orthologs corresponding to the Arabidopsis genes involved in the early steps of flower formation have been identified in distantly related angiosperm species, and these gene orthologs show remarkably similar patterns of RNA expression. Mutations in gene orthologs also result in phenotypes that correspond to the phenotype produced by a similar mutation in Arabidopsis. For example, orthologs of the Arabidopsis floral meristem identity genes AP1 and LFY and the Arabidopsis organ identity genes AGAMOUS, APETALA3 and PISTILLATA have been isolated from monocots such as maize and, where characterized, reveal the anticipated RNA expression patterns and related mutant phenotypes (Schmidt et al., *Plant Cell* 5:729–737 (1993); and Veit et al., *Plant Cell* 5:1205–1215 (1993), each of which is incorporated herein by reference). Furthermore, a gene ortholog can be functionally interchangeable in that it can function across distantly related species boundaries (Mandel et al., *Cell* 71:133–143 (1992), which is incorporated herein by reference). Taken together, these data suggest that the underlying mechanisms controlling the initiation and proper development of flowers are conserved across distantly related dicot and monocot boundaries.

Floral meristem identity genes in particular are conserved among distantly related angiosperm and gymnosperm species. For example, a gene ortholog of Arabidopsis AP1 has been isolated from *Antirrhinum majus* (snapdragon; Huijser et al., *EMBO J.* 11:1239–1249 (1992), which is incorporated herein by reference). As disclosed herein, an ortholog of Arabidopsis AP1 also has been isolated from *Brassica oleracea* var. *botrytis* (cauliflower) and *Zea Mays* (maize; see Example VA). Furthermore, AP1 orthlogs also can be isolated from gymnosperms. Similarly, gene orthologs of Arabidopsis LFY have been isolated from angiosperms such as *Antirrhinum majus*, tobacco and poplar tree and from gymnosperms such as Douglas fir (Coen et al., *Cell*, 63:1311–1322 (1990); Kelly et al., *Plant Cell* 7:225–234 (1995); and Rottmann et al., *Cell Biochem.* Suppl. 17B: 23 (1993); Strauss et al., *Molec. Breed* 1:5–26 (1995), each of which is incorporated herein by reference). The conservation of floral meristem identity gene products in non-flowering plants such as coniferous trees indicates that floral meristem identity genes can promote the reproductive development of gymnosperms as well as angiosperms.

The characterization of ap1 and lfy mutants also indicates that floral meristem identity gene products such as AP1 and LFY function similarly in distantly related plant species. For example, a mutation in the Antirrhinum AP1 ortholog results in a phenotype similar to the Arabidopsis ap1 indeterminate flower within a flower phenotype (Huijser et al., supra, 1992). In addition, a mutation in the Antirrhinum LFY ortholog results in a phenotype similar to the Arabidopsis lfy mutant phenotype (Coen et al., supra, 1995)

A floral meristem identity gene product also can function across species boundaries. For example, introduction of a nucleic acid molecule encoding Arabidopsis LFY into a heterologous seed plant such as tobacco or aspen results in early reproductive development (Weigel and Nilsson, *Nature* 377:495–500 (1995), which is incorporated herein by reference). As disclosed herein, a nucleic acid molecule encoding an Arabidopsis AP1 gene product (SEQ ID NO: 1) or an Arabidopsis CAL gene product (SEQ ID NO: 9) can be introduced into a heterologous seed plant such as corn, wheat, rice or pine and, upon ectopic expression, can promote early reproductive development in the transgenic seed plant. Furthermore, as disclosed herein, the conserved nature of the AP1, CAL and LFY coding sequences among diverse seed plant species allows a nucleic acid molecule encoding a floral meristem identity gene product isolated from essentially any seed plant to be introduced into essentially any other seed plant, wherein, upon appropriate expression of the introduced nucleic acid molecule in the seed plant, the floral meristem identity gene product promotes early reproductive development in the seed plant.

If desired, a novel AP1, CAL or LFY coding sequence can be isolated from a seed plant using a nucleotide sequence as a probe and methods well known in the art of molecular biology (Sambrook et al. (eds.), *Molecular Cloning: A Laboratory Manual* (Second Edition), Plainview, N.Y.: Cold Spring Harbor Laboratory Press (1989), which is incorporated herein by reference). As exemplified herein and discussed in detail below (see Example VA), an AP1 ortholog from *Zea Mays* (maize; SEQ ID NO: 7) was isolated using the Arabidopsis AP1 cDNA (SEQ ID NO: 1) as a probe.

In one embodiment, the invention provides a non-naturally occurring seed plant that contains a first ectopically expressible nucleic acid molecule encoding a floral meristem identity gene product, provided that the first nucleic acid molecule is not ectopically expressed due to a mutation in an endogenous TERMINAL FLOWER gene, and that is characterized by early reproductive development. As used herein, the term "characterized by early reproductive development," when used in reference to a non-naturally occurring seed plant of the invention, means a non-naturally occurring seed plant that forms reproductive structures earlier than the time when reproductive structures form on a corresponding naturally occurring seed plant that is grown under the same conditions and that does not ectopically express a floral meristem identity gene product. For example, the reproductive structure of an angiosperm is a flower, and the reproductive structure of a coniferous plant is a cone. For a particular naturally occurring seed plant, reproductive development occurs at a well-defined time that depends, in part, on genetic factors as well as on environmental conditions, such as day length and temperature. Thus, given a defined set of environmental condition and lacking ectopic expression of a floral meristem identity gene product, a naturally occurring seed plant will undergo reproductive development at a relatively fixed time.

It is recognized that various transgenic plants that are characterized by early reproductive development have been described previously. Such transgenic plants, as discussed herein, are distinguishable from a non-naturally occurring seed plant of the invention or are explicitly excluded from the present invention. The product of a "late-flowering gene" can promote early reproductive development. However, a late flowering gene product is not a floral meristem identity gene product since it does not specify the conversion of shoot meristem to floral meristem in an angiosperm. Therefore, a transgenic plant expressing a late-flowering gene product is distinguishable from a non-naturally occurring seed plant of the invention. For example, a transgenic plant expressing the late-flowering gene, CONSTANS (CO), flowers earlier than the corresponding wild type plant, but does not contain an ectopically expressible nucleic acid molecule encoding a floral meristem identity gene product (Putterill et al., *Cell* 80:847–857 (1995)). Thus, the early-flowering transgenic plant described by Putterill et al. is not a non-naturally occurring seed plant as defined herein.

Early reproductive development also has been observed in a transgenic tobacco plant expressing an exogenous rice MADS domain gene. Although the product of the rice MADS domain gene promotes early reproductive development, it does not specify the identity of floral meristem and, thus, cannot convert shoot meristem to floral meristem in an angiosperm (Chung et al., *Plant Mol. Biol.* 26:657–665 (1994)). Therefore, an early-flowering transgenic plant containing this rice MADS domain gene, like an early-flowering transgenic plant containing CONSTANS, is distinguishable from an early-flowering non-naturally occurring seed plant of the invention.

Mutations in a class of genes known as "early-flowering genes" also produce plants characterized by early reproductive development. Such early-flowering genes include, for example, EARLY FLOWERING 1–3 (ELF1, ELF2, ELF3); EMBRYONIC FLOWER 1,2 (EMF1, EMF2); LONG HYPOCOTYL 1,2 (HY1, HY2); PHYTOCHROME B (PHYB), SPINDLY (SPY) and TERMINAL FLOWER (TFL) (Weigel, supra, 1995). The wild type product of an early-flowering gene retards reproductive development and is distinguishable from a floral meristem identity gene product in that an early-flowering gene product does not promote conversion of shoot meristem to floral meristem in an angiosperm. A plant that flowers early due to the loss of an early-flowering gene product function is distinct from a non-naturally occurring seed plant of the invention characterized by early reproductive development since such a plant does not contain an ectopically expressible nucleic acid molecule encoding a floral meristem identity gene product.

An Arabidopsis plant having a mutation in the TERMINAL FLOWER (TFL) gene is characterized by early reproductive development and by the conversion of shoots to flowers (Alvarez et al., *Plant J.* 2:103–116 (1992), which is incorporated herein by reference). However, TFL is not a floral meristem identity gene product, as defined herein. Specifically, it is the loss of TFL that promotes conversion of shoot meristem to floral meristem. Since the function of TFL is to antagonize formation of floral meristem, a tfl mutant, which lacks functional TFL, converts shoot meristem to floral meristem prematurely. Although TFL is not a floral meristem identity gene product and does not itself convert shoot meristem to floral meristem, the loss of TFL can result in a plant with an ectopically expressed floral meristem identity gene product. However, such a tfl mutant, in which a mutation in an endogenous TERMINAL FLOWER gene results in conversion of shoot meristem to floral meristem, is excluded explicitly from the present invention.

As used herein, the term "transgenic" refers to a seed plant that contains in its genome an exogenous nucleic acid molecule, which can be derived from the same or a different plant species. The exogenous nucleic acid molecule can be a gene regulatory element such as a promoter, enhancer or other regulatory element or can contain a coding sequence, which can be linked to a heterologous gene regulatory element.

As used herein, the term "seed plant" means an angiosperm or a gymnosperm. The term "angiosperm," as used herein, means a seed-bearing plant whose seeds are borne in a mature ovary (fruit). An angiosperm commonly is recognized as a flowering plant. The term "gymnosperm," as used herein, means a seed-bearing plant with seeds not enclosed in an ovary.

Angiosperms are divided into two broad classes based on the number of cotyledons, which are seed leaves that generally store or absorb food. Thus, a monocotyledonous angiosperm is an angiosperm having a single cotyledon, and a dicotyledonous angiosperm is an angiosperm having two cotyledons. Angiosperms are well known and produce a variety of useful products including materials such as lumber, rubber, and paper; fibers such as cotton and linen; herbs and medicines such as quinine and vinblastine; ornamental flowers such as roses and orchids; and foodstuffs such as grains, oils, fruits and vegetables.

Angiosperms encompass a variety of flowering plants, including, for example, cereal plants, leguminous plants, oilseed plants, hardwood trees, fruit-bearing plants and ornamental flowers, which general classes are not necessarily exclusive. Such angiosperms include for example, a cereal plant, which produces an edible grain cereal. Such cereal plants include, for example, corn, rice, wheat, barley, oat, rye, orchardgrass, guinea grass, sorghum and turfgrass. In addition, a leguminous plant is an angiosperm that is a member of the pea family (Fabaceae) and produces a characteristic fruit known as a legume. Examples of leguminous plants include, for example, soybean, pea, chickpea, moth bean, broad bean, kidney bean, lima bean, lentil, cowpea, dry bean, and peanut. Examples of legumes also include alfalfa, birdsfoot trefoil, clover and sainfoin. An oilseed plant also is an angiosperm with seeds that are useful as a source of oil. Examples of oilseed plants include soybean, sunflower, rapeseed and cottonseed.

An angiosperm also can be a hardwood tree, which is a perennial woody plant that generally has a single stem (trunk). Examples of such trees include alder, ash, aspen, basswood (linden), beech, birch, cherry, cottonwood, elm, eucalyptus, hickory, locust, maple, oak, persimmon, poplar, sycamore, walnut and willow. Trees are useful, for example, as a source of pulp, paper, structural material and fuel.

An angiosperm also can be a fruit-bearing plant, which produces a mature, ripened ovary (usually containing seeds) that is suitable for human or animal consumption. For example, hops are a member of the mulberry family prized for their flavoring in malt liquor. Fruit-bearing angiosperms also include grape, orange, lemon, grapefruit, avocado, date, peach, cherry, olive, plum, coconut, apple and pear trees and blackberry, blueberry, raspberry, strawberry, pineapple, tomato, cucumber and eggplant plants. An ornamental flower is an angiosperm cultivated for its decorative flower. Examples of commercially important ornamental flowers include rose, orchid, lily, tulip and chrysanthemum, snapdragon, camellia, carnation and petunia plants. The skilled artisan will recognize that the methods of the invention can be practiced using these or other angiosperms, as desired.

Gymnosperms encompass four divisions: cycads, ginkgo, conifers and gnetophytes. The conifers are the most widespread of living gymnosperms and frequently are cultivated for structural wood or for pulp or paper. Conifers include redwood trees, pines, firs, spruces, hemlocks, Douglas firs, cypresses, junipers and yews. The skilled artisan will recognize that the methods of the invention can be practiced with these and other gymnosperms.

As used herein, the term "non-naturally occurring seed plant" means a seed plant containing a genome that has been modified by man. A transgenic seed plant, for example, is a non-naturally occurring seed plant that contains an exogenous nucleic acid molecule and, therefore, has a genome that has been modified by man. Furthermore, a seed plant that contains, for example, a mutation in an endogenous floral meristem identity gene regulatory element as a result of calculated exposure to a mutagenic agent also contains a genome that has been modified by man. In contrast, a seed plant containing a spontaneous or naturally occurring mutation is not a "non-naturally occurring seed plant" and, therefore, is not encompassed within the invention.

In various embodiments, the present invention provides a non-naturally occurring seed plant containing a first ectopically expressible nucleic acid molecule encoding a first floral meristem identity gene product, provided that the first nucleic acid molecule is not ectopically expressed due to a mutation in an endogenous TERMINAL FLOWER gene. If desired, a non-naturally occurring seed plant of the invention can contain a second ectopically expressible nucleic acid molecule encoding a second floral meristem identity gene product that is different from the first floral meristem identity gene product, provided that the first or second nucleic acid molecule is not ectopically expressed due to a mutation in an endogenous TERMINAL FLOWER gene.

An ectopically expressible nucleic acid molecule encoding a floral meristem identity gene product can be expressed, as desired, either constitutively or inducibly. Such an ectopically expressible nucleic acid molecule encoding a floral meristem identity gene product can be an endogenous floral meristem identity gene that has, for example, a mutation in a gene regulatory element. An ectopically expressible nucleic acid molecule encoding a floral meristem identity gene product also can be an endogenous nucleic acid molecule encoding a floral meristem identity gene product that is linked to an exogenous, heterologous gene regulatory element that confers ectopic expression. In addition, an ectopically expressible nucleic acid molecule encoding a floral meristem identity gene product can be an exogenous nucleic acid molecule that encodes a floral meristem identity gene product under control of a heterologous gene regulatory element.

A non-naturally occurring seed plant of the invention can contain an endogenous floral meristem identity gene having a modified gene regulatory element. The term "modified gene regulatory element," as used herein in reference to the regulatory element of a floral meristem identity gene, means a regulatory element having a mutation that results in ectopic expression of the linked endogenous floral meristem identity gene. Such a gene regulatory element can be, for example, a promoter or enhancer element and can be positioned 5' or 3' to the coding sequence or within an intronic sequence of the floral meristem identity gene. A modified gene regulatory element can have, for example, a nucleotide insertion, deletion or substitution that is produced, for example, by chemical mutagenesis using a mutagen such as ethylmethane sulfonate or by insertional mutagenesis using a transposable element. A modified gene regulatory element can be a functionally inactivated binding site for TFL or a functionally inactivated binding site for a gene product regulated by TFL, such that modification of the gene regulatory element results in ectopic expression of the linked floral meristem identity gene product, for example, in the shoot meristem of an angiosperm.

The present invention also provides a transgenic seed plant containing a first exogenous gene promoter that regulates a first ectopically expressible nucleic acid molecule encoding a first floral meristem identity gene product and a second exogenous gene promoter that regulates a second ectopically expressible nucleic acid molecule encoding a second floral meristem identity gene product.

The present invention further provides a transgenic seed plant containing a first exogenous ectopically expressible nucleic acid molecule encoding a first floral meristem identity gene product and a second exogenous gene promoter that regulates a second ectopically expressible nucleic acid molecule encoding a second floral meristem identity gene product, provided that the first nucleic acid molecule is not ectopically expressed due to a mutation in an endogenous TERMINAL FLOWER gene.

In addition, the invention provides a transgenic seed plant containing a first exogenous ectopically expressible nucleic acid molecule encoding a first floral meristem identity gene product, provided that the first second nucleic acid molecule is not ectopically expressed due to a mutation in an endogenous TERMINAL FLOWER gene, and further containing a second exogenous ectopically expressible nucleic acid molecule encoding a second floral meristem identity gene product, where the first floral meristem identity gene product is different from the second floral meristem identity gene product.

As disclosed herein, ectopic expression of two different floral meristem identity gene products can be particularly useful. A transgenic Arabidopsis line constitutively expressing AP1 under control of the cauliflower mosaic virus 35S promoter (see Example I) was crossed with a transgenic Arabidopsis line constitutively expressing LFY under control of the cauliflower mosaic virus 35S promoter (see Example III), and the resulting progeny were analyzed. A fraction of the progeny flowered were characterized by enhanced early reproductive development as compared to the early reproductive development of 35S-AP1 transgenic lines or 35S-LFY transgenic lines. PCR-based analyses demonstrated that all of the transgenic plants that were characterized by enhanced early reproductive development contained both the 35S-AP1 and 35S-LFY transgenes. These results indicate that ectopic expression of the combination of AP1 and LFY in a seed plant can result in enhanced early reproductive development as compared to the early reproductive development obtained by ectopic expression of AP1 or LFY alone. Thus, by using a combination of two different floral meristem identity gene products, plant breeding, for example, can be accelerated further as compared to the use of a single floral meristem identity gene product.

A useful combination of first and second floral meristem identity gene products can be, for example, AP1 and LFY, CAL and LFY, or AP1 and CAL. A particularly useful combination of first and second floral meristem identity gene products is the combination of AP1 with LFY, as disclosed above, or the combination of CAL with LFY. Where a transgenic seed plant of the invention contains first and second exogenous nucleic acid molecules encoding different floral meristem identity gene products, it will be recognized that the order of introducing the first and second nucleic acid molecules into the seed plant is not important for purposes of the present invention. Thus, a transgenic seed plant of the invention having, for example, AP1 as a first floral meristem identity gene product and LFY as a second floral meristem identity gene product is equivalent to a transgenic seed plant having LFY as a first floral meristem identity gene product and AP1 as a second floral meristem identity gene product.

The invention also provides methods of converting shoot meristem to floral meristem in an angiosperm by ectopically expressing a first ectopically expressible nucleic acid molecule encoding a first floral meristem identity gene product in the angiosperm. Thus, the invention provides, for example, a method of converting shoot meristem to floral meristem in an angiosperm by introducing an exogenous, ectopically expressible nucleic acid molecule encoding a floral meristem identity gene product into the angiosperm, thereby producing a transgenic angiosperm. A floral meristem identity gene product such as AP1, CAL or LFY, or a chimeric protein containing, in part, a floral meristem identity gene product, as disclosed below, is useful in converting shoot meristem to floral meristem according to the methods of the invention.

As used herein, the term "introducing," when used in reference to a nucleic acid molecule and a seed plant such as an angiosperm or a gymnosperm, means transferring an exogenous nucleic acid molecule into the seed plant. For example, an exogenous nucleic acid molecule encoding a floral meristem identity gene product can be introduced into a seed plant by a variety of methods including Agrobacterium-mediated transformation or direct gene transfer methods such as electroporation or microprojectile-mediated transformation.

Transformation methods based upon the soil bacterium *Agrobacterium tumefaciens,* known as "agro-infection," are useful for introducing a nucleic acid molecule into a broad range of angiosperms and gymnosperms. The wild type form of Agrobacterium contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. Agrobacterium-based vector is a modified form of a Ti plasmid, in which the tumor inducing functions are replaced by nucleic acid sequence of interest to be introduced into the plant host.

Current protocols for Agrobacterium-mediated transformation employ cointegrate vectors or, preferably, binary vector systems in which the components of the Ti plasmid are divided between a helper vector, which resides permanently in the Agrobacterium host and carries the virulence genes, and a shuttle vector, which contains the gene of interest bounded by T-DNA sequences. A variety of binary vectors are well known in the art and are commercially available from, for example, Clontech (Palo Alto, Calif.). Methods of coculturing Agrobacterium with cultured plant cells or wounded tissue such as leaf tissue, root explants, hypocotyledons, stem pieces or tubers, for example, also are well known in the art (Glick and Thompson (eds.), *Methods in Plant Molecular Biology and Biotechnology,* Boca Raton, Fla.: CRC Press (1993), which is incorporated herein by reference). Wounded cells within the plant tissue that have been infected by Agrobacterium can develop organs de novo when cultured under the appropriate conditions; the resulting transgenic shoots eventually give rise to transgenic plants containing the exogenous nucleic acid molecule of interest, as described in Example I.

Agrobacterium-mediated transformation has been used to produce a variety of transgenic seed plants (see, for example, Wang et al. (eds), *Transformation of Plants and Soil Microorganisms,* Cambridge, UK: University Press (1995), which is incorporated herein by reference). For example, Agrobacterium-mediated transformation can be used to produce transgenic crudiferous plants such as Arabidopsis, mustard, rapeseed and flax; transgenic leguminous plants such as alfalfa, pea, soybean, trefoil and white clover; and transgenic solanaceous plants such as eggplant, petunia, potato, tobacco and tomato. In addition, Agrobacterium-mediated transformation can be used to introduce exogenous nucleic acids into apple, aspen, belladonna, black currant, carrot, celery, cotton, cucumber, grape, horseradish, lettuce, morning glory, muskmelon, neem, poplar, strawberry, sugar beet, sunflower, walnut and asparagus plants (see, for example, Glick and Thompson, supra, 1993).

Microprojectile-mediated transformation also is a well known method of introducing an exogenous nucleic acid molecule into a variety of seed plant species. This method, first described by Klein et al., Nature 327:70–73 (1987), which is incorporated herein by reference, relies on microprojectiles such as gold or tungsten that are coated with the desired nucleic acid molecule by precipitation with calcium chloride, spermidine or PEG. The microprojectile particles are accelerated at high speed into seed plant tissue using a device such as the Biolistic™ PD-1000 (Biorad, Hercules, Calif.).

Microprojectile-mediated delivery or "particle bombardment" is especially useful to transform seed plants that are difficult to transform or regenerate using other methods. Microprojectile-mediated transformation has been used, for example, to generate a variety of transgenic seed plant species, including cotton, tobacco, corn, hybrid poplar and papaya (see, for example, Glick and Thompson, supra, 1993). The transformation of important cereal crops such as wheat, oat, barley, sorghum and rice also has been achieved using microprojectile-mediated delivery (Duan et al., Nature Biotech. 14:494–498 (1996); Shimamoto, Curr. Opin. Biotech. 5:158–162 (1994), each of which is incorporated herein by reference). A rapid transformation regeneration system for the production of transgenic plants, such as transgenic wheat, in two to three months also can be useful in producing a transgenic seed plant of the invention (European Patent No. EP 0 709 462 A2, Application number 95870117.9, filed Oct. 25, 1995, which is incorporated herein by reference).

Thus, a variety of methods for introducing a nucleic acid molecule into a seed plant are well known in the art. Important crop species such as rice, for example, have been transformed using microprojectile delivery, Agrobacterium-mediated transformation or protoplast transformation (Hiei et al., The Plant J. 6(2):271–282 (1994); Shimamoto, Science 270:1772–1773 (1995), each of which is incorporated herein by reference). Fertile transgenic maize has been obtained, for example, by microparticle bombardment (see Wang et al., supra, 1995). As discussed above, barley, wheat, oat and other small-grain cereal crops also have been transformed, for example, using microparticle bombardment (see Wang et al., supra, 1995).

Methods of transforming forest trees including both angiosperms and gymnosperms also are well known in the art. Transgenic angiosperms such as members of the genus Populus, which includes aspens and poplars, have been generated using Agrobacterium-mediated transformation, for example. In addition, transgenic Populus and sweetgum, which are of interest for biomass production for fuel, also have been produced. Transgenic gymnosperms, including conifers such as white spruce and larch, also have been obtained, for example, using microprojectile bombardment (Wang et al., supra, 1995). The skilled artisan will recognize that Agrobacterium-mediated or microprojectile-mediated transformation, as disclosed herein, or other methods known in the art can be used to introduce a nucleic acid molecule encoding a floral meristem identity gene product into a seed plant according to the methods of the invention.

The term "converting shoot meristem to floral meristem," as used herein, means promoting the formation of flower progenitor tissue where shoot progenitor tissue otherwise would be formed in the angiosperm. As a result of the conversion of shoot meristem to floral meristem, flowers form in an angiosperm where shoots normally would form. The conversion of shoot meristem to floral meristem can be identified using well known methods, such as scanning electron microscopy, light microscopy or visual inspection (see, for example, Mandel and Yanofsky, Plant Cell 7:1763–1771 (1995), which is incorporated herein by reference or Weigel and Nilsson, supra, 1995).

Provided herein are methods of converting shoot meristem to floral meristem in an angiosperm by introducing a first ectopically expressible nucleic acid molecule encoding a first floral meristem identity gene product and a second ectopically expressible nucleic acid molecule encoding a second floral meristem identity gene product into the angiosperm, where the first floral meristem identity gene product is different from the second floral meristem identity gene product. As discussed above, first and second floral meristem identity gene products useful in converting shoot meristem to floral meristem in an angiosperm can be, for example, AP1 and LFY, CAL and LFY, or AP1 and CAL.

Also provided herein are methods of promoting early reproductive development in a seed plant by ectopically expressing a first nucleic acid molecule encoding a first floral meristem identity gene product in the seed plant, provided that the first nucleic acid molecule is not ectopically expressed due to a mutation in an endogenous TERMINAL FLOWER gene. For example, the invention provides a method of promoting early reproductive development in a seed plant by introducing an ectopically expressible nucleic acid molecule encoding a floral meristem identity gene product into the seed plant, thus producing a transgenic seed plant. A floral meristem identity gene product such as AP1, CAL or LFY, or a chimeric protein containing, in part, a floral meristem identity gene product, as disclosed below, is useful in methods of promoting early reproductive development.

The term "promoting early reproductive development," as used herein in reference to a seed plant, means promoting the formation of a reproductive structure earlier than the time when a reproductive structure would form on a corresponding seed plant that is grown under the same conditions and that does not ectopically express a floral meristem identity gene product. As discussed above, the time when reproductive structures form on a particular seed plant that does not ectopically express a floral meristem identity gene product is relatively fixed and depends, in part, on genetic factors as well as environmental conditions, such as day length and temperature. Thus, given a defined set of environmental conditions, a naturally occurring angiosperm, for example, will flower at a relatively fixed time. Similarly, given a defined set of environmental conditions, a naturally occurring coniferous gymnosperm, for example, will produce cones at a relatively fixed time.

As disclosed herein, ectopic expression of a nucleic acid molecule encoding a floral meristem identity gene product in an angiosperm converts shoot meristem to floral meristem in the angiosperm. Furthermore, ectopic expression of a nucleic acid molecule encoding a floral meristem identity gene product such as AP1, CAL or LFY in an angiosperm prior to the time when endogenous floral meristem identity gene products are expressed in the angiosperm can convert shoot meristem to floral meristem precociously, resulting in early reproductive development in the angiosperm, as indicated by early flowering. In the same manner, ectopic expression of a nucleic acid molecule encoding AP1, CAL, or LFY, for example, in a gymnosperm prior to the time when endogenous floral meristem identity gene products are expressed in the gymnosperm results in early reproductive development in the gymnosperm.

For a given seed plant species and particular set of growth conditions, constitutive expression of a floral meristem identity gene product results in a relatively invariant time of early reproductive development, which is the earliest time when all factors necessary for reproductive development are active. For example, as shown in Example ID, constitutive expression of AP1 in transgenic Arabidopsis plants grown under "long-day" light conditions results in early reproductive development at day 10 as compared to the normal time of reproductive development, which is day 18 in nontransgenic Arabidopsis plants grown under the same conditions. Thus, under these conditions, day 10 is the relatively invariant time of early reproductive development for Arabidopsis transgenics that constitutively express a floral meristem identity gene product.

However, in addition to methods of constitutively expressing a floral meristem identity gene product, the present invention provides methods of selecting the time of early reproductive development. As disclosed herein, floral meristem gene product expression or activity can be regulated in response to an inducing agent or cognate ligand, for example, such that the time of early reproductive development can be selected. For example, in Arabidopsis transgenics grown under the conditions described above, the time of early reproductive development need not necessarily be the relatively invariant day 10 at which early reproductive development occurs as a consequence of constitutive floral meristem identity gene product expression. If floral meristem identity gene product expression is rendered dependent upon the presence of an inducing agent, early reproductive development can be selected to occur, for example, on day 14, by contacting the seed plant with an inducing agent on or slightly before day 14.

Thus, the present invention provides recombinant nucleic acid molecules, transgenic seed plant containing such recombinant nucleic acid molecules and methods for selecting the time of early reproductive development. These methods allow a farmer or horticulturist, for example, to determine the time of early reproductive development. The methods of the invention can be useful, for example, in allowing a grower to respond to an approaching storm or impending snap-freeze by selecting the time of early reproductive development such that the crop can be harvested before being harmed by the adverse weather conditions. The methods of the invention for selecting the time of early reproductive development also can be useful to spread out the time period over which transgenic seed plants are ready to be harvested. For example, the methods of the invention can be used to increase floral meristem identity gene product expression in different crop fields at different times, resulting in a staggered time of harvest for the different fields.

Thus, the present invention provides a recombinant nucleic acid molecule containing an inducible regulatory element operably linked to a nucleic acid molecule encoding a floral meristem identity gene product. The floral meristem identity gene product encoded within a recombinant nucleic acid molecule of the invention can be, for example, AP1 or CAL. In addition, the floral meristem identity gene product encoded within a recombinant nucleic acid molecule of the invention can be LFY. As disclosed herein, a recombinant nucleic acid molecule of the invention can contain an inducible regulatory element such as a copper inducible element, tetracycline inducible element, ecdysone inducible element or heat shock inducible element.

The invention also provides a transgenic seed plant containing a recombinant nucleic acid molecule comprising an inducible regulatory element operably linked to a nucleic acid molecule encoding a floral meristem identity gene product. Such a transgenic seed plant can be an angiosperm or gymnosperm and can contain, for example, a recombinant nucleic acid molecule comprising an inducible regulatory element operably linked to a nucleic acid molecule encoding AP1 or CAL. A transgenic seed plant of the invention can contain, for example, a recombinant nucleic acid molecule comprising a copper inducible element, tetracycline inducible element, ecdysone inducible element or heat shock inducible element operably linked to a nucleic acid molecule encoding AP1. In addition, a transgenic seed plant of the invention can contain a recombinant nucleic acid molecule comprising a copper inducible element tetracycline inducible element, ecdysone inducible element or heat shock inducible element operably linked to a nucleic acid molecule encoding CAL. A transgenic seed plant of the invention also can contain a recombinant nucleic acid molecule comprising a copper inducible element, tetracycline inducible element, ecdysone inducible element or heat shock inducible element operably linked to a nucleic acid molecule encoding LFY.

The term "recombinant nucleic acid molecule," as used herein, means a non-naturally occurring nucleic acid molecule that has been manipulated in vitro such that it is genetically distinguishable from a naturally occurring nucleic acid molecule. A recombinant nucleic acid molecule of the invention comprises two nucleic acid molecules that have been manipulated in vitro such that the two nucleic acid molecules are operably linked.

As used herein, the term "inducible regulatory element" means a nucleic acid molecule that confers conditional expression upon an operably linked nucleic acid molecule, where expression of the operably linked nucleic acid molecule is increased in the presence of a particular inducing agent as compared to expression of the nucleic acid molecule in the absence of the inducing agent. In a method of the invention, a useful inducible regulatory element has the following characteristics: confers low level expression upon an operably linked nucleic acid molecule in the absence of an inducing agent; confers high level expression upon an operably linked nucleic acid molecule in the presence of an appropriate inducing agent; and utilizes an inducing agent that does not interfere substantially with the normal physiology of a transgenic seed plant treated with the inducing agent. It is recognized, for example, that, subsequent to introduction into a seed plant, a particularly useful inducible regulatory element is one that confers an extremely low level of expression upon an operably linked nucleic acid molecule in the absence of inducing agent. Such an inducible regulatory element is considered to be tightly regulated.

The term "operably linked," as used in reference to a regulatory element, such as a promoter or inducible regulatory element, and a nucleic acid molecule encoding a floral meristem identity gene product, means that the regulatory element confers regulated expression upon the operably linked nucleic acid molecule encoding the floral meristem identity gene product. Thus, the term operably linked, as used herein in reference to an inducible regulatory element and a nucleic acid molecule encoding a floral meristem identity gene product, means that the inducible regulatory element is linked to the nucleic acid molecule encoding a floral meristem identity gene product such that the inducible regulatory element increases expression of the floral meristem identity gene product in the presence of the appropriate inducing agent. It is recognized that two nucleic acid molecules that are operably linked contain, at a minimum, all elements essential for transcription, including, for example, a TATA box. One skilled in the art knows, for example, that an inducible regulatory element that lacks minimal promoter elements can be combined with a nucleic acid molecule having minimal promoter elements and a nucleic acid molecule encoding a floral meristem identity gene product such that expression of the floral meristem identity gene product can be increased in the presence of the appropriate inducing agent.

A particularly useful inducible regulatory element can be, for example, a copper-inducible promoter (Mett et al., *Proc. Natl. Acad. Sci. USA* 90:4567–4571 (1993), which is incorporated herein by reference); tetracycline-inducible regulatory element (Gatz et al., *Plant J.* 2:397–404 (1992); Röder et al., *Mol. Gen. Genet.* 243:32–38 (1994), each of which is incorporated herein by reference); ecdysone inducible element (Christopherson et al., *Proc. Natl. Acad. Sci. USA* 89:6314–6318 (1992), which is incorporated herein by reference); or heat shock inducible element (Takahashi et al., *Plant Physiol.* 99:383–390 (1992), which is incorporated herein by reference). Another useful inducible regulatory element can be a lac operon element, which is used in combination with a constitutively expressed lac repressor to confer, for example, IPTG-inducible expression, as described by Wilde et al., (*EMBO J.* 11:1251–1259 (1992), which is incorporated herein by reference).

An inducible regulatory element useful in a method of the invention also can be, for example, a nitrate-inducible promoter derived from the spinach nitrite reductase gene (Back et al., *Plant Mol. Biol.* 17:9 (1991), which is incorporated herein by reference) or a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990), each of which is incorporated herein by reference). An inducible regulatory element useful in constructing a transgenic seed plant also can be a salicylic acid inducible element (Uknes et al., *Plant Cell* 5:159–169 (1993); Bi et al., *Plant J.* 8:235–245 (1995), each of which is incorporated herein by reference) or a plant hormone-inducible element (Yamaguchi-Shinozaki et al., *Plant Mol. Biol.* 15:905 (1990); Kares et al., *Plant Mol. Biol.* 15:225 (1990), each of which is incorporated herein by reference). A human glucocorticoid response element also is an inducible regulatory element that can confer hormone-dependent gene expression in seed plants (Schena et al., *Proc. Natl. Acad. Sci. USA* 88:10421 (1991), which is incorporated herein by reference).

An inducible regulatory element that is particularly useful for increasing expression of a floral meristem identity gene product in a transgenic seed plant of the invention is a copper inducible regulatory element (see, for example, Mett et al., supra, 1993). Thus, the invention provides a recombinant nucleic acid molecule comprising a copper inducible regulatory element operably linked to a nucleic acid molecule encoding a floral meristem identity gene product and a transgenic seed plant containing such a recombinant nucleic acid molecule. Copper, which is a natural part of the nutrient environment of a seed plant, can be used to increase expression of a nucleic acid molecule encoding a floral meristem identity gene product operably linked to a copper inducible regulatory element. For example, an ACE1 binding site in conjunction with constitutively expressed yeast ACE1 protein confers copper inducible expression upon an operably linked nucleic acid molecule. The ACE1 protein, a metalloresponsive transcription factor, is activated by copper or silver ions, resulting in increased expression of a nucleic acid molecule operably linked to an ACE1 element.

Such a copper inducible regulatory element can be an ACE1 binding site from the metallothionein gene promoter (SEQ ID NO: 21; Furst et al., *Cell* 55:705–717 (1988), which is incorporated herein by reference). For example, the ACE1 binding site can be combined with the 90 base-pair domain A of the cauliflower mosaic virus 35S promoter and operably linked to a nucleic acid molecule encoding AP1, CAL or LFY to produce a recombinant nucleic acid molecule of the invention. In a transgenic seed plant constitutively expressing ACE1 under control of such a modified CaMV 35S promoter, for example, copper inducible expression is conferred upon an operably linked nucleic acid molecule encoding a floral meristem identity gene product.

The expression of a nucleic acid encoding a floral meristem identity gene product operably linked to a copper inducible regulatory element, such as 5'-AGCTTAGCGATGCGTCTTTTCCGCTGAACCGTT CCAGCAAAAAAGACTAG-3' (SEQ ID NO: 21), can be increased in a transgenic seed plant grown under copper ion-depleted conditions, for example, and contacted with 50 $\mu$M copper sulfate in a nutrient solution or with 0.5 $\mu\mu$M copper sulfate applied by foliar spraying of the transgenic seed plant (see, for example, Mett et al., supra, 1993). A single application of 0.5 $\mu$M copper sulfate can be sufficient to sustain increased floral meristem identity gene product expression over a period of several days. If desired, a transgenic seed plant of the invention also can be contacted with multiple applications of an inducing agent such as copper sulfate.

An inducible regulatory element also can confer tetracycline-dependent floral meristem identity gene expression in a transgenic seed plant of the invention. Thus, the present invention provides a recombinant nucleic acid molecule comprising a tetracycline inducible regulatory element operably linked to a nucleic acid molecule encoding a floral meristem identity gene product as well as a transgenic seed plant into which such a recombinant nucleic acid molecule has been introduced. A tetracycline inducible regulatory element is particularly useful for conferring tightly regulated gene expression as indicated by the observation that a phenotype that results from even low amounts of a gene product expression is suppressed from such an inducible system in the absence of inducing agent (see, for example, Röder et al., supra, 1994).

A transgenic seed plant constitutively expressing Tn10-encoded Tet repressor (TetR), for example, can be contacted with tetracycline to increase expression of a nucleic acid molecule encoding a floral meristem identity gene product operably linked to the cauliflower mosaic virus promoter containing several tet operator sequences (5'-ACTCTATCAGTGATAGAGT-3'; SEQ ID NO: 22) positioned close to the TATA box (see, for example, Gatz, *Meth. Cell Biol.* 50:411–424 (1995), which is incorporated herein by reference; Gatz et al., supra, 1992). Such a tetracycline-inducible system can increase expression of an operably linked nucleic acid molecule as much as 200 to 500-fold in a transgenic angiosperm or gymnosperm of the invention.

A high level of Tet repressor expression (about $1 \times 10^6$ molecules per cell) is critical for tight regulation. Thus, a seed plant preferably is transformed first with a plasmid encoding the Tet repressor, and screened for high level expression. For example, plasmid pBinTet (Gatz, supra, 1995) contains the Tet repressor coding region, which is expressed under control of the CaMV 35S promoter, and the neomycin phosphotransferase gene for selection of transformants. To screen transformants for a high level of Tet repressor expression, a plasmid containing a reporter gene under control of a promoter with tet operators, such as pTX-Gus-int (Gatz, supra, 1995), can be transiently introduced into a seed plant cell and assayed for activity in the presence and absence of tetracycline. High β-glucouronidase (GUS) expression that is dependent on the presence of tetracycline is indicative of high Tet repressor expression.

A particularly useful tetracycline inducible regulatory element is present in plasmid pBIN-HygTX, which has a CaMV 35S promoter, into which three tet operator sites have been inserted, and an octopine synthase polyadenylation site (Gatz, supra, 1995). A multiple cloning site between the promoter and polyadenylation signal in pBIN-HygTX allows for convenient insertion of a nucleic acid molecule encoding the desired floral meristem identity gene product, and the hygromycin phosphotransferase gene allows for selection of transformants containing the construct. In a preferred embodiment of the invention, previously selected Tet repressor positive cells are transformed with a plasmid such as pBIN-HygTX, into which a nucleic acid molecule encoding a floral meristem identity gene product has been inserted.

To increase floral meristem identity gene product expression using a tetracycline-inducible regulatory element, a transgenic seed plant of the invention can be contacted with tetracycline or, preferably, with chlor-tetracycline (SIGMA), which is a more efficient inducer than tetracycline. In addition, a useful inducing agent can be a tetracycline analog that binds the Tet repressor to function as an inducer but that does not act as an antibiotic (Gatz, supra, 1995). A transgenic seed plant of the invention can be contacted, for example, by watering with about 1 mg/liter chlor-tetracycline or tetracycline. Similarly, a plant grown in hydroponic culture can be contacted with a solution containing about 1 mg/liter chlor-tetracycline or tetracycline (Gatz, supra, 1995). If desired, a transgenic angiosperm or gymnosperm can be contacted repeatedly with chlor-tetracycline or tetracycline every other day for about 10 days (Röder et al., supra, 1994). Floral meristem identity gene product expression is increased efficiently at a tetracycline concentration that does not inhibit the growth of bacteria, indicating that the use of tetracycline as an inducing agent will not present environmental concerns.

An ecdysone inducible regulatory element also can be useful in practicing the methods of the invention. For example, an ecdysone inducible regulatory element can contain four copies of an ecdysone response element having the sequence 5'-GATCCGACAAGGGTTCAATGCACTTGTCA-3' (EcRE; SEQ ID NO: 23) as described in Christopherson et al., supra, 1992. In a transgenic seed plant into which a nucleic acid encoding an ecdysone receptor has been introduced, an ecdysone inducible regulatory element can confer ecdysone-dependent expression on a nucleic acid molecule encoding a floral meristem identity gene product. An appropriate inducing agent for increasing expression of a nucleic acid molecule operably linked to an ecdysone inducible regulatory element can be, for example, a-ecdysone, 20-hydroxyecdysone, polypodine B, ponasterone A, muristerone A or RH-5992, which is an ecdysone agonist that mimics 20-hydroxyecdysone (see, for example, Kreutzweiser et al., *Ecotoxicol. Environ. Safety* 28:14–24 (1994), which is incorporated herein by reference and Christopherson et al., supra, 1992). Methods for determining an appropriate inducing agent for use with an ecdysone inducible regulatory element are well known in the art. As disclosed herein, compound RH-5992 can be a particularly useful inducing agent for increasing floral meristem gene product expression in a transgenic seed plant containing an ecdysone inducible regulatory element.

An inducible regulatory element also can be derived from the promoter of a heat shock gene, such as HSP81-1 (SEQ ID NO: 24; Takahashi, supra, 1992). Thus, the invention also provides a recombinant nucleic acid molecule comprising a heat shock inducible regulatory element operably linked to a nucleic acid molecule encoding a floral meristem identity gene product and a transgenic seed plant containing such a recombinant nucleic acid molecule. The HSP81-1 promoter (SEQ ID NO: 24) confers low level expression upon an operably linked nucleic acid molecule in parts of roots under unstressed conditions and confers high level expression in most Arabidopsis tissues following heat shock (see, for example, Yabe et al., *Plant Cell Physiol.* 35:1207–1219 (1994), which is incorporated herein by reference). After growth of Arabidopsis at 23° C., a single heat shock treatment at 37° C. for two hours is sufficient to induce expression of a nucleic acid molecule operably linked to the HSP81-1 gene regulatory element (see Ueda et al., *Mol. Gen. Genet.* 250:533–539 (1996), which is incorporated herein by reference).

The use of a heat shock inducible regulatory element is particularly useful for a transgenic seed plant of the invention grown in an enclosed environment such as a green house, where temperature can be readily manipulated. The use of a heat shock inducible regulatory element especially is applicable to a transplantable or potted transgenic seed plant of the invention, which can be moved conveniently from an environment having a low temperature to an environment having a high temperature. A transgenic angiosperm or gymnosperm of the invention containing a recombinant nucleic acid molecule comprising a HSP81-1 heat shock regulatory element operably linked to a nucleic acid molecule encoding a floral meristem identity gene product also can be induced, for example, by altering the ambient temperature, watering with heated water or submersing the transgenic seed plant in a sealed plastic bag into a heated water bath (see, for example, Ueda et al., supra, 1996).

A recombinant nucleic acid molecule of the invention comprising an inducible gene regulatory element can be expressed variably in different lines of transgenic seed plants. In some transgenic lines, for example, leaky expression of the introduced recombinant nucleic acid molecule can occur in the absence of the appropriate inducing agent due to phenomena such as position effects (see, for example, Ueda et al., supra, 1996). Thus, a transgenic seed plant containing a recombinant nucleic acid molecule comprising an inducible gene regulatory element operably linked to a nucleic acid encoding a floral meristem identity gene product can be screened, if desired, to obtain a particular transgenic seed plant in which expression of the operably linked nucleic acid molecule is desirably low in the absence of the appropriate inducing agent.

The present invention also provides a method of converting shoot meristem to floral meristem in an angiosperm by introducing into the angiosperm a recombinant nucleic acid molecule comprising an inducible regulatory element operably linked to a nucleic acid molecule encoding a floral meristem identity gene product to produce a transgenic angiosperm, and contacting the transgenic angiosperm with an inducing agent, thereby increasing expression of the floral meristem identity gene product and converting shoot meristem to floral meristem in the transgenic angiosperm. In such a method of the invention, the inducible regulatory element can be, for example, a copper inducible element, tetracycline inducible element, ecdysone inducible element or heat shock inducible element, and the floral meristem identity gene product can be, for example, AP1, CAL or LFY.

In addition, the invention provides a method of promoting early reproductive development in a seed plant such as an angiosperm or gymnosperm by introducing into the seed plant a recombinant nucleic acid molecule comprising an inducible regulatory element operably linked to a nucleic acid molecule encoding a floral meristem identity gene product to produce a transgenic seed plant, and contacting the transgenic seed plant with an inducing agent, thereby increasing expression of the floral meristem identity gene product and promoting early reproductive development in the transgenic seed plant. In a method of the invention for promoting early reproductive development in a seed plant, the inducible regulatory element can be, for example, a copper inducible element, tetracycline inducible element, ecdysone inducible element or heat shock inducible element, and the floral meristem identity gene product can be, for example, AP1, CAL or LFY.

The term "inducing agent," as used herein, means a substance or condition that effects increased expression of a nucleic acid molecule operably linked to a particular inducible regulatory element as compared to the level of expression of the nucleic acid molecule in the absence of the inducing agent. An inducing agent can be, for example, a naturally occurring or synthetic chemical or biological molecule such as a simple or complex organic molecule, a peptide, a protein or an oligonucleotide that increases expression of a nucleic acid molecule operably linked to a particular inducible regulatory element. An example of such an inducing agent is a compound such as copper sulfate, tetracycline or an ecdysone. An inducing agent also can be a condition such as heat of a certain temperature or light of a certain wavelength. When used in reference to a particular inducible regulatory element, an "appropriate" inducing agent means an inducing agent that results in increased expression of a nucleic acid molecule operably linked to the particular inducible regulatory element.

An inducing agent of the invention can be used alone or in solution or can be used in conjunction with an acceptable carrier that can serve to stabilize the inducing agent or to promote absorption of the inducing agent by a seed plant. If desired, a transgenic seed plant of the invention can be contacted with an inducing agent in combination with an unrelated substance such as a plant nutrient, pesticide or insecticide.

One skilled in the art can readily determine the optimum concentration of an inducing agent needed to produce increased expression of a nucleic acid molecule operably linked to an inducible regulatory element in a transgenic seed plant of the invention. For conveniently determining the optimum concentration of inducing agent from a range of useful concentrations, one skilled in the art can operably link the particular inducible regulatory element to a nucleic acid molecule encoding a reporter gene product such as β-glucouronidase (GUS) and assay for reporter gene product activity in the presence of various concentrations of inducing agent (see, for example, Jefferson et al., *EMBO J.* 6:3901–3907 (1987), which is incorporated herein by reference).

As used herein, the term "contacting," in reference to a transgenic seed plant of the invention, means exposing the transgenic seed plant to an inducing agent, or to a cognate ligand as disclosed below, such that the agent can induce expression of a nucleic acid molecule operably linked to the particular inducible regulatory element. A transgenic seed plant such as an angiosperm or gymnosperm, which contains a recombinant nucleic acid molecule of the invention, can be contacted with an inducing agent in a variety of manners. Expression of a floral meristem identity gene product can be increased conveniently, for example, by spraying a transgenic seed plant with an aqueous solution containing an appropriate inducing agent or by adding an appropriate inducing agent to the water supply of a transgenic seed plant grown using irrigation or to the water supply of a transgenic seed plant grown hydroponically. A transgenic seed plant containing a recombinant nucleic acid molecule of the invention also can be contacted by spraying the seed plant with an inducing agent in aerosol form. In addition, a transgenic seed plant can be contacted with an appropriate inducing agent by adding the agent to the soil or other solid nutrient media in which the seed plant is grown, whereby the inducing agent is absorbed into the seed plant. Other modes of contacting a transgenic seed plant with an inducing agent, such as injecting or immersing the seed plant in a solution containing an inducing agent, are well known in the art. For an inducing agent that is temperature or light, for example, contacting can be effected by altering the temperature or light to which the transgenic seed plant is exposed, or, if desired, by moving the transgenic seed plant from an environment of one temperature or light source to an environment having the appropriate inducing temperature or light source.

If desired, a transgenic seed plant of the invention can be contacted individually with an inducing agent. Furthermore, a group of transgenic seed plants that, for example, are located together in a garden plot, hot house or field, can be contacted en masse with an inducing agent, such that floral meristem identity gene product expression is increased coordinately in all transgenic seed plants of the group.

A transgenic seed plant of the invention can be contacted with an inducing agent using one of several means. For example, a transgenic seed plant can be contacted with an inducing agent by non-automated means such as with a hand held spraying apparatus. Such manual means can be useful when the methods of the invention are applied to particularly delicate or valuable seed plant varieties or when it is desirable, for example, to promote early reproductive development in a particular transgenic seed plant without promoting early reproductive development in a neighboring transgenic seed plant. Furthermore, a transgenic seed plant of the invention can be contacted with an inducing agent by mechanical means such as with a conventional yard "sprinkler" for a transgenic seed plant grown, for example, in a garden; a mechanical spraying system in a green house; traditional farm machinery for spraying field crops; or "crop dusting" for conveniently contacting an entire field of transgenic seed plants with a particulate or gaseous inducing agent. The skilled practitioner, whether home gardener or commercial farmer, recognizes that these and other manual or mechanical means can be used to contact a transgenic seed plant with an inducing agent according to the methods of the invention.

Furthermore, it is recognized that a transgenic seed plant of the invention can be contacted with a single treatment of an inducing agent or, if desired, can be contacted with multiple applications of the inducing agent. In a preferred embodiment of the invention, a transgenic seed plant of the invention is contacted once with an inducing agent to effectively increase floral meristem identity gene product expression, thereby promoting early reproductive development in the transgenic seed plant. Similarly, a transgenic angiosperm of the invention preferably is contacted once with an inducing agent to effectively increase floral meristem identity gene product expression and convert shoot meristem to floral meristem in the transgenic angiosperm.

A single application of an inducing agent is preferable when a transient increase in floral meristem identity gene product expression from a recombinant nucleic acid molecule of the invention promotes irreversible early reproductive development in a seed plant. In many seed plant species, early reproductive development is irreversible. Transient expression of a floral meristem identity gene product from an introduced recombinant nucleic acid molecule, for example, results in sustained ectopic expression of endogenous floral meristem identity gene products, resulting in irreversible early reproductive development. For example, ectopic expression of AP1 in a transgenic plant induces endogenous LFY gene expression, and ectopic expression of LFY induces endogenous AP1 gene expression (Mandel and Yanofsky, *Nature* 377:522–524 (1995), which is incorporated herein by reference; Weigel and Nilsson, supra, 1995). Genetic studies also indicate that CAL can act directly or indirectly to increase expression of AP1 and LFY. Thus, ectopic expression of CAL from an exogenous nucleic acid molecule, for example, can induce endogenous AP1 and LFY expression (see Bowman et al., supra, 1993). Enhanced expression of endogenous AP1, LFY or CAL following a transient increase in expression of an introduced floral meristem identity gene product induced by a single application of an inducing agent can make repeated applications of an inducing agent unnecessary.

In some seed plants, however, such as angiosperms characterized by the phenomenon of floral reversion, repeated applications of the inducing agent can be desirable. In species such as impatiens, an initiated flower can revert into a shoot such that the center of the developing flower behaves as an indeterminate shoot (see, for example, Battey and Lyndon, *Ann. Bot.* 61:9–16 (1988), which is incorporated by reference herein). Thus, to prevent floral reversion in species such as impatiens, repeated applications of an inducing agent can be useful. Repeated applications of an inducing agent, as well as single applications, are encompassed within the scope of the present invention.

The invention further provides a nucleic acid molecule encoding a chimeric protein, which comprises a nucleic acid molecule encoding a floral meristem identity gene product such as AP1, CAL or LFY linked in frame to a nucleic acid molecule encoding a ligand binding domain. Expression of a chimeric protein of the invention in a seed plant is useful because the ligand binding domain renders the activity of a linked gene product dependent on the presence of cognate ligand. Specifically, in a chimeric protein of the invention, floral meristem gene product activity is increased in the presence of cognate ligand, as compared to activity in the absence of cognate ligand.

A nucleic acid molecule encoding a chimeric protein of the invention comprises a nucleic acid molecule encoding a floral meristem identity gene product, such as a nucleic acid molecule having the nucleic acid sequence SEQ ID NO: 1, SEQ ID NO: 9 or SEQ ID NO: 15, which encodes AP1, CAL or LFY, respectively, any of which is linked in frame to a nucleic acid molecule encoding a ligand binding domain. The expression of such a nucleic acid molecule results in the production of a chimeric protein containing a floral meristem identity gene product fused to a ligand binding domain. Thus, the invention also provides a chimeric protein containing a floral meristem identity gene product fused to a ligand binding domain and an antibody that specifically binds such a chimeric protein.

The invention further provides a transgenic seed plant, such as angiosperm or gymnosperm, that contains a nucleic acid molecule encoding a chimeric protein of the invention. The invention provides, for example, a transgenic seed plant containing a nucleic acid molecule encoding a chimeric protein, which comprises a nucleic acid molecule encoding AP1, CAL or LFY linked in frame to a nucleic acid molecule encoding a ligand binding domain. A particularly useful transgenic seed plant contains a nucleic acid molecule encoding AP1 linked in frame to a nucleic acid molecule encoding an ecdysone receptor ligand binding domain or a glucocorticoid receptor ligand binding domain. The invention also provides a transgenic seed plant containing a nucleic acid molecule encoding a chimeric protein, which comprises a nucleic acid molecule encoding CAL linked in frame to a nucleic acid molecule encoding an ecdysone receptor ligand binding domain or a glucocorticoid receptor ligand binding domain. In addition, there is provided a transgenic seed plant containing a nucleic acid molecule encoding a chimeric protein, which comprises a nucleic acid molecule encoding LFY linked in frame to a nucleic acid molecule encoding an ecdysone receptor ligand binding domain or a glucocorticoid receptor ligand binding domain.

Any floral meristem identity gene product, as defined herein, is useful in a chimeric protein of the invention. Thus, a nucleic acid molecule encoding *Arabidopsis thaliana* AP1 (SEQ ID NO: 2), *Brassica oleracea* AP1 (SEQ ID NO: 4), *Brassica oleracea* var. *Botrytis* AP1 (SEQ ID NO: 8) or *Zea mays* AP1 (SEQ ID NO: 10), each of which have activity in converting shoot meristem to floral meristem, can be used to construct a nucleic acid molecule encoding a chimeric protein of the invention. Similarly, a nucleic acid molecule encoding, for example, *Arabidopsis thaliana* CAL (SEQ ID NO: 10), *Brassica oleracea* CAL (SEQ ID NO: 12), or a nucleic acid molecule encoding *Arabidopsis thaliana* LFY (SEQ ID NO: 16) is useful when linked in frame to a nucleic acid molecule encoding a ligand binding domain to produce a nucleic acid molecule encoding a ligand-dependent chimeric protein of the invention.

A ligand binding domain useful in a chimeric protein of the invention is a domain that, when fused in frame to a heterologous gene product, renders the activity of the fused gene product dependent on cognate ligand such that the activity of the fused gene product is increased in the presence of cognate ligand as compared to its activity in the absence of ligand. Such a ligand binding domain can be a steroid binding domain such as the ligand binding domain of an ecdysone receptor, glucocorticoid receptor, estrogen receptor, progesterone receptor, androgen receptor, thyroid receptor, vitamin D receptor or retinoic acid receptor. A particularly useful ligand binding domain is the ecdysone receptor ligand binding domain contained within amino acids 329 to 878 of the Drosophila ecdysone receptor (SEQ ID NO: 18); Koelle et al., *Cell* 67:59–77 (1991); Thummel, *Cell* 83:871–877 (1995), each of which is incorporated herein by reference) or a glucocorticoid receptor ligand binding domain, encompassed, for example, within amino acids 512 to 795 of the rat glucocorticoid receptor (SEQ ID NO: 20; Miesfeld et al., *Cell* 46:389–399 (1986), which is incorporated herein by reference).

A chimeric protein of the invention containing an ecdysone receptor ligand binding domain has floral meristem identity gene product activity that can be increased in the presence of ecdysone ligand. Similarly, a chimeric protein of the invention containing a glucocorticoid receptor ligand binding domain has floral meristem identity gene product activity that is increased in the presence of glucocorticoid ligand. It is well known that in a chimeric protein containing a heterologous gene product such as adenovirus E1A, c-myc, c-fos, the HIV-1 Rev transactivator, MyoD or maize regulatory factor R fused to the rat glucocorticoid receptor ligand binding domain, activity of the fused heterologous gene product can be increased by glucocorticoid ligand (Eilers et al., *Nature* 340:66 (1989); Superti-Furga et al., *Proc. Natl. Acad. Sci., U.S.A.* 88:5114 (1991); Hope et al., *Proc. Natl. Acad. Sci., U.S.A.* 87:7787 (1990); Hollenberg et al., *Proc. Natl. Acad. Sci., U.S.A.* 90:8028 (1993), each of which is incorporated herein by reference).

A nucleic acid molecule encoding a chimeric protein of the invention can be introduced into a seed plant where, under appropriate conditions, the chimeric protein is expressed. In such a transgenic seed plant, floral meristem identity gene product activity can be increased by contacting the transgenic seed plant with cognate ligand. For example, activity of a heterologous protein fused to a rat glucocorticoid receptor ligand binding domain (amino acids 512 to 795) expressed under the control of the constitutive cauliflower mosaic virus 35S promoter in Arabidopsis was low in the absence of glucocorticoid ligand; whereas, upon contacting the transformed plants with a synthetic glucocorticoid, dexamethasone, activity of the protein was increased greatly (Lloyd et al., *Science* 266:436–439 (1994), which is incorporated herein by reference). As disclosed herein, a ligand binding domain fused to a floral meristem identity gene product renders the activity of a fused floral meristem identity gene product ligand-dependent such that, upon contacting the transgenic seed plant with cognate ligand, floral meristem identity gene product activity is increased.

Methods for constructing a nucleic acid molecule encoding a chimeric protein of the invention are routine and well known in the art (Sambrook et al., supra, 1989). Methods of constructing, for example, a nucleic acid encoding an AP1-glucocorticoid receptor ligand binding domain chimeric protein are described in Example IV. For example, the skilled artisan recognizes that a stop codon encoded by the nucleic acid molecule must be removed and that the two nucleic acid molecules must be linked in frame such that the reading frame of the 3' nucleic acid molecule coding sequence is preserved. Methods of transforming a seed plant such as an angiosperm or gymnosperm with a nucleic acid molecule are disclosed above and well known in the art (see Examples I, II and III; see, also, Mohoney et al., U.S. Pat. No. 5,463,174, and Barry et al., U.S. Pat. No. 5,463,175, each of which is incorporated herein by reference).

As used herein, the term "linked in frame," when used in reference to two nucleic acid molecules that make up a nucleic acid molecule encoding a chimeric protein, means that the two nucleic acid molecules are linked in the correct reading frame such that, under appropriate conditions, a full-length chimeric protein is expressed. In particular, a 5' nucleic acid molecule, which encodes the amino-terminal portion of the chimeric protein, must be linked to a 3' nucleic acid molecule, which encodes the carboxyl-terminal portion of the chimeric protein, such that the carboxyl-terminal portion of the chimeric protein is translated in the correct reading frame. One skilled in the art would recognize that a nucleic acid molecule encoding a chimeric protein of the invention can comprise, for example, a 5' nucleic acid molecule encoding a floral meristem identity gene product linked in frame to a 3' nucleic acid molecule encoding a ligand binding domain or can comprise a 5' nucleic acid molecule encoding a ligand binding domain linked in frame to a 3' nucleic acid molecule encoding a floral meristem identity gene product. Preferably, a nucleic acid molecule encoding a chimeric protein of the invention comprises a 5' nucleic acid molecule encoding a floral meristem identity gene product linked in frame to a 3' nucleic acid molecule encoding a ligand binding domain.

In a transgenic angiosperm containing a chimeric protein of the invention, conversion of shoot meristem to floral meristem can be induced by contacting the transgenic angiosperm with a cognate ligand that is absorbed by the angiosperm and binds the chimeric protein within its ligand binding domain. Thus, the present invention provides a method of converting shoot meristem to floral meristem in an angiosperm by introducing into the angiosperm a nucleic acid molecule encoding a chimeric protein to produce a transgenic angiosperm, where, under appropriate conditions, the chimeric protein containing a floral meristem identity gene product fused to a ligand binding domain is expressed; and contacting the transgenic angiosperm with cognate ligand, where, upon binding of the cognate ligand to the ligand binding domain, floral meristem identity gene product activity is increased, thereby converting shoot meristem to floral meristem in the transgenic angiosperm.

The present invention provides, for example, a method of converting shoot meristem to floral meristem in an angiosperm by introducing into the angiosperm a nucleic acid molecule encoding a chimeric protein, which comprises a nucleic acid molecule encoding AP1, CAL or LFY linked in frame to a nucleic acid molecule encoding an ecdysone receptor ligand binding domain, to produce a transgenic angiosperm, where, under appropriate conditions, the chimeric protein is expressed; and contacting the transgenic angiosperm with ecdysone ligand, where, upon binding of the ecdysone ligand to the ecdysone receptor ligand binding domain, floral meristem identity gene product activity is increased, thereby converting shoot meristem to floral meristem in the transgenic angiosperm. Similarly, the invention provides, for example, a method of converting shoot meristem to floral meristem in an angiosperm by introducing into the angiosperm a nucleic acid molecule encoding a chimeric protein, which comprises a nucleic acid molecule encoding AP1, CAL or LFY linked in frame to a nucleic acid molecule encoding a glucocorticoid receptor ligand binding domain, to produce a transgenic angiosperm, where, under appropriate conditions, the chimeric protein is expressed; and contacting the transgenic angiosperm with glucocorticoid ligand, where, upon binding of the glucocorticoid ligand to the glucocorticoid receptor ligand binding domain, floral meristem identity gene product activity is increased, thereby converting shoot meristem to floral meristem in the transgenic angiosperm.

In addition, the invention provides a method of promoting early reproductive development in a seed plant by introducing into the seed plant a nucleic acid molecule encoding a chimeric protein of the invention to produce a transgenic seed plant, where, under appropriate conditions, the chimeric protein containing a floral meristem identity gene product fused to a ligand binding domain is expressed; and contacting the transgenic seed plant with cognate ligand, where, upon binding of the cognate ligand to the ligand binding domain, floral meristem identity gene product activity is increased, thereby promoting early reproductive development in the transgenic seed plant. The methods of the invention can be practiced with numerous seed plant varieties. The seed plant can be, for example, an angiosperm such as a cereal plant, leguminous plant, hardwood tree or coffee plant, or can be a gymnosperm such as a pine, fir, spruce or redwood tree.

There is provided, for example, a method of promoting early reproductive development in a seed plant by introducing into the seed plant a nucleic acid molecule encoding a chimeric protein, which comprises a nucleic acid molecule encoding a floral meristem identity gene product linked in frame to a nucleic acid molecule encoding an ecdysone receptor ligand binding domain, to produce a transgenic seed plant, where, under appropriate conditions, the chimeric protein is expressed; and contacting the transgenic seed plant with ecdysone ligand, where, upon binding of the ecdysone ligand to the ecdysone receptor ligand binding domain, floral meristem identity gene product activity is increased, thereby promoting early reproductive development in the transgenic seed plant. Similarly, the invention provides, for example, a method of promoting early reproductive development in a seed plant by introducing into the seed plant a nucleic acid molecule encoding a chimeric protein, which comprises a nucleic acid molecule encoding AP1, CAL or LFY linked in frame to a nucleic acid molecule encoding a glucocorticoid receptor ligand binding domain, to produce a transgenic seed plant, where, under appropriate conditions, the chimeric protein is expressed; and contacting the transgenic seed plant with glucocorticoid ligand, where, upon binding of the glucocorticoid ligand to the glucocorticoid receptor ligand binding domain, floral meristem identity gene product activity is increased, thereby promoting early reproductive development in the transgenic seed plant.

As used herein, the term "ligand" means a naturally occurring or synthetic chemical or biological molecule such as a simple or complex organic molecule, a peptide, a protein or an oligonucleotide that specifically binds a ligand binding domain. In the methods of the present invention, a ligand can be used alone or in solution or can be used in conjunction with an acceptable carrier that can serve to stabilize the ligand or promote absorption of the ligand by a seed plant. If desired, a transgenic seed plant of the invention can be contacted with a ligand for increasing floral meristem identity gene product activity in combination with an unrelated molecule such as a plant nutrient, pesticide or insecticide. When used in reference to a particular ligand binding domain, the term "cognate ligand" means a ligand that, under suitable conditions, specifically binds the particular ligand binding domain.

One skilled in the art readily can determine the optimum concentration of cognate ligand needed to bind a ligand binding domain and increase floral meristem identity gene product activity in a transgenic seed plant of the invention. Generally, a concentration of about 1 nM to 10 $\mu$M cognate ligand is useful for increasing floral meristem identity gene product activity in a transgenic seed plant expressing a chimeric protein of the invention. Preferably, a concentration of about 100 nM to 1 $\mu$M cognate ligand is useful for increasing floral meristem identity gene product activity in a transgenic seed plant containing a chimeric protein of the invention (see, for example, Christopherson et al., *Proc. Natl. Acad. Sci. USA* 89:6314–6318 (1992), which is incorporated herein by reference; also, see Lloyd et al., supra, 1994). For example, a concentration of about 100 nM to 1 $\mu$M dexamethasone can be useful for increasing floral meristem identity gene product activity in a transgenic seed plant of the invention containing a nucleic acid molecule encoding a chimeric protein, which comprises a nucleic acid molecule encoding a floral meristem identity gene product, such as AP1 or CAL, linked in frame to a nucleic acid molecule encoding a glucocorticoid receptor ligand binding domain, as described in Example IV.

As discussed above, a transgenic seed plant of the invention, such as a transgenic seed plant expressing a chimeric protein of the invention, can be contacted in a variety of manners. A transgenic seed plant can be contacted with cognate ligand, for example, by spraying the seed plant with a gaseous ligand or with solution such as an aqueous solution containing the appropriate ligand; or by adding the cognate ligand to the water supply of a seed plant grown using irrigation or grown hydroponically; or by adding the cognate ligand to the soil or other solid nutrient medium in which a seed plant is grown, whereby the cognate ligand is absorbed into the seed plant to increase floral meristem identity gene product activity. A transgenic seed plant expressing a chimeric protein of the invention also can be contacted with a cognate ligand in aerosol form. In addition, a transgenic seed plant can be contacted with cognate ligand by injecting the seed plant or by immersing the seed plant in a solution containing the cognate ligand.

A transgenic seed plant expressing a chimeric protein of the invention can be contacted individually with cognate ligand, or a group of transgenic seed plants can be contacted en masse to increase floral meristem gene product activity synchronously in all seed plants of the group. Furthermore, a variety of means can be used to contact a transgenic seed plant of the invention with cognate ligand to increase floral meristem identity gene product activity. A transgenic seed plant can be contacted with cognate ligand using, for example, a hand held spraying apparatus; conventional yard "sprinkler"; mechanical spraying system, such as an overhead spraying system in a green house; traditional farm machinery, or "crop dusting." As discussed above in regard to the application of inducing agents, the methods of the invention can be practiced using these and other manual or mechanical means to contact a transgenic seed plant with single or multiple applications of cognate ligand.

The nucleic acid molecules encoding floral meristem identity gene products provided herein also can be useful in generating sterile transgenic seed plants and in methods of producing reproductive sterility in seed plants. The methods of the invention involve cosuppression metholodology, where a nucleic acid molecule in the sense orientation is introduced into a seed plant to suppress expression of a homologous endogenous gene, or involve antisense metholodology. Thus, the present invention provides cosuppression and antisense methods of producing reproductively sterile transgenic seed plants as well as the two types of sterile transgenic seed plants produced by these methods.

A method of the invention for producing a reproductively sterile transgenic seed plant has a variety of uses including safely growing transgenic trees in close contact with interfertile wild trees, increasing wood production and reducing allergenic pollen production. A method for producing reproductive sterility in seed plants, which is useful for transgene containment, can allow, for example, the introduction of transgenic trees into the environment. Of particular concern to the introduction of transgenic trees into the environment is the possibility of enhanced "weediness" or the movement of transgenes by cross-fertilization into gene pools of wild relatives. Most commercially grown forest trees, for example, are grown in close proximity to interfertile wild populations, and gene flow within and among tree populations usually is extensive, making the probability of transgene escape from plantations of fertile transgenic trees high.

Regulatory agencies have based approval of transgenic tree planting on sexual isolation of the transgenic species; for example, approval of two field tests for transgenic poplars by the Animal and Plant Health Inspection Service (APHIS) was contingent on the trees not being allowed to flower (see, for example, Strauss et al., *Molec. Breed* 1:5–26 (1995), which is incorporated herein by reference). Thus, transgene containment through, for example, the use of sterile transgenic trees is central to the usefulness of improved transgenic varieties.

Methods of producing reproductively sterile seed plants also can be useful for increasing wood production, since substantial energy and nutrients are committed to reproductive development in trees. For example, in trees such as radiata pine, white spruce, balsam fir and Douglas fir, reduced growth, as measured by height or stem volume, is correlated with the early production of cones (Strauss et al., supra, 1995). Thus, the methods of the invention, which prevent flowering or cone development, for example, by producing reproductive sterility, are useful for growing substantially larger trees, thus increasing wood production.

A method for producing reproductively sterile seed plants also can be useful for alleviating allergies caused by tree pollen. For example, in Japan many people suffer from allergies caused by the most commonly planted forest tree, the conifer sugi (Strauss et al., supra, 1995). The methods of the invention, therefore, can be advantageous for preventing pollen formation in seed plants such as the conifer sugi.

Cosuppression, which relies on expression of a nucleic acid molecule in the sense orientation, is a well known methodology that produces coordinate silencing of the introduced nucleic acid molecule and the homologous endogenous gene (see, for example, Flavell, *Proc. Natl. Acad. Sci., USA* 91:3490–3496 (1994), which is incorporated herein by reference; Kooter and Mol, supra, 1993). Although the mechanism of cosuppression is unknown, cosuppression is induced most strongly by a large number of transgene copies or by overexpression of transgene RNA; cosuppression also can be enhanced by modification of the transgene such that it fails to be translated. Cosuppression has been used successfully to produce sterile plants; for example, a sense nucleic acid molecule containing a full-length fbp1 coding sequence under control of the strong CaMV 35S promoter has been introduced into petunia. Two of twenty-one transformants exhibited an abnormal phenotype and contained multiple copies of the fbp1 transgene. Furthermore, fbp1 expression was undetectable in these sterile transgenic plants, indicating that expression of endogenous fbp1 was suppressed (Angenent et al., *The Plant Journal* 4:101–112 (1993), which is incorporated herein by reference).

Antisense nucleic acid molecules, which can act by reducing mRNA translation or by increasing mRNA degradation, for example, also can suppress gene expression of diverse genes and seed plant species (see, for example, Kooter and Mol, *Current Opin. Biol.* 4:166–171 (1993), which is incorporated herein by reference; see also Strauss et al., supra, 1995). Antisense nucleic acid molecules previously have been used to successfully suppress the expression of a homologous endogenous gene, thereby generating sterile plants. For example, an antisense chalcone synthase gene under control of the CaMV 35S promoter with an anther-specific enhancer sequence effectively suppressed endogenous chalcone synthase expression levels, resulting in male sterility in transgenic petunia plants (van der Meer et al., *The Plant Cell* Vol 4:253–262 (1992), which is incorporated herein by reference). Similarly, the full-length tomato TM5 MADS box gene, when placed in antisense orientation under control of the CaMV 35S promoter, was used to produce sterile transgenic tomato plants (Pnuell et al., *The Plant Cell* Vol. 6, 175–186 (1994), which is incorporated herein by reference). Antisense nucleic acid molecules encoding floral meristem identity gene products similarly can be used to produce reproductive sterility in seed plants; however, by preventing reproductive development at the earliest stage, the methods of the invention result in an advantageous energy savings.

Thus, the present invention provides a sterile transgenic seed plant such as an angiosperm or gymnosperm containing one or more sense or antisense nucleic acid molecules encoding a floral meristem identity gene product, or a fragment thereof, such that expression of AP1 and LFY gene products, including expression of endogenous AP1 and LFY gene products, is suppressed in the transgenic seed plant. The invention also provides, for example, a sterile transgenic seed plant containing a sense or antisense nucleic acid molecule encoding AP1, or a fragment thereof; a sense or antisense nucleic acid molecule encoding CAL, or a fragment thereof; and a sense or antisense nucleic acid molecule encoding LFY, or a fragment thereof, such that expression of AP1 and LFY gene products, including expression of endogenous AP1 and LFY gene products, is suppressed in the transgenic seed plant. The invention further provides a sterile transgenic seed plant containing a sense or antisense nucleic acid molecule encoding AP1, or a fragment thereof, and a sense or antisense nucleic acid molecule encoding LFY, or a fragment thereof, such that expression of AP1 and LFY gene products, including expression of endogenous AP1 and LFY gene products, is suppressed in the transgenic seed plant.

The present invention also provides methods of producing reproductive sterility in a seed plant such as a tree by introducing into a seed plant one or more sense or antisense nucleic acid molecules encoding a floral meristem identity gene product, or a fragment thereof, to produce a transgenic seed plant, such that expression of AP1 and LFY gene products, including expression of endogenous AP1 and LFY gene products, is suppressed in the transgenic seed plant. In a preferred embodiment of the invention, there are provided methods of producing reproductive sterility in a seed plant by introducing into a seed plant a sense or antisense nucleic acid molecule encoding AP1, or a fragment thereof; a sense or antisense nucleic acid molecule encoding CAL, or a fragment thereof; and a sense or antisense nucleic acid molecule encoding LFY, or a fragment thereof, to produce a transgenic seed plant, such that expression of AP1 and LFY gene products, including expression of endogenous AP1 and LFY gene products, is suppressed in the transgenic seed plant. In another embodiment, the invention provides methods of producing reproductive sterility in a seed plant by introducing into a seed plant a sense or antisense nucleic acid molecule encoding AP1, or a fragment thereof, and a sense or antisense nucleic acid molecule encoding LFY, or a fragment thereof, to produce a transgenic seed plant, such that expression of AP1 and LFY gene products, including expression of endogenous AP1 and LFY gene products, is suppressed in the transgenic seed plant.

Sterile seed plants that lack expression of functional AP1 and LFY gene products have been described previously. For example, a non-flowering Arabidopsis lfy ap1 double mutant has been described in which flowers were transformed into shoot-like structures (see, for example, Bowman et al., supra, 1993, and Weigel, supra, 1995). However, in contrast to previously described methods of generating sterile seed plants using mutagenesis, a methodology that is cumbersome or unfeasible in higher plants, the present invention provides a convenient method of producing reproductive sterility in a seed plant using sense or antisense nucleic acid molecules encoding floral meristem identity gene products.

The methods of the invention for producing reproductive sterility rely upon introducing into a seed plant one or more sense or antisense nucleic acid molecules encoding a floral meristem identity gene product, or a fragment thereof, such that expression of AP1 and LFY gene products, including expression of endogenous AP1 and LFY gene products, is suppressed in the transgenic seed plant. The skilled artisan will recognize that effective suppression of endogenous AP1 and LFY gene product expression depends upon the one or more introduced nucleic acid molecules having a high percentage of homology with the corresponding endogenous gene loci.

The homology requirement for effective suppression using sense or antisense nucleic acid molecules can be determined empirically. In general, a minimum of about 80–90% nucleic acid sequence identity is preferred for effective suppression of endogenous floral meristem identity gene product expression. Thus, a nucleic acid molecule encoding a gene ortholog from the family or genus of the seed plant species into which the nucleic acid molecule is to be introduced is preferable in practicing the methods of the invention. More preferably, a nucleic acid molecule encoding a gene ortholog from the same seed plant species into which the nucleic acid molecule is to be introduced is used in the methods of the invention. Although a highly homologous nucleic acid molecule is preferred in the methods of the invention, the sense or antisense nucleic acid molecule need not contain the entire coding sequence of the floral meristem identity gene sequence to be suppressed. Thus, a sense or antisense nucleic acid molecule encoding only a fragment of AP1, CAL or LFY coding sequence, for example, also can be useful in the methods of the invention.

As used herein in reference to a nucleic acid molecule encoding a floral meristem identity gene product, the terms "sense" and "antisense" have their commonly understood meanings.

As used herein in reference to a nucleic acid molecule encoding a floral meristem identity gene product, the term "fragment" means a portion of the nucleic acid sequence containing at least about 50 base pairs to the full-length of the nucleic acid molecule encoding the floral meristem identity gene product. In contrast to an active fragment, as defined herein, a fragment of a nucleic acid molecule encoding a floral meristem identity gene product need not encode a functional portion of a gene product.

In the methods of the invention for producing reproductive sterility, the sense or antisense nucleic acid molecule is expressed under control of a strong promoter that is expressed, at least in part, in floral meristem. The constitutive cauliflower mosaic virus 35S promoter (Odell et al., supra, 1985), for example, or other strong promoters as disclosed herein, can be useful in the methods of the invention. In addition, an RNA polymerase III promoter can be useful in methods of producing reproductive sterility using an antisense nucleic acid molecule (see, for example, Bourque and Folk, *Plant Mol. Biol.* 19:641–647 (1992), which is incorporated herein by reference).

The present invention also provides novel substantially purified nucleic acid molecules encoding floral meristem identity gene products. The invention provides a substantially purified nucleic acid molecule encoding *Brassica oleracea* AP1 having the amino acid sequence SEQ ID NO: 4; a substantially purified nucleic acid molecule encoding *Brassica oleracea* var. *botrytis* AP1 having the amino acid sequence SEQ ID NO: 6; or a substantially purified nucleic acid molecule encoding *Zea mays* AP1 having the amino acid sequence SEQ ID NO: 8. In addition, the invention provides a substantially purified nucleic acid molecule that encodes a *Brassica oleracea* AP1, *Brassica oleracea* var. *botrytis* AP1 or *Zea mays* AP1 and that contains additional 5' or 3' noncoding sequence. For example, a substantially purified nucleic acid molecule having a nucleotide sequence such as SEQ ID NO: 3, SEQ ID NO: 5 or SEQ ID NO: 7 is provided.

As used herein in reference to a particular nucleic acid molecule or gene product, the term "substantially purified" means that the particular nucleic acid molecule or gene product is in a form that is relatively free from contaminating lipids, unrelated gene products, unrelated nucleic acids or other cellular material normally associated with the particular nucleic acid molecule or gene product in a cell.

The present invention also provides a nucleotide sequence having at least ten contiguous nucleotides of a nucleic acid molecule encoding *Brassica oleracea* AP1, *Brassica oleracea* var. *botrytis* AP1 or *Zea mays* AP1, provided that said nucleotide sequence is not present in a nucleic acid molecule encoding a MADS domain containing protein. In particular, such a nucleotide sequence can have at least ten contiguous nucleotides of a nucleic acid molecule encoding an AP1 gene product having the amino acid sequence of SEQ ID NO: 4, SEQ ID NO: 6 or SEQ ID NO: 8. A nucleotide sequence of the invention can have, for example, at least ten contiguous nucleotides of the nucleic acid sequence of SEQ ID NO: 3, SEQ ID NO: 5 or SEQ ID NO: 7.

As used herein, the term "contiguous," as used in reference to the nucleotides of a nucleic acid molecule means that the nucleotides of the nucleic acid molecule follow continuously in sequence. Thus, a nucleotide sequence of the invention has at least ten contiguous nucleotides of one of the recited nucleic acid molecules without any extraneous intervening nucleotides.

Explicitly excluded from a nucleotide sequence of the present invention is a nucleotide sequence having at least ten contiguous nucleotides that is present in a nucleic acid molecule encoding a MADS domain containing protein. MADS domain containing proteins are well known in the art as described in Purugganan et al., supra, 1995.

In general, a nucleotide sequence of the invention can range in size from about 10 nucleotides to the full-length of a cDNA. Such a nucleotide sequence can be chemically synthesized, using routine methods or can be purchased from a commercial source. In addition, such a nucleotide sequence can be obtained by enzymatic methods such as random priming methods, polymerase chain reaction (PCR) methods or by standard restriction endonuclease digestion, followed by denaturation (Sambrook et al., supra, 1989).

A nucleotide sequence of the invention can be useful, for example, as a primer for PCR (Innis et al. (ed.) *PCR Protocols: A Guide to Methods and Applications*, San Diego, Calif.: Academic Press, Inc. (1990)). Such a nucleotide sequence generally contains from about 10 to about 50 nucleotides.

A nucleotide sequence of the invention also can be useful in screening a cDNA or genomic library to obtain a related nucleotide sequence. For example, a cDNA library that is prepared from rice or wheat can be screened with a nucleotide sequence having at least ten contiguous nucleotides of the nucleic acid molecule encoding *Zea mays* AP1 (SEQ ID NO: 7) in order to isolate a rice or wheat ortholog of AP1. Generally, a nucleotide sequence useful for screening a cDNA or genomic library contains at least about 14 to 16 contiguous nucleotides depending, for example, on the hybridization conditions to be used. A nucleotide sequence containing at least 18 to 20 nucleotides, or containing at least 21 to 25 nucleotides, also can be useful.

A nucleotide sequence having at least ten contiguous nucleotides of a nucleic acid molecule encoding *Zea mays* AP1 (SEQ ID NO: 7) also can be used to screen a *Zea mays* cDNA library to isolate a sequence that is related to but distinct from AP1. Similarly, a nucleotide sequence having at least ten contiguous nucleotides of a nucleic acid molecule encoding *Brassica oleracea* AP1 (SEQ ID NO: 3) or a nucleotide sequence having at least ten contiguous nucleotides of a nucleic acid molecule encoding *Brassica oleracea* var. *botrytis* AP1 (SEQ ID NO: 5) can be used to screen a *Brassica oleracea* or *Brassica oleracea* var. *botrytis* cDNA library to isolate a novel sequence that is related to but distinct from AP1. In addition, a nucleotide sequence of the invention can be useful in analyzing RNA levels or patterns of expression, as by northern blotting or by in situ hybridization to a tissue section. Such a nucleotide sequence also can be used in Southern blot analysis to evaluate gene structure and identify the presence of related gene sequences.

The invention also provides a vector containing a nucleic acid molecule encoding a *Brassica oleracea* AP1 gene product, *Brassica oleracea* var. *botrytis* AP1 gene product or *Zea mays* AP1 gene product. A vector can be a cloning vector or an expression vector and provides a means to transfer an exogenous nucleic acid molecule into a host cell, which can be a prokaryotic or eukaryotic cell. Such vectors are well known and include plasmids, phage vectors and viral vectors. Various vectors and methods for introducing such vectors into a cell are described, for example, by Sambrook et al., supra, 1989, and by Glick and Thompson, supra, 1993).

The invention further provides a method of producing an AP1 gene product by expressing a nucleic acid molecule encoding an AP1 gene product. Thus, a *Brassica oleracea* AP1 gene product can be produced according to a method of the invention by expressing a nucleic acid molecule having the amino acid sequence of SEQ ID NO: 4 or by expressing a nucleic acid molecule having the nucleic acid sequence of SEQ ID NO: 3. Similarly, a *Brassica oleracea* var. *botrytis* AP1 gene product can be produced according to a method of the invention by expressing a nucleic acid molecule having the amino acid sequence of SEQ ID NO: 6 or by expressing a nucleic acid molecule having the nucleic acid sequence of SEQ ID NO: 5. A *Zea mays* AP1 gene product can be produced by expressing a nucleic acid molecule having the amino acid sequence of SEQ ID NO: 8 or by expressing a nucleic acid molecule having the nucleic acid sequence of SEQ ID NO: 7.

The invention also provides a substantially purified AP1 gene product, such as a substantially purified *Brassica oleracea* AP1 gene product having amino acid sequence SEQ ID NO: 4; a substantially purified *Brassica oleracea* var. *botrytis* AP1 gene product having amino acid sequence SEQ ID NO: 6; or a substantially purified *Zea mays* AP1 gene product having amino acid sequence SEQ ID NO: 8. As used herein, the term "gene product" is used in its broadest sense and includes proteins, polypeptides and peptides, which are related in that each consists of a sequence of amino acids joined by peptide bonds. For convenience, the terms "gene product," "protein" and "polypeptide" are used interchangeably. While no specific attempt is made to distinguish the size limitations of a protein and a peptide, one skilled in the art would understand that proteins generally consist of at least about 50 to 100 amino acids and that peptides generally consist of at least two amino acids up to a few dozen amino acids. The term gene product as used herein includes any such amino acid sequence.

An active fragment of a floral meristem identity gene product also can be useful in the methods of the invention. As used herein, the term "active fragment," means a polypeptide portion of a floral meristem identity gene product that can convert shoot meristem to floral meristem in an angiosperm. An active fragment of an AP1 gene product can consist, for example, of an amino acid sequence that is derived from SEQ ID NO: 2, SEQ ID NO: 4, SEQ ID NO: 6 or SEQ ID NO: 8 and has activity in converting shoot meristem to floral meristem in an angiosperm. An active fragment can be, for example, an amino terminal, carboxyl terminal or internal fragment of *Zea mays* AP1 (SEQ ID NO: 8) that has activity in converting shoot meristem to floral meristem in an angiosperm. The skilled artisan will recognize that an active fragment of a floral meristem identity gene product, as defined herein, can be useful in the methods of the invention for converting shoot meristem to floral meristem in an angiosperm, for producing early reproductive development in a seed plant, or for producing reproductive sterility in a seed plant.

Such an active fragment can be produced using well known recombinant DNA methods (Sambrook et al., supra, 1989). Similarly, an active fragment can be, for example, an amino terminal, carboxyl terminal or internal fragment of *Arabidopsis thaliana* CAL (SEQ ID NO: 10) or *Brassica oleracea* CAL (SEQ ID NO: 12) that has activity, for example, in converting shoot meristem to floral meristem in an angiosperm. The product of the BobCAL gene (SEQ ID NO: 24), which is truncated at amino acid 150, lacks activity in converting shoot meristem to floral meristem and, therefore, is an example of a polypeptide portion of a CAL floral meristem identity gene product that is not an "active fragment" of a floral meristem identity gene product.

An active fragment of a floral meristem identity gene product, which can convert shoot meristem to floral meristem in an angiosperm, can be identified using the methods described in Examples I, II and III. Briefly, an angiosperm such as Arabidopsis can be transformed with a nucleic acid molecule encoding a portion of a floral meristem identity gene product in order to determine whether the portion can convert shoot meristem to floral meristem and, therefore, is an active fragment of a floral meristem identity gene product.

The invention further provides an antibody that specifically binds an AP1 gene product having the amino acid sequence of *Brassica oleracea* AP1 (SEQ ID NO: 4); the amino acid sequence of *Brassica oleracea* var. *botrytis* AP1 (SEQ ID NO: 6); or the amino acid sequence of *Zea mays* AP1 (SEQ ID NO: 8). As used herein, the term "antibody" is used in its broadest sense to include naturally occurring and non-naturally occurring polyclonal and monoclonal antibodies, as well as a polypeptide fragment of an antibody that retains a specific binding activity of at least about $1 \times 10^5$ $M^{-1}$, and preferably about $1 \times 10^6$ $M^{-1}$, for an AP1 gene product having amino acid sequence SEQ ID NO: 4, SEQ ID NO: 6 or SEQ ID NO: 8. One skilled in the art would know that an antibody fragment such as a Fab, $F(ab')_2$ or Fv fragment can retain specific binding activity for an AP1 gene product and, thus, is included within the definition of an antibody. A non-naturally occurring antibody, or fragment thereof, such as a chimeric antibody or humanized antibody also is included within the meaning of the term antibody. Such a non-naturally occurring antibody can be constructed using solid phase peptide synthesis, produced recombinantly or obtained, for example, by screening a combinatorial library consisting of variable heavy chains and variable light chains as described by Huse et al., *Science* 246:1275–1281 (1989), which is incorporated herein by reference.

An antibody "specific for" a gene product, or that "specifically binds" a gene product, binds with substantially higher affinity to that gene product than to an unrelated gene product. An antibody specific for a gene product also can have specificity for a related gene product. For example, an antibody specific for a *Zea mays* AP1 gene product also can specifically bind an *Arabidopsis thaliana* AP1 gene product or a *Brassica oleracea* AP1 gene product.

An antibody that specifically binds a *Zea mays* AP1 gene product (SEQ ID NO: 8), for example, can be prepared using a *Zea mays* AP1 fusion protein or a synthetic peptide encoding a portion of *Zea mays* AP1 (SEQ ID NO: 8) as an immunogen. One skilled in the art would know that purified *Zea mays* AP1 gene product, which can be prepared from a natural source or produced recombinantly according to a method of the invention, or a fragment of a *Zea mays* AP1 gene product, including a peptide portion of *Zea mays* AP1 such as a synthetic peptide, can be used as an immunogen. For example, preparation of antisera that specifically binds an AP1 gene product is described in Example VI using a GST-AP1 fusion protein containing amino acids 190 to 251 of AP1 as an immunogen. In addition, a non-immunogenic fragment or synthetic peptide derived from *Zea mays* AP1, for example, can be made immunogenic by coupling the non-immunogenic fragment or peptide (hapten) to a carrier molecule such as bovine serum albumin (BSA) or keyhole limpet hemocyanin (KLH). In addition, various other carrier molecules and methods for coupling a hapten to a carrier molecule are well known in the art as described, for example, by Harlow and Lane, *Antibodies: A Laboratory Manual* (Cold Spring Harbor Laboratory Press, 1988), which is incorporated herein by reference.

The invention also provides an expression vector containing a nucleic acid molecule encoding a floral meristem identity gene product such as AP1, CAL or LFY operably linked to a heterologous regulatory element. Expression vectors are well known in the art and provide a means to transfer and express an exogenous nucleic acid molecule into a host cell. Thus, an expression vector contains, for example, transcription start and stop sites such as a TATA sequence and a poly-A signal sequence, as well as a translation start site such as a ribosome binding site and a stop codon, if not present in the coding sequence.

As used herein, the term "heterologous regulatory element" means a regulatory element derived from a different gene than the gene encoding the floral meristem identity gene product to which it is operably linked. A vector containing a floral meristem identity gene, however, contains a nucleic acid molecule encoding a floral meristem identity gene product operably linked to a homolgous regulatory element. Such a vector does not contain a nucleic acid molecule encoding a floral meristem identity gene product operably linked to a heterologous regulatory element and, thus, is not an expression vector of the invention.

The invention further provides a plant expression vector containing a floral meristem identity gene product operably linked to a heterologous regulatory element. For example, a plant expression vector containing a nucleic acid molecule encoding an AP1 gene product having at least about 70 percent amino acid identity with an amino acid sequence of *Arabidopsis thaliana* AP1 (SEQ ID NO: 2) in the region from amino acid 1 to amino acid 163 or with the amino acid sequence of *Zea mays* AP1 (SEQ ID NO: 8) in the region from amino acid 1 to amino acid 163 is provided. A plant expression vector containing a floral meristem identity gene product operably linked to a constitutive regulatory element, such as the cauliflower mosaic virus 35S promoter, is provided. In addition, a plant expression vector containing a floral meristem identity gene product operably linked to an inducible regulatory element is provided.

A useful plant expression vector can contain a constitutive regulatory element for expression of an exogenous nucleic acid molecule in all or most tissues of a seed plant. The use of a constitutive regulatory element can be particularly advantageous because expression from the element is relatively independent of developmentally regulated or tissue-specific factors. For example, the cauliflower mosaic virus 35S promoter (CaMV 35S) is a well-characterized constitutive regulatory element that produces a high level of expression in all plant tissues (Odell et al., *Nature* 313:810–812 (1985), which is incorporated herein by reference). Furthermore, the CaMV 35S promoter can be particularly useful due to its activity in numerous different seed plant species (Benfey and Chua, *Science* 250:959–966 (1990), which is incorporated herein by reference; Odell et al., supra, 1985). Other constitutive regulatory elements useful for expression in a seed plant include, for example, the cauliflower mosaic virus 19S promoter; the Figwort mosaic virus promoter (Singer et al., *Plant Mol. Biol.* 14:433 (1990), which is incorporated herein by reference); and the nopaline synthase (nos) gene promoter (An, *Plant Physiol.* 81:86 (1986), which is incorporated herein by reference).

In addition, an expression vector of the invention can contain a regulated gene regulatory element such as a promoter or enhancer element. A particularly useful regulated promoter is a tissue-specific promoter such as the shoot meristem-specific CDC2 promoter (Hemerly et al., *Plant Cell* 5:1711–1723 (1993), which is incorporated herein by reference), or the AGL8 promoter, which is active in the apical shoot meristem immediately after the transition to flowering (Mandel and Yanofsky, supra, 1995). The promoter of the SHOOTMERISTEMLESS gene, which is expressed exclusively in the shoot meristem beginning within an embryo and throughout the angiosperm life cycle, also can be a particularly useful tissue-specific gene regulatory element (see Long et al., *Nature* 379:66–69 (1996), which is incorporated herein by reference).

An appropriate regulatory element such as a promoter is selected depending on the desired pattern or level of expression of a nucleic acid molecule linked thereto. For example, a constitutive promoter, which is active in all tissues, would be appropriate if expression of a gene product in all plant tissues is desired. In addition, a developmentally regulated or tissue-specific regulatory element can be useful to direct floral meristem identity gene expression to specific tissues, for example. As discussed above, inducible expression also can be particularly useful to manipulate the timing of gene expression such that, for example, a population of transgenic seed plants of the invention that contain an expression vector comprising a floral meristem identity gene linked to an inducible regulatory element can undergo early reproductive development at essentially the same time. Selecting the time of reproductive development can be useful, for example, in manipulating the time of crop harvest.

Using nucleic acid molecules encoding AP1 provided herein, the skilled artisan can isolate, if desired, a novel ortholog of AP1. For example, one would choose a region of AP1 that is highly conserved among known AP1 sequences such as a region that is highly conserved between Arabidopsis AP1 (SEQ ID NO: 1) and *Zea mays* AP1 (GenBank accession number L46400; SEQ ID NO: 7) to screen a cDNA or genomic library of interest for a novel AP1 ortholog. One can use a full-length Arabidopsis AP1 (SEQ ID NO: 1), for example, to isolate a novel ortholog of AP1 (see Example V). If desired, the region encoding the MADS domain, which is common to a number of genes, can be excluded, from the sequence used as a probe. Similarly, the skilled artisan knows that a nucleic acid molecule encoding a full-length CAL cDNA such as Arabidopsis CAL (SEQ ID NO: 9) or *Brassica oleracea* CAL (SEQ ID NO: 11) can be useful in isolating a novel CAL ortholog.

For example, the Arabidopsis AP1 cDNA (SEQ ID NO: 1) can be used as a probe to identify and isolate a novel AP1 ortholog. Using a nucleotide sequence derived from a conserved region of SEQ ID NO: 1, SEQ ID NO: 3, SEQ ID NO: 5 or SEQ ID NO: 7, for example, a nucleic acid molecule encoding a novel AP1 ortholog can be isolated from other plant species. Using methods such as those described by Purugganan et al., supra, 1995, one can readily confirm that the newly isolated molecule is an AP1 ortholog. Thus, a nucleic acid molecule encoding an AP1 gene product, which has at least about 70 percent amino acid identity with the amino acid sequence of SEQ ID NO: 2 (Arabidopsis AP1) in the region from amino acid 1 to amino acid 163 or with the amino acid sequence of SEQ ID NO: 8 (*Zea mays* AP1) in the region from amino acid 1 to amino acid 163 can be isolated and identified using well known methods.

Similarly, in order to isolate an ortholog of CAL, one can choose a region of CAL that is highly conserved among known CAL cDNAs, such as a region conserved between Arabidopsis CAL (SEQ ID NO: 9) and *Brassica oleracea* CAL (SEQ ID NO: 11). The Arabidopsis CAL cDNA (SEQ ID NO: 9) or *Brassica oleracea* CAL cDNA (SEQ ID NO: 11), or a nucleotide fragment thereof, can be used to identify and isolate a novel CAL ortholog using methods such as those described in Example V. In order to identify related MADS domain genes, a nucleotide sequence derived from the MADS domain of AP1 or CAL, for example, can be useful to isolate a related gene sequence encoding this DNA-binding motif.

Hybridization conditions for isolating a gene ortholog, for example, are relatively stringent such that non-specific hybridization is minimized. Appropriate hybridization conditions can be determined empirically, or can be estimated based, for example, on the relative G+C content of the probe and the number of mismatches between the probe and target sequence, if known. Hybridization conditions can be adjusted as desired by varying, for example, the temperature of hybridizing or the salt concentration (Sambrook, supra, 1989).

The invention also provides a kit for converting shoot meristem to floral meristem in an angiosperm, which contains a plant expression vector having a nucleic acid molecule encoding a floral meristem identity gene product. A kit for promoting early reproductive development in a seed plant, which contains a plant expression vector having a nucleic acid molecule encoding a floral meristem identity gene product, also is provided. If desired, such kits can contain appropriate reagents to facilitate high efficiency transformation of a seed plant with a plant expression vector of the invention. Furthermore, if desired, a control vector lacking a floral meristem identity gene can be included in the kits to determine, for example, the efficiency of transformation.

The following examples are intended to illustrate but not limit the present invention.

EXAMPLE I

Conversion of Shoot Meristem to Floral Meristem and Early Reproductive Development in an APETALA1 Transgenic Plant This example describes methods for producing a transgenic Arabidopsis plant containing ectopically expressed AP1.

A. Ectopic Expression of APETALA1 Converts Inflorescence Shoots into Flowers

Transgenic plants that constitutively express AP1 from the cauliflower mosaic virus 35S (CaMV 35S) promoter were produced to determine whether ectopic AP1 expression was sufficient to convert shoot meristem to floral meristem. The AP1 coding sequence was placed under control of the CaMV 35S promoter (Odell et al., supra, 1985) as follows. Bam HI linkers were ligated to the Hinc II site of the full-length AP1 complementary DNA (Mandel et al., supra, (1992), which is incorporated herein by reference) in pAM116, and the resulting Bam HI fragment was fused to the CaMV 35S promoter (Jack et al., *Cell* 76:703–716 (1994), which is incorporated herein by reference) in pCGN18 to create pAM563.

Transgenic 35S-AP1 Arabidopsis plants of the Columbia ecotype were generated by selecting kanamycin-resistant plants after Agrobacterium-mediated plant transformation using the in planta method (Bechtold et al., *C. R. Acad. Sci. Paris* 316:1194–1199 (1993), which is incorporated herein by reference). All analyses were performed in subsequent generations. Approximately 120 independent transgenic lines that displayed the described phenotypes were obtained.

Remarkably, in 35S-AP1 transgenic plants, the normally indeterminate shoot apex prematurely terminated as a floral meristem and formed a terminal flower. Generally, lateral meristems that normally would produce inflorescence shoots also were converted into solitary flowers. These results demonstrate that ectopic expression of AP1 in shoot meristem is sufficient to convert shoot meristem to floral meristem, even though AP1 normally is not absolutely required to specify floral meristem identity.

B. LEAFY is not Required for the Conversion of Inflorescence Shoots to Flowers in an APETALA1 Transgenic Plant To determine whether the 35S-AP1 transgene causes ectopic LFY activity, and whether ectopic LFY activity is required for the conversion of shoot meristem to floral meristem, the 35S-AP1 transgene was introduced into Arabidopsis lfy mutants. The 35S-AP1 transgene was crossed into the strong lfy-6 mutant background and the $F_2$ progeny were analyzed.

Mutant lfy plants containing the 35S-AP1 transgene displayed the same conversion of apical and lateral shoot meristem to floral meristem as was observed in transgenics containing wild type LFY. However, the resulting flowers had the typical lfy mutant phenotype, in which floral organs developed as sepaloid and carpelloid structures, with an absence of petals and stamens. These results demonstrate that LFY is not required for the conversion of shoot meristem to floral meristem in a transgenic angiosperm that ectopically expresses AP1.

C. APETALA1 is not Sufficient to Specify Organ Fate

As well as being involved in the early step of specifying floral meristem identity, AP1 also is involved in specifying sepal and petal identity at a later stage in flower development. Although AP1 RNA initially is expressed throughout the young flower primordium, it is later excluded from stamen and carpel primordia (Mandel et al., supra, 1992). Since the CaMV 35S promoter is active in all floral organs, 35S-AP1 transgenic plants are likely to ectopically express AP1 in stamens and carpels. However, the normal stamens and carpels 35S-AP1 in transgenic plants indicate that AP1 is not sufficient to specify sepal and petal organ fate.

D. Ectopic Expression of APETALA1 Causes Early Reproductive Development

In addition to its ability to alter inflorescence meristem identity, ectopic expression of AP1 also influences the vegetative phase of plant growth. Wild-type Arabidopsis plants have a vegetative phase during which a basal rosette of leaves is produced, followed by the transition to reproductive growth. The transition from vegetative to reproductive growth was measured both in terms of the number of days post-germination until the first visible flowers were observed, and by counting the number of leaves. Under continuous light, wild-type and 35S-AP1 transgenic plants flowered after producing 9.88±1.45 and 4.16±0.97 leaves, respectively. Under short-day growth conditions (8 hours light, 16 hours dark, 24 C), wild-type and 35S-AP1 transgenic plants flowered after producing 52.42±3.47 and 7.4±1.18 leaves, respectively.

Under continuous light growth conditions, flowers appear on wild-type Arabidopsis plants after approximately 18 days, whereas the 35S-AP1 transgenic plants flowered after an average of only 10 days. Furthermore, under short-day growth conditions, flowering is delayed in wild-type Arabidopsis plants until approximately 10 weeks after germination, whereas 35S-AP1 transgenic plants flowered in less than about five weeks. Thus, ectopic AP1 expression significantly reduced the time of reproductive development, as indicated by the time of flowering. Ecotopic AP1 expression also reduced the delay of flowering caused by short day growth conditions.

EXAMPLE II

Conversion of Inflorescence Shoots into Flowers in an CAULIFLOWER Transgenic Plant This example describes methods for producing a transgenic Arabidopsis plant that ectopically expresses CAL.

Transgenic Arabidopsis plants that ectopically express CAL in shoot meristem were generated. The full-length CAL cDNA was inserted downstream of the CaMV 35S promoter in the Eco RI site of pMON530 (Monsanto Co., St. Louis, Mo.) This plasmid was introduced into Agrobacterium strain ASE and used to transform the Columbia ecotype of Arabidopsis using the modified vacuum infiltration method described by Bechtold et al., supra, 1993. The 96 transgenic lines that harbored the 35S-CAL construct had a range of weak to strong phenotypes. Transgenic plants with the strongest phenotypes (27 lines) had a phenotype that closely resembled the tf1 mutant phenotype.

The apical and lateral inflorescence shoots of 35S-CAL transgenic plants were converted into flowers. Furthermore, the 35S-CAL transgenic plants were characterized by early reproductive development, as indicated by an early flowering phenotype. These results demonstrate that ectopic expression of CAL is sufficient for the conversion of shoots to flowers and for promoting early reproductive development.

EXAMPLE III

Conversion of Shoots into Flowers and Early Reproductive Developemnt in a LEAFY Transgenic Plant This example describes methods for producing transgenic Arabidopsis ectopically expressing LFY and transgenic aspen ectopically expressing LFY.

A. Conversion of Arabidopsis Shoots and Early Arabidopsis Reproductive Development by LEAFY Transgenic Arabidopsis plants were generated by transforming Arabidopsis with LFY under the control of the CaMV 35S promoter (Odell et al., supra, (1985)). A LFY complementary DNA (Weigel et al, Cell 69:843–859 (1992), which is incorporated herein by reference) was inserted into a T-DNA transformation vector containing a CaMV 35S promoter and a 3' nos cassette (Jack et al., supra, 1994). Transformed seedlings were selected for kanamycin resistance. Several hundred Arabidopsis transformants in three different genetic backgrounds (Nossen, Wassilewskija and Columbia) were recovered, and several lines were characterized in detail.

High levels of LFY RNA expression were detected by northern blot analysis in 35S-LFY transgenics. In general, Nossen lines had weaker phenotypes, especially when grown under short day conditions. The 35S-LFY transgene of line DW151.117 (ecotype Wassilewskija) was introgressed into the erecta background by backcrossing to a Landsberg erecta strain. Plants were grown under 16 hours light and 8 hours dark. The 35S-LFY transgene provided at least as much LFY activity as the endogenous gene and completely suppressed the lfy mutant phenotype when crossed into the background of the lfy-6 null allele.

Most 35S-LFY transgenic plants lines demonstrated a very similar, dominant and heritable phenotype. Secondary shoots that arose in lateral positions were consistently replaced by solitary flowers, and higher-order shoots were absent. Although the number of rosette leaves was unchanged from the wild type, 35S-LFY plants flowered earlier than wild type: the solitary flowers in the axils of the rosette leaves developed and opened precociously. In addition, the primary shoot terminated with a flower. In 35S-LFY transgenics having the most extreme phenotypes, a terminal flower was formed immediately above the rosette. This gain of function phenotype (conversion of shoots to flowers) is the opposite of the lfy loss of function phenotype (conversion of flowers to shoots). These results demonstrate that LFY encodes a developmental switch that is both sufficient and necessary to convert shoot meristem to flower meristem in an angiosperm.

The effects of constitutive LFY expression differ for primary and secondary shoot meristems. Secondary meristems were transformed into flower meristem, apparently as soon as it developed, and produced only a single, solitary flower. In contrast, primary shoot meristem produced leaves and lateral flowers before being consumed in the formation of a terminal flower. These developmental differences indicate that a meristem must acquire competence to respond to the activity of a floral meristem identity gene such as LFY.

B. Conversion of Aspen Shoots by LEAFY

Given that constitutive expression of LFY induced early reproductive development as indicated by precocious flowering during the vegetative phase of Arabidopsis, the effect of LFY on the flowering of other seed plant species was examined. The perennial tree, hybrid aspen, is derived from parental species that flower naturally only after 8–20 years of growth (Schopmeyer (ed.), *USDA Agriculture Handbook 450: Seeds of Woody Plants in the United States,* Washington D.C., USA: US Government Printing Office, pp. 645–655 (1974)). 35S-LFY transgenic aspen plants were obtained by Agrobacterium-mediated transformation of stem segments and subsequent regeneration of transgenic shoots in tissue culture.

Hybrid aspen was transformed exactly as described by Nilsson et al. (Transgen. Res. 1:209–220 (1992), which is incorporated herein by reference). Levels of LFY RNA expression were similar to those of 35S-LFY Arabidopsis, as determined by northern blot analysis. The number of vegetative leaves varied between different regenerating shoots, and those with a higher number of vegetative leaves formed roots, allowing for transfer to the greenhouse. Individual flowers were removed either from primary transformants that had been transferred to the greenhouse, or from catkins collected in spring, 1995, at Carlshem, Umea, Sweden) from a tree whose age was determined by counting the number of annual rings in a core extracted with an increment borer at 1.5 meters above ground level. Flowers were fixed in formaldehyde/acetic acid/ethanol and destained in ethanol before photography.

The overall phenotype of 35S-LFY transgenic aspen was similar to that of 35S-LFY Arabidopsis. In wild-type plants of both species, flowers normally are formed in lateral positions on inflorescence shoots. In aspen, these inflorescence shoots, called catkins, arise from the leaf axils of adult trees. In both 35S-LFY Arabidopsis and 35S-LFY aspen, solitary flowers were formed instead of shoots in the axils of vegetative leaves. Moreover, as in Arabidopsis, the secondary shoots of transgenic aspen were more severely affected than the primary shoot.

Regenerating 35S-LFY aspen shoots initially produced solitary flowers in the axils of normal leaves. However, the number of vegetative leaves was limited, and the shoot meristem was prematurely consumed in the formation of an aberrant terminal flower. Early reproductive development as demonstrated by precocious flowering was specific to 35S-LFY transformants and was not observed in non-transgenic controls. Furthermore, not a single instance of precocious flower development has been observed in more than 1,500 other lines of transgenic aspen generated with various constructs from 1989 to 1995 at the Swedish University of Agricultural Sciences. These results demonstrate that a floral meristem identity gene product can promote early reproductive development in a heterologous angiosperm species.

EXAMPLE IV

Dexamethasone-Inducible Floral Meristem Identity Gene Activity in Transgenic Plants This example describes the construction and characterization of an AP1-glucocorticoid receptor ligand binding domain chimera and its dexamethasone-inducible activity in Arabidopsis.

A. Construction and Characterization of an AP1-Glucocorticoid Receptor Ligand Binding Domain Chimera A nucleic acid molecule encoding an AP1-glucocorticoid receptor ligand binding domain chimera was prepared as follows. Primers corresponding to the translation initiation and termination codons of AP1 were synthesized for PCR amplification of the Arabidopsis AP1 cDNA. Primer 5'-GGATCCGGATCAAAAATGGGAAGGGGTAG-3' (SEQ ID NO: 25) contains a translation initiation codon, which is indicated by underlining. Primer 5'-GGATC CGCTGCGGCGAAGCAGCCAAGGTTG-3' (SEQ ID NO: 26) contains a modified translation termination site, which is indicated by underlining and allows the nucleic acid molecule encoding AP1 to be linked in frame to the nucleic acid molecule encoding the glucocorticoid receptor (GR) ligand binding domain.

The full length Arabidopsis AP1 cDNA in pAM116 (see Example I) was used as the template for PCR amplification with primers SEQ ID NOS: 25 and 26, each of which contain a Bam H1 site. The resulting Bam HI fragment, which encodes the full-length Arabidopsis AP1 cDNA except for the translation termination codon, was cloned into the unique Bam HI site of the GR fusion vector constructed by Lloyd et al., supra, 1994. DNA sequence analyses confirmed that the construct contained the predicted nucleotide sequence.

The resulting AP1-GR construct was introduced into Agrobacterium strain ASE, and ap1-15 mutant plants were transformed using the vacuum infiltration method described in Example I. Approximately 100 independently derived lines were selected in kanamycin for further analysis.

B. Dexamethasone-Inducible Activity of an AP1-Glucocorticoid Receptor Ligand Binding Domain Chimera in Arabidopsis Kanamycin-resistant transgenic Arabidopsis lines are analyzed in subsequent generations for AP1 activity. After application of dexamethasone to transgenic plants, AP1 activity is monitored by visual inspection for 1) flowering that is earlier than wild-type or 2) partial or complete rescue of the ap1 mutant phenotype.

To assay for dexamethasone-inducible activity, plants are watered with varying concentrations of dexamethasone. A range of dexamethasone concentrations are tested to determine overall levels of AP1 activity and to determine the resulting phenotypes. A concentration of 1 $\mu$M or less dexamethasone preferably is used for induction of AP1 activity.

In addition, dexamethasone is applied directly to plants by spraying. Spraying, like watering, leads to a significant induction of AP1 activity, resulting in the corresponding rescue of the ap1 mutant phenotype and early reproductive development. Although a single application of dexamethasone is sufficient to increase AP1 activity and promote early reproductive development, dexamethasone is applied either once, or repeatedly, and the treatments compared for any observed differences under long or short day conditions as disclosed below.

Dexamethasone is applied to plants at various times post-germination. For example, a large number of AP1-GR transgenic Arabidopsis plants are grown, some of which are treated with dexamethasone on day 1 post-germination, some on day 2, etc., all the way up until and beyond the time at which Arabidopsis plants normally flower. These analyses include plants grown under long day, short day, and under a variety of temperatures. For example, Arabidopsis plants, which typically are grown at 25° C., also can be analyzed for AP1 activity at 20° C. and 15° C. (see, for example, Bowman et al. (ed.), *Arabidopsis: An Atlas of Morphology and Development,* New York: Springer (1994), which is incorporated by reference herein).

EXAMPLE V

Identification and Characterization of the *Zea Mays* APETALA1 cDNA

This example describes the isolation and characterization of *Zea mays* ZAP1 complementary DNA, which is an ortholog of the Arabidopsis floral meristem identity gene AP1.

A. Identification and Characterization of a Nucleic Acid Sequence Encoding ZAP1

The utility of using a cloned floral homeotic gene from Arabidopsis to identify the putative ortholog in maize has been demonstrated previously (Schmidt et al., supra, (1993), which is incorporated herein by reference). As described in Mena et al. (*Plant J.* 8(6):845–854 (1995)), the maize ortholog of the Arabidopsis AP1 floral meristem identity gene, was isolated by screening a *Zea mays* ear cDNA library using the Arabidopsis AP1 cDNA (SEQ ID NO: 1) as a probe. A cDNA library was prepared from wild-type immature ears as described by Schmidt et al., supra, 1993, and screened using the Arabidopsis AP1 cDNA SEQ ID NO: 1 as the probe. Low-stringency hybridizations with the AP1 probe were conducted as described previously for the isolation of ZAG1 using the AG cDNA as a probe (Schmidt et al., supra, 1993). Positive plaques were isolated and cDNAs were recovered in Bluescript by in vivo excision. Double-stranded sequencing was performed using the Sequenase Version 2.0 kit (U.S. Biochemical, Cleveland, Ohio) according to the manufacturer's protocol.

The nucleotide sequence and deduced amino acid sequence of the ZAP1 cDNA are provided as SEQ ID NOS: 7 and 8. The deduced amino acid sequence for ZAP1 shares 89% identity with Arabidopsis AP1 through the MADS domain (amino acids 1 to 57) and 70% identity through the first 160 amino acids, which includes the K domain. The high level of amino acid sequence identity between ZAP1 and AP1 (SEQ ID NOS: 8 and 2), as well as the expression pattern of ZAP1 in maize florets (see below), indicate that ZAP1 is the maize ortholog of Arabidopsis AP1.

B. RNA Expression Pattern of ZAP1

Total RNA was isolated from different maize tissues as described by Cone et al., *Proc. Natl. Acad. Sci., USA* 83:9631–9635 (1986), which is incorporated herein by reference. RNA was prepared from ears or tassels at early developing stages (approximately 2 cm in size), husk leaves from developing ear shoots, shoots and roots of germinated seedlings, leaves from 2 to 3 week old plants and endosperm, and embryos at 18 days after pollination. Mature floral organs were dissected from ears at the time of silk emergence or from tassels at several days pre-emergence. To study expression patterns in the mature female flower, carpels were isolated and the remaining sterile organs were pooled and analyzed together. In the same way, stamens were dissected and collected from male florets and the remaining organs (excluding the glumes) were pooled as one sample.

RNA concentration and purity was determined by absorbance at 260/280 nM, and equal amounts (10 $\mu$g) were fractionated on formaldehyde-agarose gels. Gels were stained in a solution of 0.125 $\mu$g ml$^{-1}$ acridine orange to confirm the integrity of the RNA samples and the uniformity of gel loading, then RNA was blotted on to Hybond-N® membranes (Amersham International, Arlington Heights, Ill.) according to the manufacturer's instructions. Prehybridization and hybridization solutions were prepared as previously described (Schmidt et al., *Science* 238:960–963 (1987), which is incorporated herein by reference). The probe for ZAP1 RNA expression studies was a 445 bp Sac I/Nsi I fragment from the 3' end of the cDNA. Southern blot analyses were conducted to establish conditions for specific hybridization of this probe. No cross-hybridization was detected using hybridization at 60° C. in 50% formamide and washes at 65° C. in 0.1×SSC and 0.5% SDS.

The strong sequence similarity between ZAP1 and AP1 indicated that ZAP1 was the ortholog of this Arabidopsis floral meristem identity gene. As a first approximation of whether the pattern of ZAP1 expression paralleled that of AP1, a blot of total RNA from vegetative and reproductive organs was hybridized with a gene-specific fragment of the ZAP1 cDNA (nucleotides 370 to 820 of SEQ ID NO: 7). ZAP1 RNA was detected only in male and female inflorescences and in the husk leaves that surround the developing ear. No ZAP1 RNA expression was detectable in RNA isolated from root, shoot, leaf, endosperm, or embryo tissue. The restriction of ZAP1 expression to terminal and axillary inflorescences is consistent with ZAP1 being the Arabidopsis AP1 ortholog.

Male and female florets were isolated from mature inflorescences, and the reproductive organs were separated from the remainder of the floret. RNA was isolated from the reproductive and the sterile portions of the florets. ZAP1 RNA expression was not detected in maize stamens or carpels, whereas high levels of ZAP1 RNA were present in developing ear and tassel florets from which stamens and carpels had been removed. Thus, the exclusion of ZAP1 expression from stamens and carpels and its inclusion in the RNA of the non-reproductive portions of the floret (lodicules, lemma and palea) is similar to the pattern of expression of AP1 in flowers of Arabidopsis.

EXAMPLE VI

Production and Characterization of Anti-AP1 Antisera

This example demonstrates the production and characterization of antisera that specifically binds the Arabidopsis AP1 gene product.

Western blotting was performed with plant tissue extracts and crude antisera from rabbits immunized with a GST-AP1 fusion protein encoding amino acids 190 to 251 of *Arabidopsis thaliana* AP1 (SEQ ID NO: 2). The C-terminal region of AP1 spanning amino acids 190 to 251 does not include the MADS domain, which is common to a number of proteins. As shown in FIG. 1, the anti-AP1 sera reacted with a 90 kDa protein in inflorescence tissue extracts prepared from wild type *Arabidopsis thaliana* (Landsburg ecotype). As expected, this reactivity was absent from Arabidopsis mutants lacking AP1 such as ap1-1 or ap1-15 (compare lanes 3 and 4 to lane 2).

AP1 expression was reduced significantly in inflorescence tissue extracts from the Arabidopsis ap2-2 mutant as compared to wild type plants, indicating that AP2 normally functions to increase or maintain the level of AP1 RNA or protein expression (see lanes 2 and 5). Similarly, reduced AP1 expression in lfy-6 mutant plants indicates that LFY normally functions to enhance expression of AP1 at the RNA or protein level (see lanes 2 and 6). In contrast to the results seen in ap2-2 or lfy-6 mutant inflorescences, AP1 protein expression in inflorescence tissue from ag-2 mutants is enhanced strikingly as compared to the level of AP1 protein seen in wild type inflorescences (see lanes 1 and 2). These results indicate that the AGAMOUS gene product (AG) negatively regulates AP1 RNA or protein expression.

Western analysis further demonstrated that AP1 protein expression is specific to inflorescence tissue since AP1 reactivity is absent from leaf tissue prepared from wild type Arabidopsis plants (Columbia ecotype; lane 7). In transgenic plants constitutively expressing AP1 from the CaMV promoter, however, AP1 protein expression readily was detectable in leaf tissue as shown in lane 8. Reactivity of the anti-AP1 antisera in 35S-AP1 transgenic leaves but not in wild type Arabidopsis leaves confirmed the specificity of the anti-AP1 sera.

Specificity of the anti-AP1 sera also was demonstrated by specific binding of the antisera to AP1 but not to the closely related CAL gene product. For example, inflorescence tissue extract from an ap1-1 or ap1-15 mutant plant (lane 3 or 4, respectively), which contains CAL but not AP1, was not reactive with the anti-AP1 rabbit sera. These data indicate that the anti-AP1 sera does not react with the CAL gene product.

For production of anti-AP1 sera, a Sty I fragment of the *Arabidopsis thaliana* AP1 cDNA, which encodes amino acids 190 to 251, was gel purified, blunt ended with Klenow fragment and ligated into the Sma I site of pGEX3X (Pharmacia, Piscataway, N.J.) to make pGEX-AP1$_{190-251}$ for expression of a GST-AP1$_{190-251}$ fusion protein. DH5α *E. coli* were transformed with the resulting vector by standard techniques (Sambrook, supra, 1989).

A bacterial culture of a pGEX-AP1$_{190-252}$ transformant was grown to an OD$_{600}$ of 0.5, and GST-AP1$_{190-251}$ expression was induced by addition of 1 mM IPTG. The GST-AP1$_{190-251}$ bacterial pellet was harvested after three hours growth at 37° C., washed once with phosphate-buffered saline (PBS; pH 7.2) and lysed by two cycles of freeze-thawing. The cell lysate was resuspended in one-fiftieth of the culture volume in ice cold EB (2 mM EDTA, 2 mM DTT, 1 mM PMSF, 5 µg/ml leupeptin, 7.5 µg/ml pepstatin, 1% aprotinin in PBS pH 7.2) with 2 mg/ml lysozyme and incubated on ice for 30 minutes. Triton X-100 was added to 1%, and the solution was sonicated mildly. The extract was clarified by two successive centrifugations of 1 and 15 minutes, respectively, at 13,000×g in a microfuge.

The GST-AP1$_{190-251}$ fusion protein was purified from the bacterial extract as follows. Glutathione-Sepharose beads (150 µl), which had been pre-equilibrated in EB with 1% Triton X-100, were added to 1 ml of soluble extract in an Eppendorf tube and incubated on a rotating wheel for 60 minutes at 4° C. The beads were washed five times in 1 ml EB with 1% Triton X-100; resuspended in protein sample buffer and loaded on a preparative SDS-PAGE gel (Laemmli, *Nature* 227:680–685 (1970), which is incorporated herein by reference). Following electrophoresis, the gel was stained for five minutes in 0.05% Coomassie R250 (Fisher Scientific, Pittsburgh, Pa.) in distilled water and subsequently destained in distilled water. GST-AP1$_{190-251}$ fusion protein was cut out of the gel and electroeluted in 0.5× transfer buffer for 3 hours at 100V as described in Harlow and Lane, supra, 1988. The GST-AP1$_{190-251}$ fusion protein was emulsified with Freund's adjuvant and injected into rabbits by Immunodynamics (La Jolla, Calif.).

Crude rabbit serum was used for western analysis at a dilution of 1 to 2000. Binding was detected using a secondary antibody coupled to peroxidase (Promega, Madison, Wis.; 1 to 2500 dilution) and revealed using an enhanced chemiluminesence kit (Amersham).

Plant protein extracts for western analysis were prepared by homogenizing 100 µl plant tissue with 200 µl 2×FSB (Laemmli, supra, 1970) in a Kontes microfuge tube with a pistil. The extract was denatured in boiling water bath for 5 minutes, sonicated for 1 minute and clarified by two successive spins of 5 and 15 minutes in a microfuge at 13'000×g prior to electophoresis.

EXAMPLE VII

Cosuppression of AP1 Activity

This example demonstrates the use of cosuppression to inhibit endogenous AP1 activity in Arabidopsis.

The full length AP1 cDNA from pAM116 (see Example I) was inserted into the Eco RI site of pMON530, and the resulting construct was introduced into Agrobacterium strain ASE. Wild type Arabidopsis was transformed as described in Example I and analyzed for ap1 mutant phenotypes. In this way, a large number of independently generated cosuppressed lines were generated. Each of the cosuppressed lines had a phenotype similar or identical to ap1-1 mutant plants, which lack AP1 activity, indicating that the activity of both the introduced and endogenous copies of AP1 was suppressed. Analysis of AP1 expression levels by RNA in situ hybridization demonstrated that AP1 expression was reduced and delayed in the cosuppressed transgenic lines having the ap1 mutant phenotype. Futhermore, in a samll fraction of the cosuppressed transgenic lines, a enhanced phenotype resembling the cauliflower phenotype was observed. This enhanced phenotype indicated that introduction of an AP1 construct can supress expression of both endogenous AP1 and CAL.

Although the invention has been described with reference to the examples above, it should be understood that various modifications can be made without departing from the spirit of the invention. Accordingly, the invention is limited only by the following claims.

We claim:

1. A non-naturally occurring seed plant, comprising a first ectopically expressible nucleic acid molecule encoding CAULIFLOWER (CAL), provided that said seed plant does not contain a mutation in an endogenous TERMINAL FLOWER gene that results in ectopic expression of said CAL.

2. The non-naturally occurring seed plant of claim 1, which is characterized by early reproductive development.

3. The non-naturally occurring seed plant of claim 1, which is an angiosperm.

4. The non-naturally occurring angiosperm of claim 3, which is selected from the group consisting of:

cereal plant;

leguminous plant;

oilseed plant;

flowering tree;

fruit-bearing plant;

hop-bearing plant;

ornamental flower;

coffee plant; and cacao plant.

5. The non-naturally occurring seed plant of claim 1, which is a gymnosperm.

6. The non-naturally occurring gymnosperm of claim 5, which is a conifer.

7. The non-naturally occurring seed plant of claim 1, comprising a transgenic seed plant having a first exogenous gene regulatory element that regulates said first ectopically expressible nucleic acid molecule.

8. The transgenic seed plant of claim 7, wherein said first ectopically expressible nucleic acid molecule is a first exogenous nucleic acid molecule.

9. The transgenic seed plant of claim 1, wherein said CAL has an amino acid sequence selected from the group consisting of SEQ ID NO: 10 and SEQ ID NO: 12.

10. The non-naturally occurring seed plant of claim 1, further comprising a second ectopically expressible nucleic acid molecule encoding a MADS domain containing floral meristem identity gene product, wherein said MADS domain containing floral meristem identity gene product is not CAL and provided that said seed plant does not contain a mutation in an endogenous TERMINAL FLOWER gene that results in ectopic expression of said MADS domain containing floral meristem identity gene product.

11. The transgenic seed plant of claim 7, further comprising a second exogenous gene regulatory element that regulates a second ectopically expressible nucleic acid molecule encoding a MADS domain containing floral meristem identity gene product, wherein said MADS domain containing floral meristem identity gene product is not CAL.

12. The transgenic seed plant of claim 8, further comprising a second exogenous gene regulatory element that regulates a second ectopically expressible nucleic acid molecule encoding a MADS domain containing floral meristem identity gene product, wherein said MADS domain containing floral meristem identity gene product is not CAL.

13. The transgenic seed plant of claim 12, wherein said second ectopically expressible nucleic acid molecule is a second exogenous nucleic acid molecule encoding said MADS domain containing floral meristem identity gene product, wherein said MADS domain containing floral meristem identity gene product is not CAL.

14. The transgenic seed plant of claim 13, wherein said second exogenous nucleic acid molecule encodes AP1.

15. The transgenic seed plant of claim 14, wherein said AP1 has an amino acid sequence selected from the group consisting of SEQ ID NO: 2, SEQ ID NO: 4, SEQ ID NO: 6 and SEQ ID NO: 8 and said CAL has an amino acid sequence selected from the group consisting of SEQ ID NO: 10 and SEQ ID NO: 12.

16. A method of converting shoot meristem to floral meristem in an angiosperm, comprising ectopically expressing a first nucleic acid molecule encoding CAULIFLOWER (CAL) in the angiosperm, provided that said angiosperm does not contain a mutation in an endogenous TERMINAL FLOWER gene that results in ectopic expression of said CAL.

17. A method of promoting early reproductive development in a seed plant, comprising ectopically expressing a first nucleic acid molecule encoding CAULIFLOWER (CAL) in the seed plant, provided that said seed plant does not contain a mutation in an endogenous TERMINAL FLOWER gene that results in ectopic expression of said CAL.

18. The method of claim 16, comprising introducing said first nucleic acid molecule encoding CAL into said angiosperm.

19. The method of claim 18, further comprising introducing a second ectopically expressible nucleic acid molecule encoding a MADS domain containing floral meristem identity gene product into the angiosperm, wherein said MADS domain containing floral meristem identity gene product is not CAL.

20. The method of claim 17, comprising introducing said first ectopically expressible nucleic acid molecule encoding CAL into the seed plant.

21. The method of claim 20, further comprising introducing a second ectopically expressible nucleic acid molecule encoding a MADS domain containing floral meristem identity gene product into the seed plant, wherein said MADS domain containing floral meristem identity gene product is not CAL.

* * * * *